US008513491B2

(12) United States Patent
Amor et al.

(10) Patent No.: US 8,513,491 B2
(45) Date of Patent: Aug. 20, 2013

(54) DEHYDRIN GENES AND PROMOTERS FROM COFFEE

(75) Inventors: Mohamed Ben Amor, Tebag-Korba (TN); James Gèrard McCarthy, Noizay (FR); Vincent Petiard, Tours (FR); Steven D. Tanksley, Dryden, NY (US); Chenwei Lin, Menlo Park, CA (US)

(73) Assignees: Nestec S.A., Vevey (CH); Cornell Research Foundation, Ithaca, NY (US)

(*) Notice: Subject to any disclaimer, the term of this patent is extended or adjusted under 35 U.S.C. 154(b) by 923 days.

(21) Appl. No.: 11/922,978

(22) PCT Filed: Jul. 5, 2006

(86) PCT No.: PCT/US2006/026234
§ 371 (c)(1),
(2), (4) Date: Nov. 20, 2009

(87) PCT Pub. No.: WO2007/005980
PCT Pub. Date: Jan. 11, 2007

(65) Prior Publication Data
US 2010/0154073 A1 Jun. 17, 2010

Related U.S. Application Data

(60) Provisional application No. 60/696,890, filed on Jul. 6, 2005.

(51) Int. Cl.
*A01H 1/00* (2006.01)
*A01H 5/00* (2006.01)
*C12N 5/14* (2006.01)
*C12N 15/82* (2006.01)
*C12N 15/63* (2006.01)
*C07H 21/04* (2006.01)

(52) U.S. Cl.
USPC ........ 800/298; 435/320.1; 435/410; 435/419; 536/23.6; 800/287; 800/289; 800/295; 800/278

(58) Field of Classification Search
USPC ............... 435/6.1, 468, 412, 419, 183, 320.1; 530/370; 536/23.1, 23.2, 24.1; 800/320.1, 800/260, 278, 295
See application file for complete search history.

(56) References Cited

U.S. PATENT DOCUMENTS

| | | | |
|---|---|---|---|
| 3,962,321 A | 6/1976 | Parliment et al. | |
| 4,072,761 A | 2/1978 | Margolis et al. | |
| 5,731,419 A * | 3/1998 | Sarhan et al. | 530/375 |
| 5,981,842 A * | 11/1999 | Wu et al. | 800/298 |

FOREIGN PATENT DOCUMENTS

| | | |
|---|---|---|
| WO | WO 01/77384 | 10/2001 |
| WO | WO 03/027249 | 4/2003 |
| WO | WO/2005/126697 | 12/2005 |

OTHER PUBLICATIONS

Guo HH et al. Protein tolerance to random amino acid change. PNAS. 2004(101): 25, 99 9205-9210.*
Chintamaneni CD et al. A single base insertion in the putative transmembrane domain of the tyrosinase gene as a cause for tyrosinase-negative oculocutaneous albinism. Proc. Natl. Acad. Sci. USA. 1991(88): pp. 5272-7276.*
Nylander M et al. Stress-induced accumulation and tissue-specific localization of dehydrins in *Arabidopsis thaliana*. Plant Molecular Biology. 2001. (45): pp. 263-279.*
DeMatta FM. Exploring drought tolerance in coffee: a physioloigcal approach with some insights for plant breeding. Brazilian Journal of Plant Physiology. 2004(16): 1, pp. 1-6.*
Kasuga M et al. A combination of the *Arabidopsis* DREB1A gene and stress-inducible rd29A promoter improved drought- and low-temperature stress tolerance in tobacco by gene transfer. Plant Cell Physiology. 2004(45): 3, pp. 346-350.*
Nylander M et al. Stress-induced accumulation and tissue-specific localization of dehydrins in *Arabidopsis thaliana*. Plant Molecular Biology (45): pp. 263-279.*
Marraccini et al (Plant Physiol. Biochem., 37:273-282, 1999).*
Allagulova, C.H. et al., "the Plant Dehydrins: Structure and Putative Functions," *Biochemistry, Biokhimii A*, Sep. 2003, vol. 68(9), Sep. 2003, pp. 945-951, XP009079176, whole document.
Breton G. et al., "Biotechnological Applications of Plant Freezing Associated Proteins," *Biotechnology Annual Review* 2000, vol. 6, pp. 59-101, XP001062997, whole document.
Chenwei, L. et al., "Coffee and Tomato Share Common Gene Repertoires as Revealed by Deep Sequencing of Seed and Cherry Transcripts," *Theoretical and Applied Genetics*, International Journal of Plant Breeding Research, Springer-Verlag, BE, vol. 112(1), Dec. 2005, pp. 114-130, CP019322122, whole document.
Fernandez, D. et al., "Coffee (Coffee Arabica L.) Genes Early Expressed During Infection by the Rust Fungus (Hemileia Vastatrix)," *Molecular Plant Pathology*, vol. 5(6), Nov. 2004, pp. 527-536, XP002421282.
Hinniger, C. et al., "Isolation and Characterization of cDNa encoding Three Dehydrins Expressed During Coffee Canephora (Robusta) Grain Development," *Annals of Botany*, May 2006, vol. 97, No. 5, pp. 755-765, XP009079141, whole document.
Kasuga M. et al., "a Combination of the *Arabidopsis* DREB1a Gene and Stress-Inducible rd29a Promoter Improved Drought- and Low-Temperature Stress Tolerance in Tobacco by Gene transfer," *Plant & Cell Physiology*, Mar. 2004, vol. 45(3), Mar. 2004, pp. 346-350, XP002421281.
Kaye, C. et al., "Characterization of a Gene for Spinach CAP160 and Expression of Two Spinach Cold-Acclimation Proteins in Tobacco," *Plant Physiology* (Rockville), vol. 116(4), Apr. 1998, pp. 1367-1377, XP002421536.
Satos, et al., "Structural Analysis of *Arabidopsis thaliana* Chromosome 3: I Sequence Features of the Regions of 4,504,864 by Covered by Sixty P1 and TAC Clones," *GENBANK*, vol. 28 Apr. 2000 (Apr. 28, 2000), XP002974277.

(Continued)

*Primary Examiner* — Anne Grunberg
*Assistant Examiner* — Ashley K Buran
(74) *Attorney, Agent, or Firm* — Potter Anderson and Corroon, LLP

(57) ABSTRACT

Dehydrin- and late embryogenic abundant (LEA) protein-encoding polynucleotides from coffee plants are disclosed. Also disclosed are a promoter sequence from a coffee dehydrin gene, and methods for using these polynucleotides and promoter sequences for gene regulation and manipulation of flavor, aroma, stress tolerance and other features of coffee beans.

13 Claims, 10 Drawing Sheets

(56) References Cited

OTHER PUBLICATIONS

Wise, M.J. et al., "POPP the Question: What do LWa Proteins do?" *Trends in Plant Science*, vol. 9(1), Jan. 2004, pp. 13-17, XP002421537, whole document.

Agrawal, N. et al., "RNa Interference: Biology, Mechanism, and Applications," *Microbiol. Mol. Biol. Rev.*, vol. 67:657-685 (2003).

Allagulova, C.R. et al., "the Plant Dehydrins: Structure and Putative Functions," *Biochemistry—Moscow*, vol. 68: 945-951 (2003).

Alsheikh, M.K. et al., "Ion Binding Properties of the Dehydrin ERD14 are Dependent Upon Phosphorylation," *J. Biol. Chem.*, vol. 278: 40882-40889 (2003).

Baumlein, H. et al., "Cis-Analysis of a Seed Protein Gene Promoter: the Conservative RY Repeat CATGCATG Within the Legumin Box Is Essential for Tissue-Specific Expression of a Legumin Gene," *Plant J.*, vol. 2: 233-239 (1992).

Brummelkamp, T.R. et al., "a System for Stable Expression of Short Interfering Rnas in Mammalian Cells," *Science*, vol. 296:550-553 (2002).

Chatthai, M. "2S Storage Protein Gene of Douglas-Fir: Characterization and Activity of Promoter in Transgenic Tobacco Seeds," *Plant Physiol Biochem*, vol. 42: 417-423 (2004).

Choi, D.W. et al., "a Newly Identified Barley Gene, Dhn12 Encoding a YSK2 DHN, Is Located on Chromosome 6H and has Embryo-Specific Expression," *Theoretical and Applied Genetics*, vol. 1274-1278 (2000).

Close, T. "Dehydrins: Emergence of a Biochemical Role of a Family of Plant Dehydration Proteins," *Physiol. Plant*, vol. 97: 795-803 (1996).

Close, T.J. "Dehydrins: a Commonality in the Response of Plants to Dehydration and Low Temperature," *Physiol. Plant*, vol. 100: 291-296 (1997).

Clough, S.J. et al., "Floral Dip: a Simplified Method for *Agrobacterium*-Mediated Transformation of *Arabidopsis thaliana*," *Plant Journal*, vol. 16; 735-743 (1998).

Crouzillat, D. et al., "*Theobroma Cacao* L.: a Genetic Linkage Map and Quantitative Trait Loci Analysis," *Theor. Appl. Genet.*, vol. 93: 205-214 (1996).

Dubouzet, J.G. et al., "Osdreb Genes in Rice, *Oryza sativa* L., Encode Transcription Activators That Function in Drought-, High-Salt- and Cold-Responsive Gene Expression," *Plant J.*, vol. 33: 751-763 (2003).

Dure, L. "Structural Motifs in LEa Proteins of Higher Plants," In: Close, T. J., Bray, E, and A. (Eds), *Response of Plants to Cellular Dehydration During Environmental Stress*, pp. 91-103. American Society of Plant Physiologists, Rockville, MD. (1993).

Dure, L. et al., "Developmental Biochemistry of Cottonseed Embryogenesis and Germination: Changing Messenger Ribonucleic Acid Populations as Shown by in Vitro and in Vivo Protein Synthesis," *Biochemistry*, vol. 20: 4162-4178 (1981).

Elbashir S.M. et al., "Analysis of Gene Function in Somatic Mammalian Cells Using Small Interfering Rnas," *Methods*, vol. 26:199-213 (2002).

Godoy, J.A. et al., "Expression, Tissue Distribution and Subcellular Localization of Dehydrin TAS14 in Salt-Stressed Tomato Plants," *Plant Mol. Biol.*, pp. 1921-1934 (1994).

Hara, M. et al., "Radical Scavenging Activity and Oxidative Modification of Citrus Dehydrin," *Plant Physiology and Biochemistry*, vol. 42: 657-662 (2004).

Hara, M. et al., Enhancement of Cold Tolerance and Inhibition of Lipid Peroxidation by Citrus Dehydrin in Transgenic Tobacco, *Planta*, vol. 217: 290-298 (2003).

Iida, K. et al., "Genome-Wide Analysis of Alternative Pre-Mrna Splicing in *Arabidopsis thaliana* Based on Full-Length Cdna Sequences," *Nucleic Acids Research*, vol. 32: 5096-5103 (2004).

Ingram, J. et al., the Molecular Basis of Dehydration Tolerance in Plants. *Annu .Rev. Plant Physiology Plant Mol Bio.*, vol. 47: 377-403 (1996).

Iwasaki, T. et al., "Identification of a Cis-Regulatory Region of a Gene in *Arabidopsis thaliana* Whose Introduction by Dehydration Is Mediated by Abscisic Acid and Requires Protein Synthesis," *Molecular and General Genetics*, vol. 247: 391-398 (1995).

Klahre, U. et al., "High Molecular Weight RNAs and Small Interfering Rnas Induce Systemic Post-Transcriptional Gene Silencing in Plants," *Proc. Natl. Acad. Sci. USA*, vol. 99:11981-11986 (2002).

Koag, M.C. et al., "the Binding of Maize DHN1 to Lipid Vesicles. Gain of Structure and Lipid Specificity," *Plant Physiology*, vol. 131: 309-316 (2003).

Marraccini, P. et al., "Molecular Cloning of the Complete 11S Seed Storage Protein Gene of *Coffea arabica* and Promoter Analysis in the Transgenic Tobacco Plants," *Plant Physiol. Biochem.*, vol. 37:273-282, 1999.

Marraccini, P. et al., Rubisco Small Subunit of *Coffea arabica*: Cdna Sequence, Gene Cloning and Promoter Analysis in Transgenic Tobacco Plants. *Plant Physiol. Biochem.*, vol. 41:17-25, 2003.

Matsuyama, T. et al., "Maize Genes Specifically Expressed in the Outermost Cells of the Root Cap," *Plant Cell Physiol.*, vol. 40: 469-476 (1999).

Mishra, R.N. et al., "Directional Genome Walking Using PCR," *Biotechniques*, vol. 33:830-834 (2002).

Moore, R. et al., "Ultrastructural Aspects of Cellular Differentiation in the Root Cap of *Zea mays*," *Can. J. Bot.*, vol. 61: 1566-1572 (1983).

Nylander, M. et al., "Stress-Induced Accumulation and Tissue-Specific Localization of Dehydrins in *Arabidopsis thaliana*," *Plant Molecular Biology*, vol. 45: 263-279 (2001).

Puhakainen, T. et al., "Overexpression of Multiple Dehydrin Genes Enhances Tolerance to Freezing Stress in *Arabidopsis*," *Plant Molecular Biology*, vol. 54: 743-753 (2004).

Rishi, A.S. et al., "Genome Walking of Large Fragments: an Improved Method," *J. Biotechnol,.* vol. 111:9-15 (2004).

Roberts, J. et al., "Cellular Concentrations and Uniformity of Cell-Type Accumulation of Two LEa Proteins in Cotton Embryos," *Plant Cell*, vol. 5: 769-780 (1993).

Rogers, W.J. et al., Biochemical and Molecular Characterisation and Expression of the 11S-Type Storage Protein From *Coffea arabica* Endosperm, *Plant Physiol. Biochem.* 37(4): 261-272, (1999).

Shirsat. A. et al., "Sequences Responsible for the Tissue Specific Promoter Activity of a *Pea legumin* Gene in Tobacco," *Molecular and General Genetics*, vol. 215: 326-331 (1989).

Skriver, K. et al., "Gene Expression in Response to Abscisic Acid and Osmotic Stress," *Plant Cell*, vol. 2: 503-512 (1990).

Soulages, J.L. et al., "Conformation of a Group 2 Late Embryogenesis Abundant Protein From Soybean. Evidence of Poly (L-Proline)-Type II Structure," *Plant Physiology*, vol. 131: 963-975 (2003).

Spanier, A.M. et al., "Meat Flavor: Contribution of Proteins and Peptides to the Flavor of Beef," *Adv .Exp. Med. Biol.*, vol. 542: 33-49 (2004).

Turner, J. et al., "Real-Time Monitoring of Thermal Flavor Generation in Skim Milk Powder Using Atmospheric Pressure Chemical Ionization Mass Spectrometry," *J. Agric. Food Chem.*, vol. 50: 5400-5404 (2002).

Tuschl, T. et al., "Small Interfering Rnas: a Revolutionary Tool for the Analysis of Gene Function and Gene Therapy," *Mol. Interventions*, vol. 2:158-167 (2002).

Wise, M. et al., "POPP the Question: What Do LEa Proeins Do?" *Trends Plant Sci.*, vol. 9:13-17 (2004).

Zhu, B. et al., "Expression of the Barley Dehydrin Multigene Family and the Development of Freezing Tolerance," *Molecular and General Genetics*, vol. 64: 145-153 (2000).

\* cited by examiner

FIG. 1

```
  1 MADQYEKK----------------------VEEGS-ANVEATDRGLFDFLGKKEEKPTHAQEEHAISSEF  BAD13499_tobacco
  1 MADQYEQNK---------------PSVEETVGANVEATDRGLFDFLGKKEEKPSHAEEEAISSEF      T07779_potato
  1 MAEEYKNNVKEHETPTVATEESPATTTHVDRGLFDFLGKKEEEV--KPQETTLESEF              CAA62449_Arabidopsis
  1 MA-EYPQSN-------IKVEEGS--AVEATDRGLFN--LGKKEEVK--KCDQGQAISAEF           CcDH3

49 VEKVKVSEEVA----------------EYKEEKKEH-INKEEKLHRSSSSSSSSD                BAD13499_tobacco
 53 CEKVKVSEE----------------EHIKEEEK--KEEKIKLHRSSSSSSSSD                  T07779_potato
 58 DHKAQISE-PELAAEHEEVKENKITLEELQEKHEEDEENKPSVIEKLHRSNSSSSSSSD            CAA62449_Arabidopsis
 47 DEKVRVSEP---------------DKEEGKKI--HGGLLEKLHRSGSSSSSSE                  CcDH3

90 EEEIGEDGQK--------EHKEEEKAG----EDTAVPVEKYEE                            BAD13499_tobacco
 87 EEEIGEDGQT--------DHKEEVKT-----EDTSVPVEKYEE                            T07779_potato
117 EEGEEKKKKIVEGEED-KKFKIKEKIKG-VSITIPVPVSES                              CAA62449_Arabidopsis
 83 EEVE-GE--KK--KKKKGLKDKIKEKIKG-DKTAEDDVP--VEKKCFEDTSIPVEKYAE            CcDH3

141 IKKKKKKGLKDKIKDKISG------EEKKGFLDKIKEKLPGGQKKTEEVAP--PL--AAEHEAE       BAD13499_tobacco
137 IKKKKKGLKDKIKEKISG------BEKKGFLDKIKEKLPGGHKKTEEVAA--PPP--AAVEHEAE      T07779_potato
173 KKKKKKGLKDKIKEKLPGH-VVEHDHPE--BEKKGLVEKIKIKEKL-HDEKAEDSPAVTSIPLVVTEHPVEPITELPVE  CAA62449_Arabidopsis
136 KKKKGLKDKIKEKISG-DKKIEEKVEKCFEDTSIPVEKYAE-PAHADAAHEPDDKKGFLDKIKEKLPGGQKKTEEVAA--APPP-  PDAECTATEGE  CcDH3

180 G--KEKKGFLDKIKEKLPGYHSKT----EEKIKIK                                    BAD13499_tobacco
179 G--KEKKGFLDKIKEKLPGYHSKT----EEEEKEKEKN                                 T07779_potato
230 HPEEKKGIIEKIKEKLPGYHAKT--EEEVKIKEKESDD                                 CAA62449_Arabidopsis
189 A--KDKKGFLDKIKEKLPGYHPKT--EEEEKEKEKEKEAGCH.                            CcDH3
```

```
atagtgacct taatagcgat cttgttgctt ttgatcgtca gaaaagtagt ggacatgacg      60
gaagaggtcc taagatgagt tccagttcca gcatgaaggg ctctttggcg aagcctttct     120
tgaggcgtca cttttctttt ggatctaaag gcagtagatc aatgtcagag aatcattctt     180
cctggaagag gggattcttc tgggcaaaat cgagaaagga ttaagttctg tctagagtta     240
caaaggtgag caacagtcac ggttttttat tagggaatgg aaggattgga tcccttttca     300
cgtagtgaac aacatatatt ttgcatggtt ggtcttagta cctataacac gaaaatgttc     360
ttcatccgtt ctattaatca ttaggcttta gtcatttaaa ttttttacat cccgcatttc     420
tcctcttgat tcttgttgat ttctgcagat tccacagttg ttcttcagat gggctacgaa     480
atgcatgcag ggagcaggca atcagccata aattcaaccc tgtcaaggaa gctggcattg     540
tctcgtgcaa atgtaggtta gcttttgaag atacactgca aagggaagac catacagatg     600
gggaaatgaa ttcattataa tataggaaaa aggaaagatg atagggggtca gggcgtccgt     660
gcatcatgaa actagttctc tttcattttg tacgatggct gtttactgtt taatttcatg     720
aaattagttt ggatatatgc gtagcgtttt accatcgcat ttctaaatcg atattctatg     780
ggccgaatta cgcgttggag acatcattgg gttgctcctc tcaatcccat ctctatctat     840
tgacggatcc ggatcatgat gttgaacctt tcaacttttg acttagatgg gatttgtgtt     900
cgcgtgttgt taacttgtta ctgaccgact cagaagacag cggattctga cttcaccacg     960
tgtctcttta gtgaaaattt aaaaggcatt tttcttctgt tcatagttta aatgtaatg    1020
tgattattaa aagatcgttt ggtattattt caaggatgga tggattggat ggaagggata    1080
tctgatatat atcataccct tccaaaattc aggaccatga cgtatttaat atccccagc    1140
ggaagacacg tgcctgatg tcttataggt ggcaatacac ttcagcttcc tctgctaata    1200
cgtgtgagga tcttcggtac catgcagaaa agaccgcggt gctccttcca ccgtcctcat    1260
ccctctcttg gcttttttaa gtctcctgcg atatccaaaa tccaaacaaa gccgttatcg    1320
cagCaaaat tcgtcaaccc caagtctcag gctaccttaa tttcagtgcc cttttctttt    1380
atttttttct aataacagga gtcctggaaa atg gct gac ttg cgt gat gaa tat    1434
                                                     1         5
gga aat cct atg cag ttg acc gac cag tat ggc aac ccg gtt cag ctc    1482
Gly Asn Pro Met Gln Leu Thr Asp Gln Tyr Gly Asn Pro Val Gln Leu
 10              15                  20
aag gac gag tat ggc aac cca atg cag ctt agc ggt gta gct atc acc    1530
Lys Asp Glu Tyr Gly Asn Pro Met Gln Leu Ser Gly Val Ala Ile Thr
 25              30                  35                  40
gcc ggg acg gct agt act gtc cat tct act gga acc gga cca act gct    1578
Ala Gly Thr Ala Ser Thr Val His Ser Thr Gly Thr Gly Pro Thr Ala
                 45                  50                  55
gcc act gga acc cag caa cat cag gag cag ctt cat cgg tct agc agc    1626
Ala Thr Gly Thr Gln Gln His Gln Glu Gln Leu His Arg Ser Ser Ser
                 60                  65                  70
tca agc tct ggc tcg     gtgagatact tgccaagtta caatgtgtgt gtctgtgtgt    1681
Ser Ser Ser Gly Ser
                 75
gtataatgcg ccatcataat tgtttgcttg acagatcctg ttaataatga accgtaattt    1741
gacgtaaagt gtacacgttt tgttttctg ggactaacat aatatcgaat caggctcctg    1801
ttgaatttga atgttgttag ctaaaagaaa attttggtgg ctgagttgtt gaatttggtt    1861
tatag acg gag gat gat gga caa gga gga aga aga aag aaa aaa ggg ttg    1911
      Thr Glu Asp Asp Gly Gln Gly Gly Arg Arg Lys Lys Lys Gly Leu
             80                  85                  90
aaa gaa aag ata aag gag aaa cta acg ggc ggt agg cac aag gac aga    1959
Lys Glu Lys Ile Lys Glu Lys Leu Thr Gly Gly Arg His Lys Asp Arg
 95                 100                 105
gac gat cag gag cac atc gat gat cag cac gcg cac agc gcc tct cct    2007
Asp Asp Gln Glu His Ile Asp Asp Gln His Ala His Ser Ala Ser Pro
    110                 115                 120
cca aca acc acc act ggc agc ggg acg tct act aca gtc ggg ggt cag    2055
Pro Thr Thr Thr Thr Gly Ser Gly Thr Ser Thr Thr Val Gly Gly Gln
125                 130                 135                 140
cag cat gaa aag aag agc atg gtg gag aag att atg gaa aag ctc cct    2103
Gln His Glu Lys Lys Ser Met Val Glu Lys Ile Met Glu Lys Leu Pro
                145                 150                 155
ggc cat cac gac acc cgc tag ttaccta ccacaacata ctgtgatcat    2151
Gly His His Asp Thr Arg STOP
                160
cgtgtaaaat ctctcctgat gcctaggaaa tctagattat gttaggcatt ttgtttggta    2211
tgtatgtgtg attaagacct tgttgtgcgc ttgaatcttg aacgtgcatg ggatttgctt    2271
ggtttgattt gatttgg
```

DEHYDRIN GENES AND PROMOTERS FROM COFFEE

This is a U.S. National Application of International Application No. PCT/US06/26234, filed Jul. 5, 2006, which claims benefit of U.S. Provisional Application No. 60/696,890, filed Jul. 6, 2005, the entire contents of each of which are incorporated by reference herein.

FIELD OF THE INVENTION

The present invention relates to the field of agricultural biotechnology. In particular, the invention features dehydrin-encoding polynucleotides from coffee plants, promoter sequences from coffee dehydrin genes, and methods for using these polynucleotides and promoters for gene regulation and manipulation of flavor, aroma and other features of coffee beans.

BACKGROUND OF THE INVENTION

Various publications, including patents, published applications and scholarly articles, are cited throughout the specification. Each of these publications is incorporated by reference herein, in its entirety. Citations not fully set forth within the specification may be found at the end of the specification.

Coffee aroma and flavor are key components in consumer preference for coffee varieties and brands. Coffee's characteristic aroma and flavor stems from a complex series of chemical reactions involving flavor precursors (Maillard reactions) that occur during the roasting of the bean. Flavor precursors include chemical compounds and biomolecules present in the green coffee bean. To date, over 800 chemicals and biomolecules have been identified as contributing to coffee flavor and aroma. (Montavon et al., J. Agric. Food Chem., 51:2328-34 (2003)).

Because coffee consumers are becoming increasingly sophisticated, it is desirable to produce coffee with improved aroma and flavor in order to meet consumer preferences. Both aroma and flavor may be artificially imparted into coffee products through chemical means. See, for example, U.S. Pat. No. 4,072,761 (aroma) and U.S. Pat. No. 3,962,321 (flavor). However, to date, there is little data concerning the influence of natural coffee grain components such as polysaccharides, proteins, and lipids on coffee aroma and flavor. One approach is to select varieties from the existing germplasm that have superior flavor characteristics. A disadvantage to this approach is that, frequently, the highest quality varieties also possess significant negative agronomics traits, such as poor yield and low resistance to diseases and environmental stresses. It is also possible to select new varieties from breeding trials in which varieties with different industrial and agronomic traits are crossed and their progeny are screened for both high quality and good agronomic performance. However, this latter approach is very time consuming, with one crossing experiment and selection over three growing seasons taking a minimum of 7-8 years. Thus, an alternative approach to enhancing coffee quality would be to use techniques of molecular biology to enhance those elements responsible for the flavor and aroma that are naturally found in the coffee bean, or to add aroma and flavor-enhancing elements that do not naturally occur in coffee beans. Genetic engineering is particularly suited to achieve these ends. For example, coffee proteins from different coffee species may be swapped. In the alternative, the expression of genes encoding naturally occurring coffee proteins that positively contribute to coffee flavor may be enhanced. Conversely, the expression of genes encoding naturally occurring coffee proteins that negatively contribute to coffee flavor may be suppressed. Another application of modern techniques is to use molecular information concerning the association of high quality with specific alleles to screen new varieties for the presence or absence of such using marker assisted breeding.

Coffees from different varieties and origins exhibit significant flavor and aroma quality variations when the green grain samples are roasted and processed in the same manner. The quality differences are a manifestation of chemical and physical variations within the grain samples that result mainly from differences in growing and processing conditions, and also from differences in the genetic background of both the maternal plant and the grain. At the level of chemical composition, at least part of the flavor quality can be associated with variations in the levels of small metabolites, such as sugars, acids, phenolics, and caffeine found associated with grain from different varieties. It is accepted that there are other less well characterized flavor and flavor-precursor molecules. In addition, it is likely that structural variations within the grain probably also contribute to differences in coffee quality. One approach to finding new components in the coffee grain linked to coffee quality is to study the genes and proteins differentially expressed during the maturation of grain samples in different varieties that possess different quality characteristics.

A group of proteins called the late embryogenesis abundant proteins (LEA), have been shown to accumulate in a coordinated fashion during the latter stages of cotton seed development (Dure, L, et al. Biochemistry 20: 4162-4178 (1981)). Dehydrin proteins (DHN) are a sub-group of the LEA proteins that have also been called the "LEA D-11 family" or LEA type 2 proteins (Close, T, Physiol. Plant 97: 795-803 (1996); Ingram, J, Annu. Rev. Plant Physiology Plant Mol Biol 47: 377-403 (1996)). Expression of the DHN proteins has been associated with the protection of various types of plant cells from osmotic stresses, such as those caused by desiccation, salt, and low temperature. (Skriver, K, et al. Plant Cell 2: 503-512 (1990); Allagulova, C R, et al. Biochemistry-Moscow 68: 945-951 (2003)).

In recent years, direct experimental evidence has linked increased expression of dehydrins with protection from osmotic stress. For example, *Arabidopsis* plants engineered to over-express a dehydrin fusion protein were found to have improved survival when exposed to low temperature (Puhakainen, T, et al. Plant Molecular Biology 54: 743-753 (2004)). Similarly, expression of a citrus dehydrin protein in transgenic tobacco has been shown to give increased tolerance to low temperature (Hara, M, et al. Planta 217: 290-298 (2003)). Other supporting evidence for the linkage of dehydrins and tolerance to low temperature induced stress are the observations that QTL loci for freezing tolerance and winterhardiness map very closely to dehydrins (Close T, 1996; Zhu, B, et al. Molecular and General Genetics 264: 145-153 (2000)). DHN genes are also expressed robustly in seeds toward the end of maturation, a period when the seed undergoes a developmentally programmed reduction in water content (Nylander, M, et al. Plant Molecular Biology 45: 263-279 (2001); Choi, D W, et al. Theoretical and Applied Genetics 100: 1274-1278 (2000)). The LEA/dehydrin proteins have been estimated to comprise up to 4% of the total seed protein, and are thought to be involved in protecting the embryo and/or other seed tissues from the osmotic stresses associated with the low water content of the mature seed (Roberts, J, et al. Plant Cell 5: 769-780 (1993); Wise, M, et al. Trends Plant Sci. 9: 13-17 (2004)).

Dehydrins are widely perceived to participate, with other LEA proteins, in the dehydration process that occurs during the late stages of seed maturation by assisting the acclimatization of seed tissues to the lower water content found in mature seeds (Close, Tm 1996); Nylander M, 2001). In addition, it is believed that the dehydrins synthesized seeds during maturation also continue to stabilize the associated cellular structures during seed quiescence. In this latter context, it has recently been proposed that dehydrins may also possess a radical-scavenging capability (Hara, M, 2003) and metal-binding properties (Alsheikh, M K, et al. J. Biol. Chem. 278: 40882-40889 (2003)), both characteristics that are likely to be useful during long periods of seed storage.

A considerable number of dehydrin proteins have been isolated and studied, and the precise physiochemical and/or structural mechanism(s) whereby these proteins function to protect cells from osmotic stress in-vivo is under investigation. The dehydrins are very hydrophilic proteins and exhibit an unusually low level of recognizable structure (Close T, 1996; Soulages, J L, et al. Plant Physiology 131: 963-975 (2003)). A key element of the dehydrins is believed to be the presence of one or more 15 amino acid, lysine rich, stretches called the "K motifs," which are predicted to form class A amphipathic alpha-helices (Close, T, 1996; Close, T J Physiol. Plant 100: 291-296 (1997)). Dehydrins can also contain two other motifs, an N-terminal "Y segment" (consensus V/TDE/QYGNP) and a serine rich "S segment," the latter of which can be phosphorylated and is thought to participate in nuclear localization (Close T J, 1997; Godoy, J A, et al. Plant Mol. Biol. 1921-1934 (1994)). It has been proposed that the short amphipathic K segments of dehydrin polypeptides functionally interact with the solvent-exposed hydrophobic patches of proteins that are undergoing partial denaturation, and thereby block protein aggregate formation (Close T, 1996). Amphipathic K helixes may also be involved in binding membrane lipids, and thus could play a more specific role in protecting lipoproteins, proteins located in membranes, and/or membrane structure itself (Close T, 1996; Koag, M C, et al. Plant Physiology 131: 309-316 (2003)). An alternative proposal for at least part of the protective effect of dehydrins is the ability of these very stable, but relatively unstructured, proteins to tightly bind and organize water molecules (Soulages J L, 2003). This latter effect could lead to reduced water loss from cells, and could also improve the stability of certain macromolecules by the development of dehydrin based region of more tightly bound "ordered" water around these molecules.

Despite the involvement of dehydrin proteins in plant resistance to osmotic stresses such as drought and salt stress, and the probable importance of the dehydrins during grain development, little information is available on these genes in coffee. In coffee, little is understood about the number of dehydrins, their protein structure, their expression levels and distribution in different tissues of the coffee plant and among coffee species, as well as during coffee grain and pericarp maturation, and the regulation of their expression on the molecular level. Thus, there is a need to identify, isolate and characterize coffee dehydrin proteins, genes, and genetic regulatory elements. Such information will enable coffee dehydrin proteins to be genetically manipulated, with the goal of improving the aroma and flavor of the coffee, as well as imparting other phenotypic advantages associated with improved osmotic stress resistance.

Dehydrins, which are expressed at relatively high levels at the end of grain maturation, are of interest because of the potentially important roles they have in organizing water molecules in the coffee grain and in stabilizing macromolecules and organelles within the mature dehydrated grain. At least part of this protective effect is believed to be due to the ability of the dehydrins and other LEA proteins to stabilize different water/protein/lipid interfaces. Because water levels can influence the spectrum of products formed in the Maillard reaction (Turner, J, et al. J. Agric. Food Chem 50: 5400-5404 (2002)), the availability and organization of water molecules in the coffee grain may influence the flavor generating Maillard reaction occurring during the roasting of coffee.

SUMMARY OF THE INVENTION

The invention described herein features dehydrin-encoding polynucleotides from coffee plants, their encoded polypeptides, promoter sequences from coffee dehydrin genes, and methods for using these polynucleotides, polypeptides and promoters for gene regulation and manipulation of flavor, aroma and other features of coffee beans.

One aspect of the invention features a nucleic acid molecule isolated from coffee (*Coffea* spp.), having a coding sequence that encodes a dehydrin or a late embryogenic abundant (LEA) protein. In certain embodiments, the encoded dehydrin has a molecular weight of between about 17 kDa and about 26 kDa. In certain embodiments, the encoded dehydrin or LEA protein has an amino acid sequence that is 46% or more identical to any one of SEQ ID NOS: 7-12. In some embodiments, the coding sequence is 45% or more identical to any one of the coding sequences set forth in SEQ ID NOS: 1-6.

In certain embodiments, the nucleic acid molecule is a gene having an open reading frame that comprises the coding sequence. Alternatively, it may comprise an mRNA molecule produced by transcription of that gene, or a cDNA molecule produced by reverse transcription of the mRNA molecule. The invention also features an oligonucleotide between 8 and 100 bases in length, which is complementary to a segment of the aforementioned nucleic acid molecule.

Another aspect of the invention features a vector comprising the above described dehydrin- or LEA-encoding nucleic acid molecule. In certain embodiments, the vector is an expression vector selected from the group of vectors consisting of plasmid, phagemid, cosmid, baculovirus, bacmid, bacterial, yeast and viral vectors. In certain embodiments, the vector contains the coding sequence of the nucleic acid molecule operably linked to a constitutive promoter. In other embodiments, the coding sequence is operably linked to an inducible promoter. In other embodiments, the coding sequence of the nucleic acid molecule is operably linked to a tissue specific promoter, such as a seed specific promoter, preferably a coffee seed specific promoter. In specific embodiments, the seed specific promoter is a coffee dehydrin gene promoter, such as the promoter contained in SEQ ID NO:13.

According to another aspect of the invention, a host cell transformed with the aforementioned vector is provided. The host cell may be a plant, bacterial, fungal, insect or mammalian cell. In certain embodiments, the host cell is a plant cell selected from any one of coffee, tobacco, *Arabidopsis*, maize, wheat, rice, soybean barley, rye, oats, sorghum, alfalfa, clover, canola, safflower, sunflower, peanut, cacao, tomato tomatillo, potato, pepper, eggplant, sugar beet, carrot, cucumber, lettuce, pea, aster, begonia, chrysanthemum, delphinium, zinnia, and turfgrasses. The invention also features a fertile transgenic plant produced by regenerating the transformed plant cell. In a specific embodiment, the fertile transgenic plant is a *Coffea* species.

Another aspect of the invention features a method to modulate flavor or aroma of coffee beans. The method comprises modulating production of one or more dehydrins or LEA proteins within coffee seeds. In some embodiments, the method comprises increasing production of the one or more dehydrins or LEA proteins, e.g., by increasing expression of one or more endogenous dehydrin- or LEA protein-encoding genes within the coffee seeds, or by introducing a dehydrin- or LEA protein-encoding transgene into the plant. In other embodiments, the method comprises decreasing production of the one or more dehydrins or LEA proteins, e.g., by introducing a nucleic acid molecule into the coffee that inhibits the expression of one or more of the dehydrin- or LEA protein-encoding genes.

Another aspect of the invention features a method to increase resistance to osmotic stress in a plant. This method comprises increasing production of one or more dehydrins or LEA proteins within the plant, e.g., by introducing a dehydrin- or LEA protein-encoding transgene into the plant.

According to another aspect of the invention, a promoter isolated from a dehydrin-encoding coffee plant gene is provided. In certain embodiments, the dehydrin-encoding coffee gene encodes a dehydrin protein having the one or more of the features described above. In certain embodiments, the promoter comprises one or more regulatory sequences selected from the group consisting of a TATA box, an abscisic acid responsive element, an RY repeat (CATGCA(T/a)(A/g) of a leguminin box for regulating expression of leguminin-type proteins, at least one dehydration responsive element/C-repeat cis-acting sequence motif (G/ACCGAC and at least one E-box motif (CANNTG). In a specific embodiment, the promoter comprises SEQ ID NO:13.

The invention also features a chimeric gene comprising a promoter of a coffee dehydrin-encoding gene, operably linked to one or more coding sequences. A vector for transforming a cell, comprising the chimeric gene, is also provided, as well as cells transformed with the vector and fertile transgenic plants produced by regenerating a plant cell transformed with the vector.

Other features and advantages of the present invention will be understood from the drawings, detailed description and examples that follow.

BRIEF DESCRIPTION OF THE DRAWINGS

FIG. 1. Optimal alignment of *Coffea canephora* $Y_3SK_2$-type dehydrins CcDH1a (SEQ ID NO: 7), CcDH1b (SEQ ID NO: 8), CcDH2a (SEQ ID NO: 9), with several close plant homologs. The alignment was generated using the Clustal W program in the MegAlign software (DNASTAR) and then further optimized manually. Identical amino acids are boxed, The solid bars demarcate the Y-segments, the single dark rectangles demarcate the S-segments, and the rectangles with broken lines demarcate the K-segments. The black circle represents the amino acid different between CcDH2a (SEQ ID NO: 9) and CcDH2b (SEQ ID NO: 10). Accession numbers: *Lycopersicon esculentum* dehydrin TAS14 (AAC49618) (SEQ ID NO:14); *Solanum commersonii* dehydrin Dhn1 (CAA75798) (SEQ ID NO:15); *Arabidopsis thaliana* dehydrin RAB18 (NP_201441) (SEQ ID NO:16).

FIG. 2. Optimal alignment of the *Coffea canephora* $SK_3$-type dehydrin CcDH3 (SEQ ID NO: 11) with several close plant homologs. The alignment was generated as described for FIG. 1. Identical amino acids are boxed. The single dark rectangles demarcate the S-segments, and the rectangles with broken lines demarcate the K-segments. Accession numbers: *Nicotiana tabacum* dehydrin (BAD13499) (SEQ ID NO:17); *Solanum tuberosum* dehydrin homolog CI7 (T07779) (SEQ ID NO:18); *Arabidopsis thaliana* dehydrin (CAA62449) (SEQ ID NO:19).

FIG. 3. Optimal alignment of the *Coffea canephora* late embryogenesis abundant protein CcLEA1 (SEQ ID NO: 12) with several close plant homologs. The alignment was generated as described for FIG. 1. Identical amino acids are boxed. Conserved cysteines are marked by an asterisk, and the position of two less highly conserved cysteines are marked by a circle. Accession numbers: *Arabidopsis thaliana* late embryogenesis abundant related protein (NP_200248) (SEQ ID NO:20), *Picea glauca* late embryogenesis abundant protein EMB7 (T09288) (SEQ ID NO:21), *Zea mays* root cap protein 2 (BAA75477) (SEQ ID NO:22).

FIG. 7. DNA sequence of the CcDH2a promoter and transcribed sequence from *Coffea canephora*. The nucleic acid sequence of pVC1 insert (SEQ ID NO: 13) is presented, along with the corresponding amino sequence. The first base in the cDNA (C) is marked by a circle. The putative TATA box is underlined. The RY repeat sequences are marked with a double underline, the ABA responsive elements are boxed, and the DRE/CRT sequence is boxed with heavy lines.

DETAILED DESCRIPTION OF ILLUSTRATIVE EMBODIMENTS

Definitions

Figure 4:
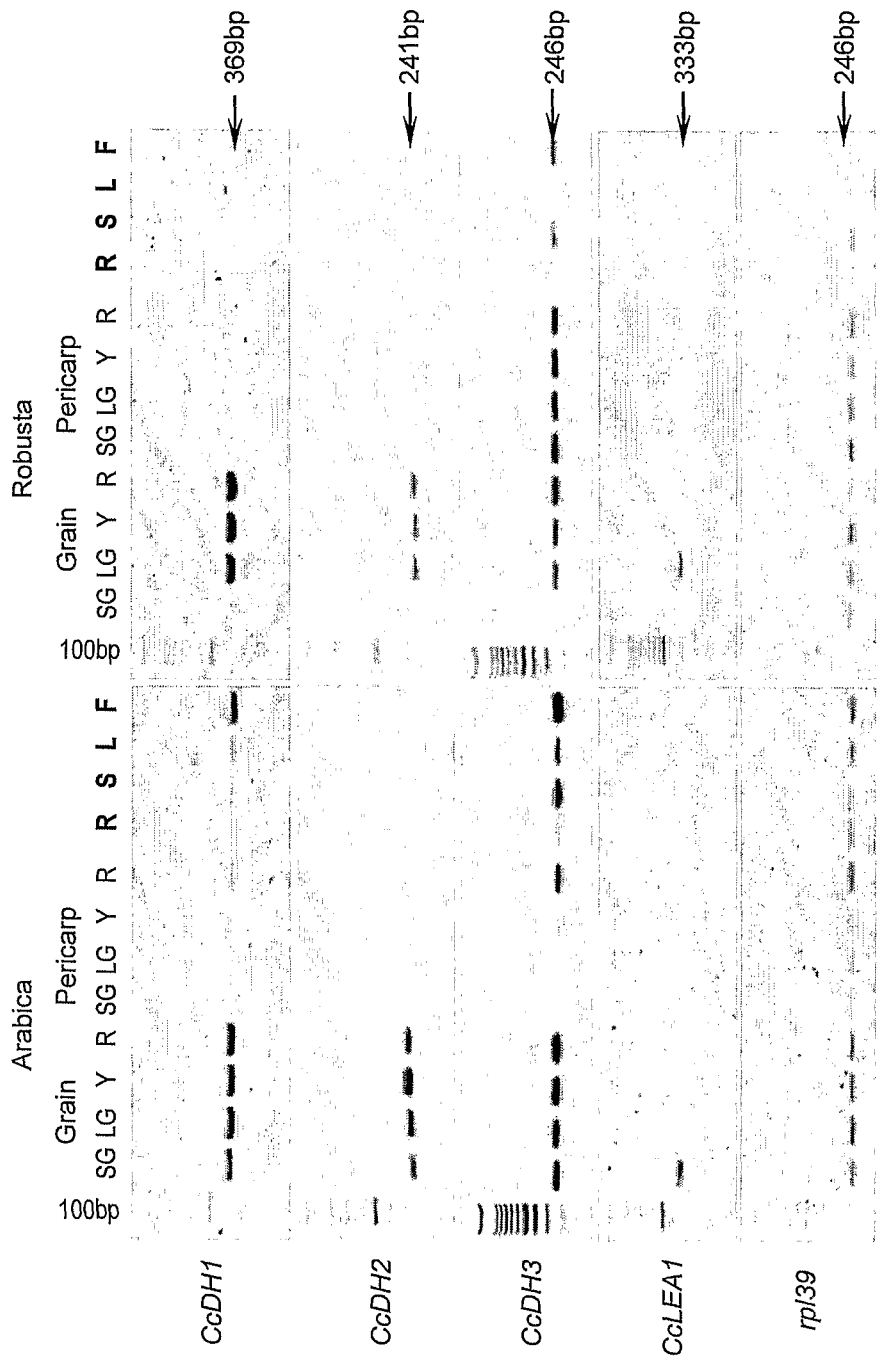
FIG. 4. RT-PCR expression analysis of the coffee dehydrins and CcLEA1 transcripts in different organs of *Coffea arabica* and *Coffea canephora*. 100 bp represents 100 bp molecular weight marker ladder; SG, LG, YG, RG, represent small green, large green, yellow green and red for the grain and pericarp respectively; R, S, L, F represent root, stems, leaves and flowers.

Various terms relating to the biological molecules and other aspects of the present invention are used throughout the specification and claims.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide", also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for Protein Modifications and Nonprotein Cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e., the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g., chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

The term "osmotic stress" refers to any stress on the plant that disrupts the normal water, sugar, or electrolyte concentration in a plant cell or plant on the whole. Osmotic stress may be environmentally related, such as conditions of prolonged low water or drought, low temperatures, frost, freezing temperatures, high salt content in the soil, and the like. Osmotic stress may also occur naturally, as would be expected for seed development and maturation.

DESCRIPTION

In one of its aspects the present invention features nucleic acid molecules from coffee that encode a variety of dehydrin proteins, as well as one other LEA (late embryogenic abundant) protein. Representative examples of dehydrin- and LEA-encoding nucleic acid molecules were identified from databases of over 47,000 expressed sequence tags (ESTs) from several *Coffea canephora* (robusta) cDNA libraries made with RNA isolated from young leaves and from the grain and pericarp tissues of cherries harvested at different stages of development. Overlapping ESTs were identified and "clustered" into unigenes (contigs) comprising complete coding sequences. The unigene sequences were annotated by performing a BLAST search of each individual sequence against the NCBI (National Center for Biotechnology Information) non-redundant protein database. DNA sequence analysis revealed five unique sequences representing three different dehydrin genes and one LEA gene. These cDNAs are referred to herein as CcDH1a (SEQ ID NO:1), CcDH1b (SEQ ID NO:2), CcDH2a (SEQ ID NO:3), CcDH2b (SEQ ID NO:4) and CcDH3 (SEQ ID NO:5). CcDH1a and CcDH1b were found to be allelic variants of each other, while two distinct unigenes were found to encode the open reading frame for CcDH2. In addition, analysis of a cDNA library constructed from RNA isolated from coffee grains at 30 weeks post-fertilization revealed a full-length cDNA clone encoding a coffee LEA protein. This cDNA is referred to herein as CcLEA1 (SEQ ID NO:6).

Figure 8:
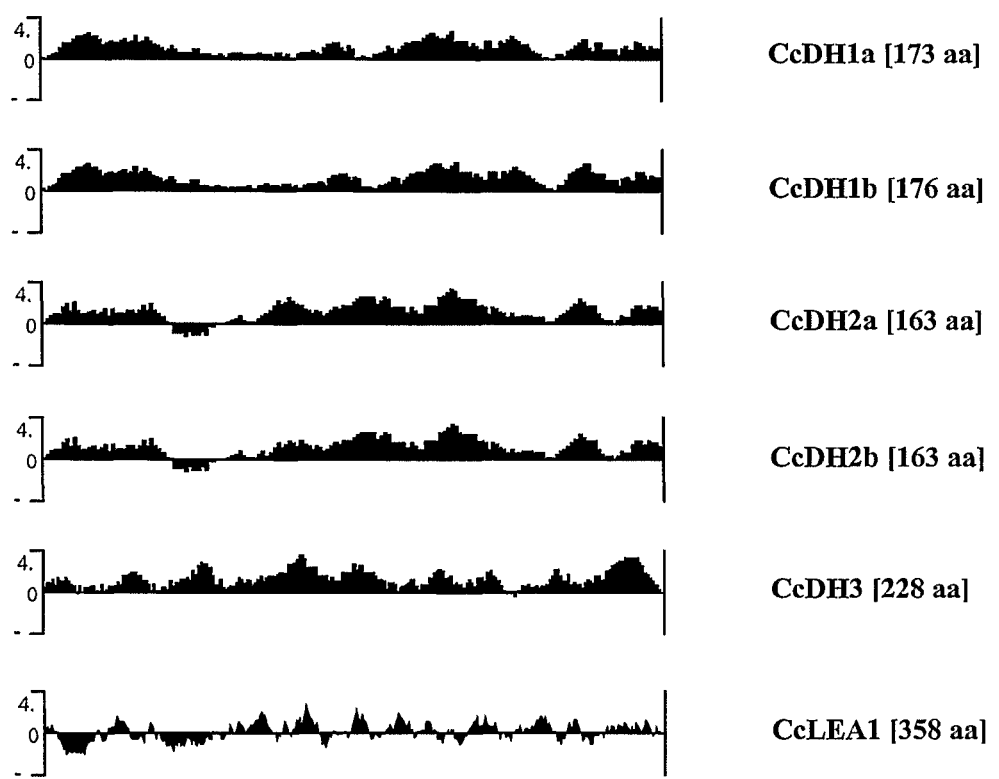
FIG. 8. Kyte-Doolittle hydrophilicity plots of encoded polypeptides. CcDH1a (173 aa, SEQ ID NO:7); CcDH1b (176 aa, SEQ ID NO:8); CcDH2a (163 aa, SEQ ID NO:9); CcDH2b (163 aa, SEQ ID NO:10); CcDH3 (228 aa, SEQ ID NO:11); CcLEA1 (358 aa, SEQ ID NO: 12).

The deduced amino acid sequences of CcDH1a-CcDH3 are set forth herein as SEQ NOS: 7-11. The proteins have molecular masses of approximately 17.8 kDa (CcDH1a, SEQ ID NO:7), 18.1 kDa (CcDH1b SEQ ID NO:8), 17.4 kDa (CcDH2a and CcDH2b, SEQ ID NOS: 9 and 10), and 21.5 kDa (CcDH3, SEQ ID NO:11). These proteins were found to contain signature dehydrin amino acid motifs, and were classified according to those motifs. CcDH1a, CcDH1b, and CcDH2 (a and b) have the structure $Y_3SK_2$, and CcDH3 has the structure $SK_3$. CcDH1a and CcDH1b show absolute conservation in each of the three motifs, and in the two conserved regions that precede each of the two K motifs. In contrast, CcDH2 shows punctual differences in all but one of the Y, S, and K motifs, and more significant differences outside these dehydrin-specific motifs. Hydrophilicity plotting revealed that all of the coffee dehydrin proteins identified herein are very hydrophilic throughout (See FIG. 8).

The deduced amino acid sequence encoded by CcLEA1 is set forth herein as SEQ ID NO:12. This protein has a molecular mass of approximately 39.5 kDa. Hydrophilicity plotting of this protein indicates that this protein is less hydrophilic than the dehydrin molecules, and that there are two small hydrophobic regions, one of which is located in its first 30 N-terminal residues. The N-terminus of CcLEA1 was also found to contain a striking proline-rich segment.

Another aspect of the invention features promoter sequences and related elements that control expression of dehydrin genes in coffee. As described in greater detail in the examples, a promoter sequence (contained in SEQ ID NO:13), from CcDH2a was identified by PCR-assisted primer walking. The CcDH2 promoter was shown to contain several regulatory elements analogous to those previously characterized in other species to be involved in the regulation of gene expression during seed development. These CcDH2 regulatory elements are shown in FIG. 7 and described in the examples. Using this promoter linked to the GUS reporter gene, it has been determined that the promoter is specific to seeds, siliques, cotyledons, hypocotyls and first true leaves of developing seedlings. Moreover, as described in the Examples, expression of the CcDH1 and CcDH2 genes has also been shown to be induced by drought stress and other stress conditions.

Although polynucleotides encoding dehydrins and LEA proteins from *Coffea canephora* are described and exemplified herein, this invention is intended to encompass nucleic acids and encoded proteins from other *Coffea* species that are sufficiently similar to be used interchangeably with the *C. canephora* polynucleotides and proteins for the purposes described below. Accordingly, when the terms "dehydrin" or "late embryogenesis abundant (LEA) proteins" are used herein, they are intended to encompass all *Coffea* dehydrins or LEA proteins that have the general physical, biochemical, and functional features described herein, as well as the polynucleotides that encode them.

Considered in terms of their sequences, dehydrin- and late embryogenesis abundant protein-encoding polynucleotides of the invention include allelic variants and natural mutants of SEQ ID NOs: 1-6, which are likely to be found in different varieties of *C. canephora*, and homologs of SEQ ID NOs: 1-6 likely to be found in different coffee species. Because such variants and homologs are expected to possess certain differences in nucleotide and amino acid sequence, this invention provides isolated dehydrin- or LEA protein-encoding nucleic acid molecules that encode respective polypeptides having at least about 40%, 45%, 50%, or 55%, preferably at least about 60, 65, or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any one of SEQ ID NOs:7-12, and comprising a nucleotide sequence having equivalent ranges of identity to any one of SEQ ID NOs: 1-6. Because of the natural sequence variation likely to exist among dehydrins and LEA proteins, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

As mentioned, the inventors have demonstrated that expression of certain of the dehydrin or LEA protein genes is seed, silique and seedling specific in coffee, as well as being inducible by drought and other forms of stress. Accordingly, the gene regulatory sequences associated with dehydrin- and LEA protein-encoding genes are of practical utility and are considered within the scope of the present invention. The *C. canephora* DH2 promoter is exemplified herein. The upstream region of the *C. canephora* DH2 genomic sequence is set forth herein as SEQ ID NO:13, and contains part or all of an exemplary promoter of the invention, though other portions of the promoter may be found at other locations in the gene, as explained in the definition of "promoter" set forth hereinabove. However, promoters and other gene regulatory sequences of dehydrin and LEA protein genes from any coffee species may be obtained by the methods described below, and may be utilized in accordance with the present invention. The promoters and regulatory elements governing tissue specificity and temporal specificity of dehydrin and LEA protein gene expression may be used to advantage to alter or modify the osmotic stress tolerance of various coffee species, among other utilities.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOs: 1-6, or the regulatory sequence of SEQ ID NO:13, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions of dehydrin- or LEA protein-encoding polynucleotides may be identified by using hybridization and washing conditions of appropriate stringency. It will be appreciated by those skilled in the art that the aforementioned strategy, when applied to genomic sequences, will, in addition to enabling isolation of dehydrin or LEA protein coding sequences, also enable isolation of promoters and other gene regulatory sequences associated with dehydrin or LEA protein genes, even though the regulatory sequences themselves may not share sufficient homology to enable suitable hybridization. Moreover, the annotation of at least a partial coding sequence will enable the skilled artisan to determine the remaining coding sequence, as well the promoter or other gene regulatory sequences associated with the dehydrin or LEA protein of interest by the technique of upstream or downstream genome walking. Such techniques are established in the art. (Mishra R N et al., 2002; Rishi A S et al., 2004).

As a typical illustration, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm = 81.5° C. + 16.6 \text{ Log } [Na+] + 0.41(\% \, G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+(Novagen, Madison, Wis.), all of which can be propagated in a suitable E. coli host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting dehydrin- or LEA protein-encoding genes or mRNA in test samples of plant tissue, e.g., by PCR amplification, or for the positive or negative regulation of expression of dehydrin- or LEA protein-encoding genes at or before translation of the mRNA into proteins. Methods in which dehydrin- or LEA protein-encoding oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR, including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of dehydrins or LEA protein polypeptides may be produced by expression in a suitable prokaryotic or eukaryotic system. For example, part or all of a DNA molecule, such as the cDNAs having SEQ ID NOs: 1-6, may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The dehydrins or LEA proteins produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The dehydrins and LEA proteins of the invention, prepared by the aforementioned methods, may be analyzed according to standard procedures.

Dehydrins and LEA proteins purified from coffee or recombinantly produced, may be used to generate polyclonal or monoclonal antibodies, antibody fragments or derivatives as defined herein, according to known methods. Antibodies that recognize and bind fragments of the dehydrins or LEA proteins of the invention are also contemplated, provided that the antibodies are specific for dehydrins or LEA proteins. For example, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

The dehydrins, and likely the LEA proteins as well, are involved in protecting cellular components from osmotic stresses (dehydration, low temperatures/freezing, salt). Accordingly, the coffee dehydrins and LEA proteins described and exemplified herein are expected to find utility in a variety of food and cosmetic applications. For example, the dehydrins or LEA proteins may be utilized to alter ice nucleation in frozen foods, or to facilitate the drying of proteins in a manner that enables rapid rehydration at a later stage. As another example, the dehydrins or LES proteins may be utilized for in hydrating skin cream products. In addition, the recently discovered antioxidant and ion-binding properties of dehydrins may prove advantageous in both food and cosmetic products. In connection with food applications, it is noteworthy that the dehydrins are highly soluble, very unstructured protein and they are not known to have disulfide bonds. As a result, these proteins are likely exhibit very low antigenicity and will likely be easily digested by proteases in the gut.

One or more of the aforementioned applications for the dehydrins or LEA proteins may be pursued by exploiting the availability of the dehydrin- and LEA protein-encoding polynucleotides described herein to generate significant quantities of pure protein using recombinant organisms (e.g., in the yeast Picia pastoris or in food compatible Lactobacilli, or in plant cells), and then testing the proteins in already established assays for ice formation, effects on drying, rehydration, and antioxidant potential. If specific purified proteins were found to be particularly useful, natural versions of those proteins also may be isolated from coffee grains determined to be rich in those particular dehydrins or LEA proteins.

Vectors, Cells, Tissues and Plants:

Also featured in accordance with the present invention are vectors and kits for producing transgenic host cells that contain a dehydrin- or LEA protein-encoding polynucleotide or oligonucleotide, or homolog, anaolog or variant thereof in a sense or antisense orientation, or a reporter gene and other constructs under control of dehydrin or LEA protein-encoding gene promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a dehydrin- or LEA protein-encoding gene, or nucleic acid sequences that inhibit the production or function of a plant's endogenous dehydrins or LEA proteins. This is accomplished by transforming plant cells with a transgene that comprises part of all of a dehydrin or LEA protein coding sequence, or mutant, antisense or variant thereof, including RNA, controlled by either native or recombinant regulatory sequences, as described below. Transgenic plants coffee species are preferred, including, without limitation, *C. abeokutae, C. arabica, C. arnoldiana, C. aruwemiensis, C. bengalensis, C. canephora, C. congensis C. dewevrei, C. excelsa, C. eugenioides, and C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Can berra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, a dehydrin or LEA protein coding sequence under control of its natural 5' and 3' regulatory elements is utilized. In other embodiments, dehydrin or LEA protein coding and regulatory sequences are swapped (e.g., CcLEA1 coding sequence operably linked to CcDH2 promoter) to alter the water or protein content of the seed of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants expressing dehydrin or LEA protein coding sequences under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g., hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name only a few.

Tissue specific and development-specific promoters are also contemplated for use in the present invention, in addition to the seed-specific dehydrin or LEA protein promoters of the invention. Non-limiting examples of other seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta-phaseolin, napin, beta-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the oleosin gene promoter described in commonly-owned, co-pending PCT Application No. [NOT YET ASSIGNED]. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), Bromoxynil nitrilase (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be expressed in coffee plants in order that the proteins may play a role in stress tolerance in the plant, and in the enhancement of flavor and/or aroma of the coffee beverage or coffee products ultimately produced from the bean of the coffee plant expressing the protein.

With respect to stress tolerance, it is now well established that dehydrin proteins participate in protecting plants from osmotic or environmental stresses such as dehydration and freezing (Allagulova et al., 2003). For example, dehydrins play a role in water retention and osmotic regulation to protect the plant against the loss of water, especially in drought conditions. Furthermore, given that dehydrins exhibit the capacity to interact with cations, dehydrin proteins may serve to bind excess salts during periods of limited water, and may serve a chelating function. Dehydrins also play a role in the structural integrity of nuclear material such as chromatin during cell desiccation in the developing seed, and have been found to play a role in protection against ice crystal formation and starch degradation in freezing temperatures. The function of a given dehydrin protein may be related to the location of the protein within the cell. For example, dehydrins localized to the exterior of the cell membrane may serve to stabilize lipids and membrane proteins. (Allagulova et al., 2003). Therefore, the ability to manipulate dehydrin or LEA protein production in a plant, or even to use the polynucleotides and proteins of the invention to monitor such gene expression, will enable study and manipulation of drought, cold or salt, i.e., osmotic tolerance in coffee. Such manipulation may extend from the germinating seedling to the growing plant and developing fruit and seeds, to the post-harvest storage stability of coffee beans. This knowledge enables the generation of modified coffee plants that are better equipped for healthy growth and crop production under conditions of acute or prolonged osmotic or environmental stresses such as those encountered under dry periods, drought, frost, or prolonged freezing conditions. Thus, one aspect of the invention features methods to protect plants, preferably coffee plants, by enhancing osmotic stress resistance by modulating the expression of dehydrins or LEA proteins in the plant.

With respect to flavor and aroma of roasted coffee grain, it is expected that the dehydrins and related LEA proteins exert some influence on the generation of coffee flavors via the Maillard reaction that occurs during roasting. Proteins, and particularly protein degradation products (peptides and amino acids), represent an important group of flavor precursors (Spanier et al., 2004). Therefore, relatively abundant proteins such as the dehydrins and LEA proteins can be expected to make some contribution to the flavor generating reactions that occur during coffee roasting. In this context, it is possible that these relatively unstructured, and very hydrophilic and highly soluble proteins react differently from other cellular proteins during a Maillard reaction, either due to their unusual structure, and/or due to their unusual interaction(s) with water molecules. It is well known that the levels of water present during cooking reactions, such as the roasting step of coffee, can also strongly influence the pathway(s) of heat induced chemical reactions (Turner et al., 2002). Because the dehydrins contribute to the organization of water molecules in the grain, a variety of specific differences in the levels and distribution of the dehydrins could influence the development of flavor during the roasting process. The ability to monitor (e.g., through marker-assisted breeding) or manipulate dehydrin and LEA protein expression profiles is provided by the polynucleotides of the present invention, in accordance with the methods described herein.

Thus, one aspect of the present invention features methods to alter the dehydrin or LEA protein profile in a plant, preferably coffee, comprising increasing or decreasing an amount or activity of one or more dehydrins or LEA proteins in the plant. For instance, in one embodiment of the invention, a dehydrin-encoding gene under control of its own expression-controlling sequences is used to transform a plant for the purpose of increasing production of that dehydrin in the plant. Alternatively, a dehydrin or LEA protein coding region is operably linked to heterologous expression controlling regions, such as constitutive or inducible promoters.

The organization of water molecules or the stabilization or macromolecules or organelles in the grain of a plant may also be altered by decreasing production of one or more dehydrins or LEA proteins in the plant, or by screening naturally-occurring variants for decreased dehydrin or LEA protein expression. For instance, loss-of-function (null) mutant plants may be created or selected from populations of plant mutants currently available. It will also be appreciated by those of skill in the art that mutant plant populations may also be screened for mutants that over-express a particular dehydrin, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135(2): 630-636; Gilchrist & Haughn, 2005, Curr. Opin. Plant Biol. 8(2): 211-215). The methods to make mutant populations are well known in the art.

The nucleic acids of the invention can be used to identify dehydrin or LEA protein mutants in various plant species. In species such as maize or *Arabidopsis*, where transposon insertion lines are available, oligonucleotide primers can be designed to screen lines for insertions in the dehydrin or LEA protein genes. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected dehydrin or LEA protein to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al., 1997, Genetics 145: 163-171; Kolch et al., 1991, Nature 349: 426-428).

Another kind of transgenic null mutant can be created by inhibiting the translation of dehydrin- or LEA protein-encoding mRNA by "post-transcriptional gene silencing." The dehydrin- or LEA protein-encoding gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, Proc. Natl. Acad. Sci. U.S.A. 95: 13959-13964). In this regard, dsRNA containing sequences that correspond to part or all of at least one intron have been found particularly effective. In one embodiment, part or all of the dehydrin or LEA protein coding sequence antisense strand is expressed by a transgene. In another embodiment, hybridizing sense and antisense strands of part or all of the dehydrin or LEA protein coding sequence are transgenically expressed.

In another embodiment, dehydrin or LEA genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, Differentiation 72: 65-73; Baulcombe, 2004, Nature 431: 356-363; Herr, 2004, Biochem. Soc. Trans. 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by an common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, Plant J. 16(6): 651-659). Plant cells are transformed with a copy of the endogenous gene targeted for repression. In many cases, this results in the complete repression of the native gene as well as the transgene. In one embodiment, a dehydrin- or LEA protein-encoding gene from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of dehydrins and LEA proteins in flavor, aroma and other features of coffee seeds associated with water content and organization. Plants containing one transgene or a specified mutation may also be crossed with plants containing a complementary transgene or genotype in order to produce plants with enhanced or combined phenotypes.

The present invention also features compositions and methods for producing, in a seed-preferred or seed-specific manner, any selected heterologous gene product in a plant. A coding sequence of interest is placed under control of a seed-specific coffee dehydrin or LEA protein promoter or other seed-specific promoter and other appropriate regulatory sequences, to produce a seed-specific chimeric gene. The chimeric gene is introduced into a plant cell by any of the transformation methods described herein or known in the art. These chimeric genes and methods may be used to produce a variety of gene products of interest in the plant, including but not limited to: (1) detectable gene products such as GFP or GUS, as enumerated above; (2) gene products conferring an agronomic or horticultural benefit, such as those whose enzyme activities result in production of micronutrients (e.g., pro-vitamin A, also known as beta-carotene) or antioxidants (e.g., ascorbic acid, omega fatty acids, lycopene, isoprenes, terpenes); or (3) gene products for controlling pathogens or pests, such as described by Mourgues et al., (1998), TibTech 16: 203-210 or others known to be protective to plant seeds or detrimental to pathogens.

Moreover, certain of the dehydrin or LEA-gene promoters can be used to produce recombinant proteins in both the seeds and in siliques. In addition, given that certain of the dehydrin genes are also activated under drought and other stress conditions. these promoters should prove useful to direct gene expression in other tissues, such as mature leaves, when they are osmotically stressed. This latter feature indicates that it is feasible to use these promoters to express recombinant proteins specifically in the leaves of plants (for example tobacco) at the end of maturation as they undergo senescence and begin to dry.

It is believed that the dehydrins are part of a plant's defense against dehydration. Therefore, the induction of the CcDH1 and CcDH2 genes can be used as a measure of dehydration stress existing in a plant; both the time of induction of the water stress as well as the level of water stress. Thus, dehydrin expression can be used to screen populations of plants for their osmotic stress response capabilities.

The following examples are provided to describe the invention in greater detail. The examples are intended illustrate, not to limit, the invention.

Example 1

Plant Material for RNA Extraction

Freshly harvested roots, young leaves, stems, flowers and fruit at different stages of development were harvested from *Coffea arabica* L. cv. *Caturra* T-2308 and *Coffea canephora* var. *BP*409 grown under greenhouse conditions (25° C., 70 RH) and also from *Coffea canephora* BP-409 grown in the field in East Java, Indonesia. The development stages are defined as follows: small green fruit (SG), large green fruit (LG), yellow fruit (Y) and red fruit (R). Fresh tissues were frozen immediately in liquid nitrogen, then stored at −80° C. until used for RNA extraction.

Example 2

Protocols for Extraction of Total RNA, Generation of cDNA, and PCR Reaction Conditions The tissue samples stored at −80° C. were ground into a powder and total RNA was extracted from this powder using the method described previously (Rogers et al. 1999). Samples were treated with DNase using the kit "Qiagen RNase-Free DNase" according to the manufacturer's instructions to remove DNA contamination. All RNA samples were analysed by formaldehyde agarose gel electrophoresis and visual inspection of the ribosomal RNA bands upon ethidium bromide staining. Using oligo ($dT_{20}$) as a primer, cDNA was prepared from approximately 4 µg total RNA according to the protocol in the Superscript II Reverse Transcriptase kit (Invitrogen, Carlsbad, Calif.). To test for the presence of contaminating genomic DNA in the cDNA preparations, a primer pair was designed spanning a known intron of a specific ubiquitously expressed cDNA, chalcone isomerase. The absence of the genomic fragment in the PCR reactions indicated the absence of detectable genomic DNA contamination. The PCR reactions were carried out using the *Coffea arabica* and *Coffea canephora* cDNA prepared as described above. The gene-specific primers are set forth in Table 1.

TABLE 1

List of primers used for RT-PCR and quantitative RT-PCR

| Oligo name (SEQ ID NO.:) | 5'--> 3'Sequence | Oligo name | 5'--> 3' Sequence |
|---|---|---|---|
| Rpl39_forward (SEQ ID NO.: 23) | TGGCGAAGAAGCAGAGGCAGA | LEA1_forward (SEQ ID NO.: 31) | CCAATAACAGCTCAAGAATCA |
| Rpl39_reverse (SEQ ID NO.: 24) | TTGAGGGGGAGGGTAAAAAG | LEA1_reverse (SEQ ID NO.: 32) | TTCCCTTCCATCCCACTCT |

TABLE 1-continued

List of primers used for RT-PCR and quantitative RT-PCR

| Oligo name (SEQ ID NO.:) | 5'--> 3'Sequence | Oligo name | 5'--> 3' Sequence |
|---|---|---|---|
| DH1_forward (SEQ ID NO.: 25) | GAAGAAGGGGATGAAGGAG | rpl39-F1 (SEQ ID NO.: 33) | GAACAGGCCCATCCCTTATTG |
| DH1_reverse (SEQ ID NO.: 26) | TACGGACAAACACACTACAG | rpl39-R1 (SEQ ID NO.: 34) | CGGCGCTTGGCATTGTA |
| DH2_forward (SEQ ID NO.: 27) | CCTCCAACAACCACCACTG | rpl39-MGB (SEQ ID NO.: 35) | ATGCGCACTGACAACA |
| DH2_reverse (SEQ ID NO.: 28) | TCAAGCGCACAACAAGGTC | DH2a-F1 (SEQ ID NO.: 36) | GGGAGGCACAAGGACAGAGA |
| DH3_forward (SEQ ID NO.: 29) | AGGTGGTGGTCAGAAGAAGAC | DH2a-R1 (SEQ ID NO.: 37) | GCTGTGCGCGTGCTGAT |
| DH3_reverse (SEQ ID NO.: 30) | GACACACTGGAAAGCTGCTA | DH2a-MGB (SEQ ID NO.: 38) | CAGGAGCACATCGAT |

PCR reactions (50 μL) were set up containing 10 μL of a one hundred-fold dilution of the cDNAs, except for CcDH2 where 10 ul of a one thousand-fold dilution of the cDNA set was used. 1 μM each primer, 5 μL of 10× ThermoPol Buffer (New England Biolabs Beverly, Mass.), 1 μL of DMSO, 200 μM of dNTPs and 2 units of Taq polymerase (New England Biolabs Beverly, Mass.). The cycling conditions were 2 min at 94° C., 35 cycles (except for CcDH1 where 40 cycles was used) of 94° C. for 1 min, 60° C. for 1 min and 72° C. for 1.5 min. The final extension step was for 7 min at 72° C. The RT-PCR products were resolved on 2% (w/v) agarose gels and stained with ethidium bromide. The CcRL39 gene, which encodes the constitutively expressed coffee L39 protein (a 60S ribosomal large subunit protein) was used as a semi-quantitative control to verify that each RNA sample was transcribed into cDNA at relatively similar efficiencies. Amplification of the RPL39 gene was used as a positive control for the reverse transcription with the primers shown in Table 1.

Quantitative TaqMan-PCR of CcDH2 and CcRPL139 was carried out according to the manufacturer's protocol (Applied Biosystems, Perkin-Elmer) using the *Coffea arabica* and *Coffea canephora* cDNA and the TaqMan probes shown in Table 1. 25 μL reactions containing 12.5 μL of TaqMan® Universal Master Mix 2×, 20 nM of TaqMan®-MGB probe, 80 nM of TaqMan® specific primers and 5 μL of the 1000 fold diluted cDNAs. The cycling conditions were 50° C. for 2 minutes, 95° C. for 10 minutes, then 40 cycles of 94° C. for 15 seconds, and 60° C. for 1 minute. Each reaction was repeated 3 times. The expression of the DH2 gene in each cDNA sample was normalized to the expression of the RPL39 gene in the same sample.

Example 3

Protocol for Isolation of DH2 Promoter Region

The promoter sequence of CcDH2 was isolated using the Genome Walker kit according to the manufacturer's specifications (BD Sciences-Clontech). Genomic DNA was isolated from *Coffea canephora* var. BP409 as described (Crouzillat et al., 1996). The CcDH2 specific forward Genome Walker primer used was: DH2a primer1-5' TGTGCTCCTGAT-GCTCTCTGTCCTTGTGC 3' (SEQ ID NO.:39). An approximately 2.1 kb fragment was isolated using HindIII-digested *Coffea canephora* var. BP409 genomic DNA ligated to the Genome Walker adaptor sequence. PCR amplification was carried out in a 50 ul reaction using the Clontech Advantage 2 PCR kit according to the manufacturer's protocol using 0.5 uM final concentrations of DH2a primer1 and the Genome Walker AP1 primer. The PCR reaction was carried out with following conditions: 94° C. for 2 seconds and 72° C. 3 minutes (7 cycles), 94° C. for 2 seconds and 67° C. 3 minutes (32 cycles), followed by 4 minutes at 67° C. The major PCR fragment obtained was then cloned into the plasmid pCR4-TOPO (Invitrogen).

A plasmid pJMc1 containing the appropriate insert was purified and its insert was completely sequenced. To verify that the inserts in pJMc1 and (pcccs30w8a4) were from the same gene, the corresponding overlapping sequence of these two clones was re-amplified from genomic DNA using the primers DH2a geneup 5' ATAGTGACCTTAATAGCGATCT-TGTTGC 3' (SEQ ID NO.:40) and DH2a genelow 5' CCAAATCAAATCAAACCAAGCAAATC 3' (SEQ ID NO.:41). The PCR reaction was performed with *Coffea canephora* var. BP409 genomic DNA and using Taq (New England Biolabs) and 1 uM of the specific primers (DH2a geneup and DH2a genelow). The PCR reaction was carried out with the following conditions: 94° C. 1 minute, then 35 cycles of 94° C. 1 minute, 58° C. 1.5 minutes, and 72° C. 3 minutes, followed by 7 minutes at 72° C. The main PCR fragment produced was then cloned into pCR4-TOPO. A plasmid pVC1 (FIG. 7) containing the appropriate insert was purified and its insert was completely sequenced. There were 5 base changes between the genomic fragments of pJMc1 and pVC1. One change was in the promoter region, two changes were in the intron, and two changes were in the protein coding sequence. Of these changes in the protein coding sequence, one change was neutral, the other resulted in a different amino acid.

Example 4

Southern Blot Protocol

Genomic DNA was prepared as described previously (Crouzillat et al., 1996). Five micrograms of genomic DNA from *C. canephora* BP 409 DNA was digested overnight with the appropriate enzymes (10 U/ug) according to the supplier's recommendations and the products were separated on 0.8% agarose gels. Southern blotting and hybridizations were carried out as described previously (Crouzillat et al., 1996). The probe was generated by first PCR amplifying the insert of the CcDH2 clone cccs30w8a4 with the primers T3+T7. This PCR product was then labeled with [32P]dCTP using the "Rediprime™ II random prime labeling system" kit (Amersham).

Example 5

Identification and Characterization of Coffee Dehydrin cDNA

More than 47,000 EST sequences were generated from several coffee libraries made with RNA isolated from young leaves and from the grain and pericarp tissues of cherries harvested at different stages of development. Overlapping ESTs were subsequently "clustered" into "unigenes" (i.e., contigs) and the unigene sequences were annotated by doing a BLAST search of each individual sequence against the NCBI non-redundant protein database. The unigenes were screened for dehydrin sequences using various approaches, including a search of the unigene annotations with the keyword "dehydrin" and by using various *Arabidopsis* and tomato dehydrin protein sequences in a tBlastn search of the coffee unigene set. The various search protocols yielded several candidate dehydrin unigenes, and the potentially longest cDNA clone for each of these unigenes was isolated from the library and completely sequenced (Table 2).

encode the ORF for CcDH2. Unigene #123405 (CcDH2b) is composed of 2 ESTs and differs from the unigene sequence #123406 (CcDH2a) by the presence of an intron sequence. When the intron/exon borders of the cDNA for DH2b (cccs46w30p1) were examined in more detail, it was observed that the 3' junction had the sequence ttatgg/TCG while other genomic sequences obtained by genome walking (see below) had the sequence ttatag/T(A)CGG. Overall, the intron sequences of the cDNA cccs46w30p1 and the intron sequences in the genomic DNA were nearly identical. Because none of the single base changes appeared in all three of the genomic intron sequences available, it appears that an alteration of the 3' splice site sequence of CcDH2b may be the cause of the aberrant splicing of this cDNA. The 756 bp cDNA pcccs30w8a4 (CcDH2a) encodes a protein of 162 amino acids long with the predicted molecular weight of 17.4 kDa. One unigene was found for CcDH3 (#123385). The protein sequence encoded by CcDH3 demonstrates that this 833 bp cDNA encodes a protein of 227 amino acids with the predicted approximate molecular weight of 25.1 kDa.

Figure 1:
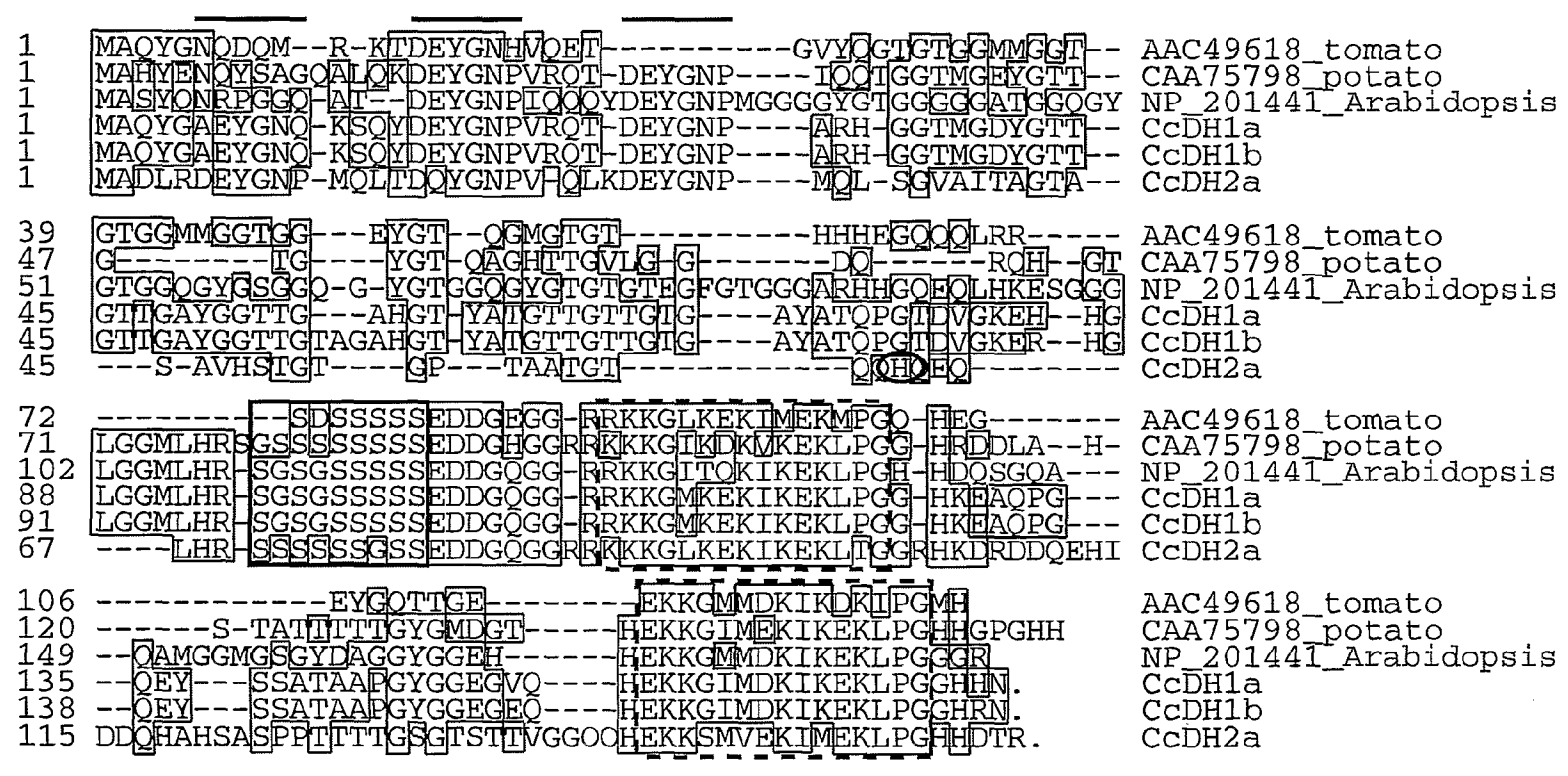

The protein sequences of the coffee dehydrins were aligned with the most homologous protein sequences found in the non-redundant protein database and also analyzed for the presence of the dehydrin specific amino acid motifs Y, S, and K. FIGS. 1 and 2 show that the three dehydrins fall into two classes, with CcCDH1a, CcDH1b and CcDH2a having the structure $Y_3SK_2$ and CcDH3 having the structure $SK_3$. Of those protein sequences with the $Y_3 SK_2$ structure, CcDH1a and CcDH1b show absolute conservation in each of the three motifs, as well as in the two conserved regions that proceed

TABLE 2

Full length *Coffea canephora* cDNA encoding dehydrin and LEA proteins and the number of ESTs found for each sequence. Unigene numbers and the molecular weights are given in parentheses for each plasmid: cccl26i7 (Unigene 121870; 17.8 kDa); cccs30w27m8 (Unigene 121870; 18.1 kDa); cccs30w8a4 (Unigene 123406; 17.4 kDa); cccs46w30p1 (Unigene 123405; 17.4 kDa); cccwc22w11a5 (Unigene 123385; 25.1 kDa); Dav1-59 (Unigene 119994; 39.5 kDa).

| Plasmid name | Gene name | Structure | In silico expression (number of ESTs in libraries) | | | | | | |
|---|---|---|---|---|---|---|---|---|---|
| | | | Whole cherries 22 weeks | Grain 18 weeks | Grain 30 weeks | Grain 42 weeks | Grain 46 weeks | Pericarp | Leaf |
| cccl26i7 | CcDH1a | $Y_3SK_2$ | | 1 | 6 | | 18 | | 18 |
| cccs30w27m8 | CcDH1b | | | | | | | | |
| cccs30w8a4 | CcDH2a | $Y_3SK_2$ | | | 20 | | 3 | | 1 |
| cccs46w30p1 | CcDH2b | | | | 1 | | 1 | | |
| cccwc22w11a5 | CcDH3 | $SK_3$ | 2 | | | | 7 | | 3 |
| Dav1-59 | CcLEA1 | LEA protein | | | | 22 | | | |

DNA sequence analysis of the selected full length cDNA clones revealed four unique sequences representing three different dehydrin genes. The corresponding genes were named CcDH1, CcDH2, and CcDH3. Two apparently allelic sequences of the gene CcDH1 were identified by sequencing two of the longest cDNA in unigene #121870. The cDNA clones CcDH1a and CcDH1b were 836 and 896 bp long respectively. The two ORF sequences exhibited 5 single base changes, and CcDH1b had an insertion of 9 bases. These differences translated into six amino acid differences. CcDH1a and CcDH1b encode proteins of 172 amino acids and 175 amino acids which have predicted molecular weights of approximately 17.8 kDa and 18.1 kDa, respectively. Two distinct unigenes, #123406 and #123405, were found to each of the two K motifs. This observation, and the fact that the small sequence differences that exist occur in the least conserved regions of the aligned sequences, is consistent with the idea that CcDH1a and CcDH1b are allelic. In contrast, CcDH2a is clearly different from CcDH1. While CcDH2a has the structure $Y_3SK_2$, it also exhibits punctual differences in all but one of the Y, S and K motifs, as well as more significant differences outside these dehydrin specific motifs. The CcDH1 and CcDH2 encode proteins with calculated pI that are near neutral, and their hydrophilicity plots indicate that these proteins are very hydrophilic throughout. The calculated pI of the protein encoded by CcDH3 is slightly acidic (5.47), and this protein is also very hydrophilic, as shown by the Kyte-Doolittle hydrophilicity plot in FIG. 8.

Example 6

Characterization of a cDNA Encoding a Coffee LEA Protein

A cDNA library was constructed from RNA prepared from coffee grain 30 weeks after fertilization. From this library, a full length cDNA clone (Dav1-59) encoding an LEA protein was isolated and sequenced. This cDNA clone was renamed CcLEA1. In addition, the EST database was searched for "unigenes" annotated as LEA proteins. This search produced 9 unigene sequences, one of which (unigene #119994) corresponded to the previously isolated sequence of CcLEA1. (Table 3). The EST analysis indicated that CcLEA1 is strongly and exclusively expressed during only one period of grain development (30 weeks after flowering).

TABLE 3

*Coffea canephora* unigene sequences annotated as LEA proteins

| | | In silico expression (number of ESTs in libraries) | | | | | | |
|---|---|---|---|---|---|---|---|---|
| Unigene name | Number of ESTs | Whole cherries 22 weeks | Seed 18 weeks | Seed 30 weeks | Seed 42 weeks | Seed 46 weeks | Pericarp | Leaf |
| 124784 | 26 | | | 17 | | 9 | | |
| 124426 | 26 | | | | | 9 | | 17 |
| 119994 | 22 | | | 22 | | | | |
| 124428 | 10 | 1 | | | | 3 | 4 | 2 |
| 121426 | 8 | | 1 | 5 | | 2 | | |
| 124123 | 5 | 3 | | | | | 1 | 1 |
| 120926 | 2 | | | | | 2 | | |
| 131122 | 1 | | | | | 1 | | |
| 127677 | 1 | | | | | 1 | | |

Figure 3:
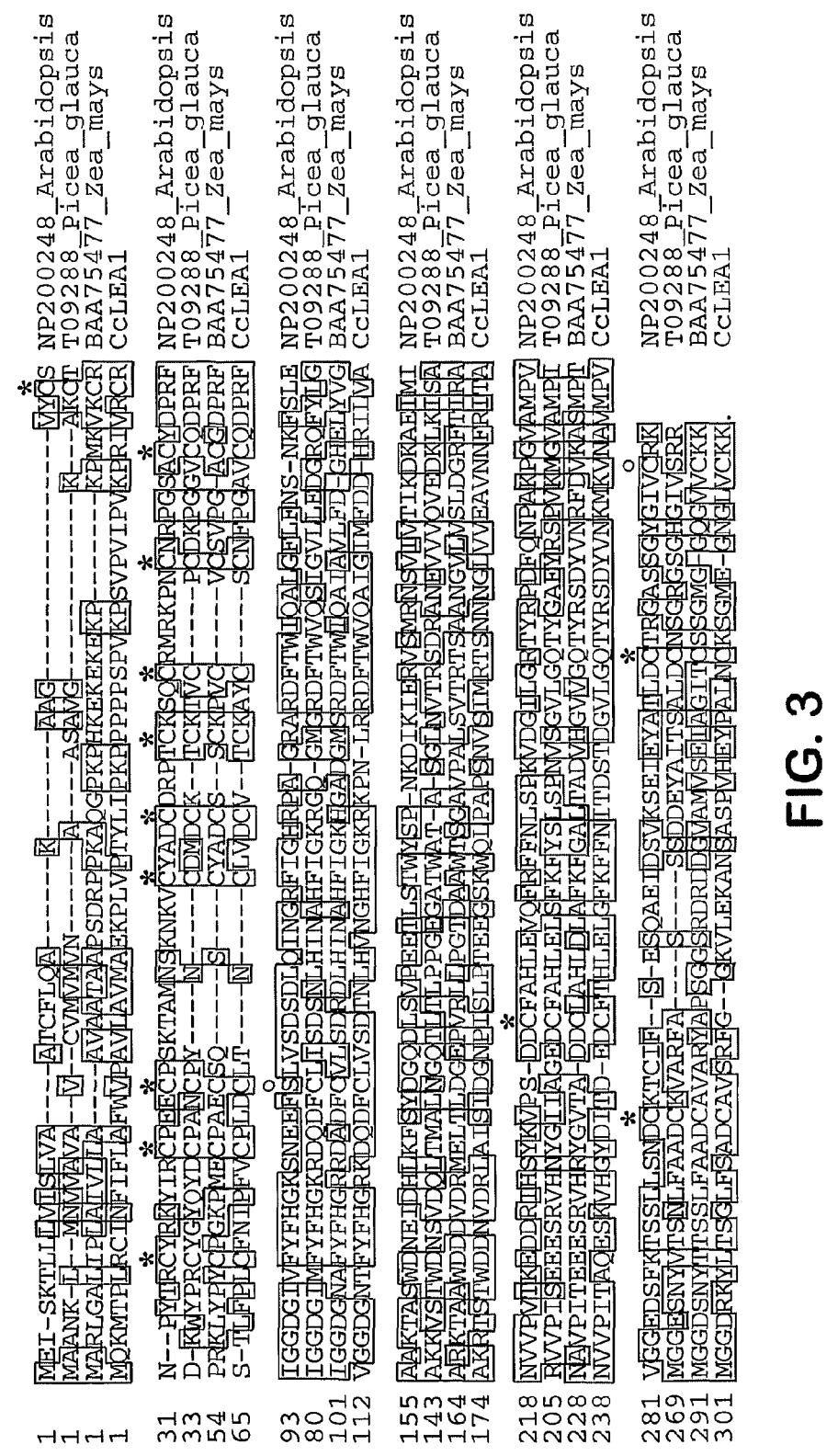

The protein encoded by CcLEA1 is 358 amino acids and has a predicted molecular weight of 39.5 kDa. The calculated pI for CcLEA1 is slightly basic (8.17), and a hydrophilicity plot shows that while this protein does not have significant regions of hydrophobicity, it is less hydrophilic than the three coffee dehydrins. The first 30 N-terminal residues of CcLEA1 form one of two small hydrophobic regions in this protein. FIG. 3 shows the alignment of CcLEA1 with the 3 most homologous sequences found in the non-redundant Genbank protein database. The overall identity values of these aligned sequences only ranged from 34.7% for the *Arabidopsis* sequence to 47.9% for the *Picea* (white spruce) sequence. However, there are short, highly conserved regions in these proteins. All of the related protein sequences had relatively similar hydrophilicity profiles to CcLEA1, and generally, the most significant hydrophobic patch of the proteins could be found in the N-terminal 1-25 amino acids. CcLEA1 was also found to contain a proline rich segment in the N-terminal region, which is absent from the other proteins in FIG. 3.

Example 7

RT-PCR Expression of CcDH1, CcDH2, CcDH3 and CcLEA-1 Genes in Different Coffee Tissues and During Coffee Grain Development Because the EST libraries were not normalized, and were deeply sampled, the number of ESTs found in each unigene gives a rough estimation of the expression level of that gene in each tissue sampled. Table 2 (above) shows that CcDH1 and CcDH2 are strongly expressed in the grain at 30 and 46 weeks after fertilization, but were not detected in the pericarp library, nor were they detected in whole cherries (developing grain+pericarp) at 22 weeks after fertilization. Both CcDH1 and CcDH2 are expressed in the leaf, although CcDH1 may be expressed in young leaf at a higher level than CcDH2. Expression of CcDH3 was detected in the grain at 46 weeks after fertilization, and in the young leaf, although 2 ESTs were also observed in the 22 week whole cherry samples.

To extend the expression data, RT-PCR analysis was carried out for each of the three coffee dehydrin genes. The results of this analysis are shown in FIG. 4. CcDH1 was expressed significantly in arabica grain at all the stages examined, and in the three last stages examined for robusta. CcDH1 expression could also be detected in other tissues tested, although no signal was detected for arabica in the small green pericarp and yellow pericarp samples, or for robusta in the root or leaf samples. Among the tissues having expression of CcDH1, the arabica flower sample appeared to have the highest level of transcripts.

Figure 5:
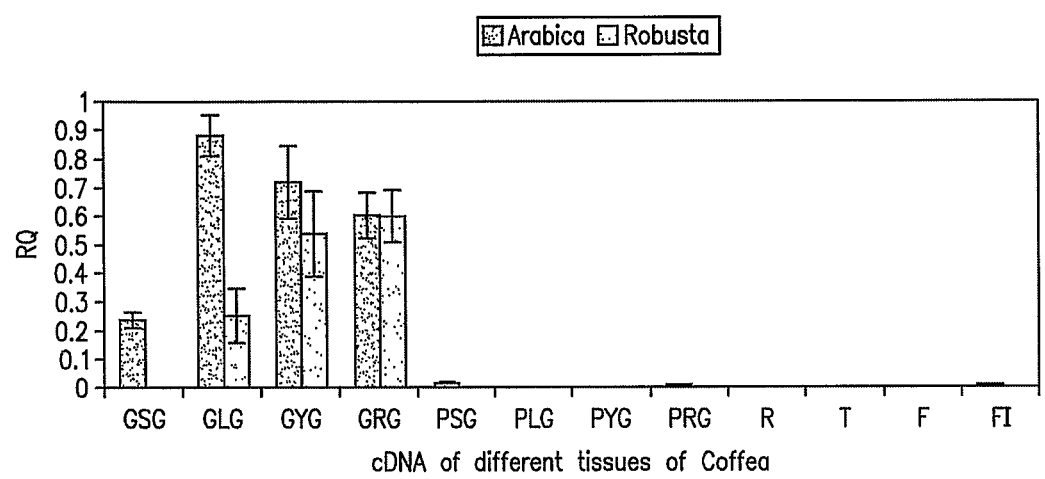
FIG. 5. Quantitative RT-PCR expression analysis of CcDH2 in different organs of *Coffea canephora* and *Coffea arabica*. GSG, GLG, GYG, GRG represent small green, large green, yellow and red grain respectively; PSG, PLG, PYG, PRG represent small green, large green, yellow and red pericarp respectively; R, S, L, F represents root, stem, leaves and flowers. The standard deviations are reported on the graph for each reaction.

A relatively high level of CcDH2 transcripts was detected in all the grain development stages of arabica and the last three stages of the robusta grain (FIG. 4). In contrast to CcDH1, no CcDH2 transcripts were detected by RT-PCR in the other tissues studied. The absence of significant levels of CcDH2 transcripts in tissues other than the grain, as well as the later induction of this gene in robusta, was confirmed by TaqMan quantitative RT-PCR (FIG. 5). The expression of CcDH2 was compared to the constitutively expressed transcript of the CcRPL39 gene (RPL39 encodes large ribosomal subunit protein #39). The comparison demonstrated that the expression of CcDH2 increased gradually in robusta, beginning from the large green stage up to the mature red stage. In contrast, the quantitative RT-PCR data for arabica showed that the highest level of CcDH2 transcripts was detected at the large green stage and that the transcript levels fell somewhat as maturation progressed.

RT-PCR analysis of CcDH3 gene expression demonstrated that significant levels of these transcripts were also detected in all the arabica grain samples, as well as in the last three stages of robusta grain development (FIG. 4). The levels of CcDH3 transcripts in some of the other tissues, such as the red pericarp, stem, and flowers, were nearly as high as in the grain. Examination of the original data showed that CcDH3 transcripts could be detected in all of the other arabica and robusta tissues examined. However, a significant difference is noted between the transcript levels for the first three pericarp stages of robusta and arabica.

The expression of CcLEA1 was also evaluated by RT-PCR. The data obtained confirms that this gene has a very unique expression pattern, with transcripts being detected only in the small green stage of arabica and the large green stage of robusta grain (FIG. 4). No expression was detected in any of the other arabica or robusta tissues sampled. This data is consistent with the distribution pattern of ESTs for this gene seen in Table 3, which indicates that this gene is expressed in robusta grain at 30 WAF but not in any other grain, cherry, pericarp, or leaf EST libraries.

Example 8

Sequence Analysis of the CcDH2 Promoter

Figure 6:
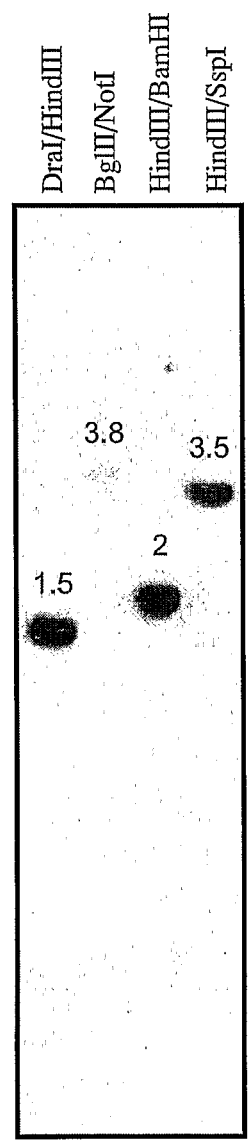
FIG. 6. Southern blot analysis of CcDH2 dehydrin. The autoradiogram was exposed for three days.

CcDH2 is a moderately expressed, grain specific gene. Southern blotting was carried out to determine if the level of expression was obtained from a gene with a single/low copy number or a multicopy gene. As shown in FIG. 6, each digestion produced only one band, suggesting that CcDH2 is likely to be encoded by a single gene in the *C. canephora* genome.

The technique of primer walking was used to isolate a genomic fragment incorporating the CcDH2 promoter. PCR amplification of the DNA was carried out using a CcDH2 specific Genome Walker primer designed from the center of the cDNA cccs30w8a4 (DH2a primer 1), and the AP1 primer of the Genome Walker kit. A 2.1 kb genomic fragment that stretched 1.43 kb upstream of the cccs30w8a4 cDNA sequence (*C. canephora*) was generated and cloned. Sequence analysis of the composite sequence obtained from the overlapping plasmids containing both genomic and cDNA sequences showed that the CcDH2 gene contains a single intron (231 bp) located within the ORF region (FIG. 7). Further analysis of the promoter region of this gene indicates the presence of a putative TATA sequence 30 bp upstream of the 5' end of the cDNA sequence.

Several potential regulatory elements previously shown to be involved in the regulation of gene expression during seed development were also identified in the 5' upstream region of the CcDH2 gene. For example, three regions with similarity to the *Arabidopsis* ABA responsive element RYACGTGGYR (SEQ ID NO:42) were found. Two elements were found that shared significant similarity with the RY repeat (CATGCA (T/a)(A/g) of the core region in the "legumin" box that is involved in regulating the expression of legumin type storage proteins. The presence of two dehydration-responsive element/C-Repeat (DRE/CRT) cis-acting sequence motifs (G/ACCGAC) were also identified. The DRE/CRT motifs have been shown previously to interact with DREBs/CBF transcription factors to control the response of linked genes to dehydration and other stresses in *arabidopsis* and rice. (Dubouzet J G, Plant J. 33: 751-763 (2003)). In addition, several E-box motifs (CANNTG), which are well defined components in storage protein promoters such as the 2S protein, (Chatthai M, Plant Physiol Biochem 42: 417-423 (2004)), were identified in the CcDH2 promoter region.

Example 9

Functional Analysis of the Coffee Dehydrin Promoter CcDH2 in *Arabidopsis thaliana*

Expression in *Arabidopsis thaliana* of a reporter gene encoding beta-glucuronidase (GUS), under control of the CcDH2 promoter, was examined.
Materials and Methods:
The dehydrin DH2 promoter sequence from pVC1 was amplified using the polymerase Pfu1 under the conditions described by the supplier (Stratagene) and the primers:

```
                                        (SEQ ID NO,: 43)
TG - TG698    ttgaagcttGTGGACATGACGGAAGAGGT
and (SEQ ID NO,: 44)
TG - TG743    gcagatctaccatggAGGACTCCTGTTATTAGAAAA.
```

The PCR fragment thus obtained was then cut with HindIII and BglII and cloned into the HindIII/BglII sites of the plant transformation vector pCAMBIA1301. This places the approximately 1.3 kb fragment containing the dehydrin promoter sequence and the complete 5' untranslated region of the dehydrin cDNA (approximately 80 bp) within 2 bp of the ATG for the GUS (first exon of GUS). The correct positioning of the promoter was verified by sequencing. The new dehydrin CcDH2 promoter containing vector was named pCAMBIA1301UCD2.4

Plant Transformation.
The transformation vector pCAMBIA1301UCD2.4 was then transformed into *Agrobacterium tumefaciens* strain EHA105 using standard procedures. The hygromycin resistance gene, driven by a 2×35S promoter, was the plant selectable marker in pCAMBIA1301. *Agrobacterium tumefaciens* mediated transformation of *Arabidopsis* (with the plasmid pCAMBIA1301UCD2.4) was performed by floral-dip method (Clough and Bent, 1998).

Transformed plants were identified by plating seed on 0.8% agar containing 1 mM sodium nitrate and 50 µg perml hygromycin. Transformed seedlings were identified 7 days after plating as plants with an extended primary root. Seedlings were transferred to 0.8% agar containing 0.5×M&S salts. Plants were thereafter transferred to soil when the second leaf pair developed, and allowed to mature and set seed (T1). In some cases, the T1 seeds were germinated, and then allowed to grow and to set seeds (T2).

GUS Staining.
The seedlings and siliques examined for GUS staining were either from T1 or T2 seeds, and were at different stages of development. The GUS staining solution was prepared by dissolving 5 mg X-Gluc in 50 µl dimethyl formamide, and then adding this to 10 ml 50 mM $NaPO_4$ pH 7.0. With a fine forceps, the seedlings were transferred from the germination plates into a 1.5 ml microfuge tube containing 1.0 ml of GUS stain. The tubes were transferred to a desiccator and placed under vacuum for 10 minutes and incubated at 37° C. (in the dark) for 24 or 48 hours. The stain was removed and replaced with the destaining solution (70% EtOH). Clearing was accelerated by placing the tubes at 37° C. Depending on the amount of pigment in the tissue, several changes of 70% EtOH were required. The stained seedlings and other tissues were viewed under a dissecting microscope and images were digitally recorded. In the case of siliques, the silques were removed from plants and opened with a scalpel to permit penetration of stain. The GUS stain used in the procedure was modified to include 0.5% Triton X100. Following staining, the siliques were destained by incubating in EtOH:Acetic Acid (2:1) and then incubating in Hoyer's Light medium (100 g Chloral hydrate in 60 ml water). Siliques with younger seeds were preincubated in the Ethanol:Acetic Acid solution for 4 hours, and with older seeds for 8 hours. Siliques were cleared in Hoyer's Light medium for 24 hours to several days.
Results:
GUS expression in *Arabidopsis thaliana* transformed with pCam1301UCD2-4 was observed. GUS expression was found to be abundant in cotyledons and in the hypocotyl of one week old seedlings. In two week old seedlings, GUS staining was still abundant in the first two cotyledons, and at a lower level in the first true leaves. GUS activity was not significantly detected in the root or in the second pair of developing leaves. No expression was detected in mature leaves. GUS expression was also detected in the silique wall and in developing seeds. A 48-hour GUS staining of seeds of a T1 line resulted in some seeds being positive for GUS activity and others being negative.

In summary, the data presented in this example confirm that the coffee dehydrin promoter CcDH2 drives the expression of the linked gene (in this case GUS) strongly in seeds, siliques, and in the first cotyledons and hypocotyls of the germinating seeds. This result demonstrates that the CcDH2 promoter sequence described here contains all the functional elements required to drive seed specific gene expression in plants. The data obtained also indicates that the CcDH2 promoter can be used to drive the expression of genes in immature tissues such the embryo derived first two cotyledons of seedlings. In addition, the data indicate that the CcDH2 promoter is activated in other tissues destined to undergo desiccation, such as the siliques. Finally, given the relatively large evolutionary distance between *Arabidopsis* and Coffee, the data presented here showing that the coffee CcDH2 promoter functions in *arabidopsis*, implies that this promoter should be active in a relatively wide variety of plants.

Example 10

Osmotic Stress-Induced Expression of Genes Encoding Coffee Dehydrins CcDH1 and CcDH2

Dehydrin genes are known to be induced under different forms of osmotic stress. Therefore, an evaluation was conducted to determine whether the coffee CcDH1 and CcDH2 genes were induced by different osmotic stresses.
Materials and Methods:

Dehydration experiments were carried out using small clonally propagated, *Coffea arabica* catimor trees grown in a greenhouse. The trees were approximately 3 years old and were growing in soil. Several weeks prior to the experiments, the trees were cultivated together in the greenhouse with a temperature of approximately 25° C., with a relative humidity of approximately 70%, and were watered daily using automatic irrigation. At the start of the experiment, three trees acted as controls and were watered daily. The other three trees were not watered and thus underwent a progressive dehydration. Sampling of two young leaves (5-8 cm in size and taken from the emerging growth at the top of plant) was carried out every week for each tree and the samples were frozen directly in liquid nitrogen.

RNA Extraction and Synthesis of cDNA.

The extraction of tissue samples subjected to the various stress treatments and the controls, was done using the RNEASY® Plant mini kit of Qiagen GmbH (Hilden, Germany). The frozen tissue samples were initially ground in a mortar and pestle using liquid nitrogen in order to obtain a powder. The RNA in this frozen powder was then extracted according to the protocol of the RNEASY® Plant mini kit. In brief, a maximum of 100 mg frozen powder was mixed with the cellular lysis buffer and beta-mercaptoethanol. For tissues that showed significant necrosis, 2 μM PMSF was also added. In order to eliminate low levels of contaminating genomic DNA, a treatment using DNase free-RNase contained in the RNEASY® Plant mini kit was used (as described by the supplier), that is, a 15 min treatment at room temperature on the column. At the end, the RNA was eluted from the column in 50 μL RNase free water. The RNA quantity was determined by spectrophotometric measurement at 260 nm and the RNA quality was estimated by calculating the absorbance ratio 260 nm/280 nm. The quality of RNAs was also verified by electrophoresis on 1% agarose gels. The reverse transcription reactions for these RNA samples were carried out as follows; approximately 1 μg total RNA and 12.4 μM of oligo-dT [2.3 μl of 70 μM oligo-dT (Proligo)] with Rnase free water to a final volume of 13 μL. This mixture was incubated at 65° C. for 5 min. Then, 7 μL of a mix of 5× buffer (TRANSCRIPTOR® RT reaction buffer), 20 U of RNase inhibitor, 1 mM of the four dNTPs (250 um each) and 10 U of TRANSCRIPTOR® reverse transcriptase (Roche, Nutley, N.J.) was added. This mixture was incubated at 55° C. for 40 min. Lastly, 0.5 μL of RNaseH (Invitrogen, Carlsbad, Calif.) was then added to the 20 μL of mixture and the reaction was further incubated for 30 min at 37° C. The cDNAs generated were purified using the SNAP™ Gel Purification Kit of Invitrogen (Carlsbad, Calif.) according to the protocol provided by the supplier.

Primers and MGB-Probe Design.

The primers and MGB-probe sets were designed using the PRIMER EXPRESS™ software (Applied Biosystems, Foster City, Calif.). The temperatures of hybridisation of the primers were around 60° C. whereas that of MGB-probe was close to 70° C. The size of the amplicons was approximately 80 bp. The primers were synthesized by PROLIGO and the MGB probes were synthesized in accordance with supplier's instructions (Applied Biosystems, Foster City, Calif.). The sequences of the primers and probes for CcDH2 and Ccrp139 have been presented above in Table 1. The primers for CcDH1 were 5' CACTGGCACTACTGGAGCCTATG 3' (SEQ ID NO:45) and 5' GCTGGGTGGCGTATGCA 3'. The MGB probe for CcDH1 was 5' CTGGAGCACATGGGA 3' (SEQ ID NO:46).

Real-Time Quantitative RT-PCR.

The cDNA used for these experiments was prepared as described above. TaqMan-PCR was performed as recommended by the manufacturer (Applied Biosystems, Perkin-Elmer) and as described hereinabove. Briefly, all reactions were 25 μL volume and contained 5 μl cDNA, 1× TaqMan buffer (Applied Biosystems), 5 mM MgCl$_2$, 200 μM each of dATP, dCTP, dGTP and dUTP, and 0.625 units of AmpliTaq Gold DNA polymerase. The Applied Biosystems reaction buffer contains AmpErase® UNG (Uracil-N-glycosylase) and Passive reference dye (ROX™), and optimised buffer components. The PCR reactions were carried out using 800 nM of the gene specific primers, forward and reverse, and with 200 nM of the TaqMan probe and 5 μL of 100-fold dilution cDNA, which corresponds to approximately 0.01 μg of total RNA. The reactions were incubated for 2 min at 50° C., then 10 min at 95° C., followed by 40 amplification cycles of 15 sec at 95° C./1 min at 60° C. The reactions were run and analysed using a GeneAmp 7500 Sequence Detection System (Applied Biosystems). Each sample was run 3 times and the average value calculated. Quantification was carried out using the method of relative quantification, with the constitutively expressed mRNA for the ribosomal protein rp139 acting as the internal reference for each sample. In order to use the method of relative quantification, it was necessary to show that the amplification efficiency for the different test gene sequences were roughly equivalent to the amplification efficiency of the reference sequence (rp139 cDNA sequence) using the specifically defined primer and probe sets. To determine this relative equivalence, plasmid DNA containing the appropriate cDNA sequences were diluted 1/1000, 1/10,000, 1/100,000, and 1/1,000,000 fold, and using the Q-PCR conditions described above, the slope of the curve Ct=f(Log quantity of DNA) was calculated for each plasmid/primer/

TaqMan probe set. Plasmid/primer/TaqMan probe sets giving curves with slopes close to 3.32, which represents an efficiency of 100%, were considered acceptable. The plasmid/primer/TaqMan probe sets used all gave acceptable values for Ct=f(Log quantity of DNA).

The absence of any significant level of residual genomic DNA in the cDNA preparations was verified by measuring the level of quantitative PCR amplification signal for a genomic specific primer/probe set for GOS gene versus the signal for a GOS gene cDNA probe.

Figure 9:
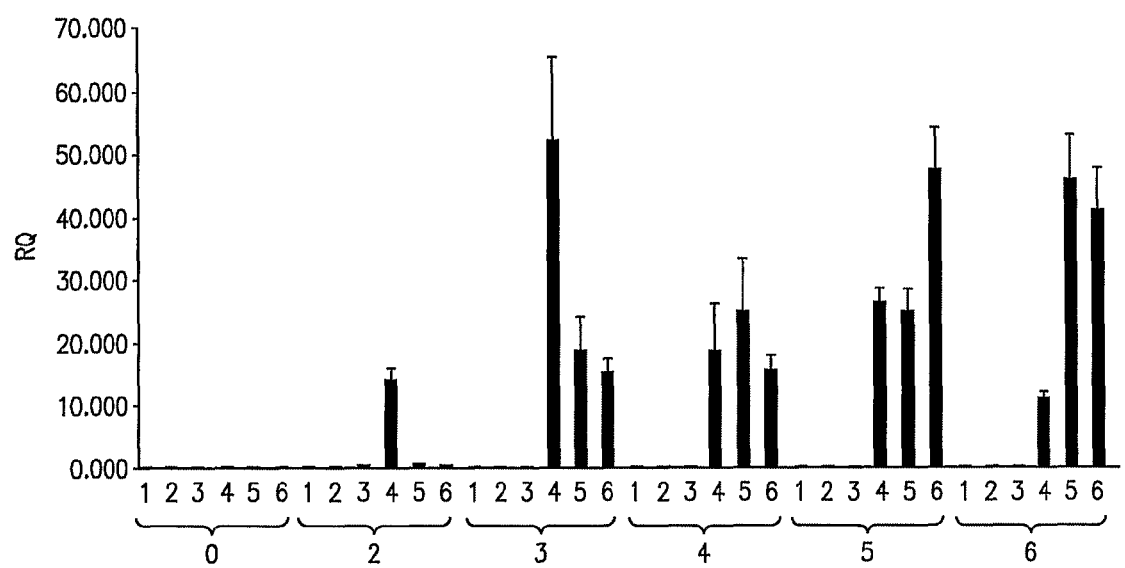
FIG. 9. Real Time Quantitative RT-PCR expression analysis of CcDH1 expression in the leaves of control and drought stressed plants. Plants 1-3 were regularly watered control plants; plants 4-6 were given no water from the initiation of the experiment ("0") through week 6.
Figure 10:
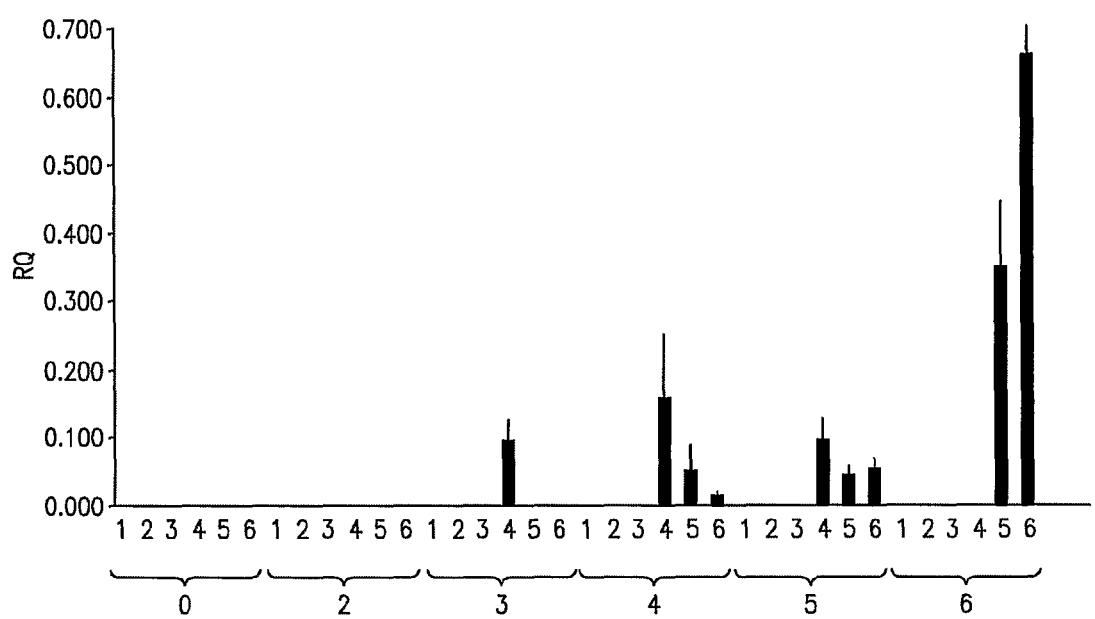
FIG. 10. Real Time Quantitative RT-PCR expression analysis of CcDH2 expression in the leaves of control and drought stressed plants. Plants 1-3 were regularly watered control plants; plants 4-6 were given no water from the initiation of the experiment ("0") through week 6.

Results:

FIG. 9 shows the induction of CcDH1 gene expression in the leaves of small green house grown trees when watering is stopped (drought conditions). After two weeks, DH1 expression is significantly induced in one of the water stressed plants (plant #4). After three weeks, CcDH1 expression has been induced in all three of the water stressed plants (plants #4-6). The induction is very significant, reaching an RQ of over 50 for plant #4. Considering the control gene rp139 is relatively highly expressed, an RQ of 50 represents a very high level of gene expression induction, and strongly suggests that CcDH1 plays an important role in the drought response of coffee leaves. FIG. 10 shows the induction of CcDH2 gene expression in the same set of samples. The induction of CcDH2 shows several differences to the response of CcDH1. The first difference is that CcDH2 is clearly induced later than CcDH1, with the apparently most stressed plant (plant #4) showing induction at week 3, one week later than for CcDH1. By week 4, CcDH2 has been induced in all three water stressed plants. The second difference between CcDH2 versus CcDH1 induction is that the level of CcDH2 induction is significantly lower than observed for CcDH1. Overall, these results indicate that CcDH1 and CcDH2 are not induced in precisely the same manner, although the signals are probably overlapping, ie. the signal(s) needed for CcDH1 induction are needed for CcDH2, but, CcDH2 may need additional signal(s) that appear only as the water stress increases. Supporting the argument that CcDH2 is induced by conditions approaching extreme water loss, the expression in plants #5 and #6 continued to increase as the water stress worsened with time without water. Alternatively, it may be that CcDH2 is expressed more significantly than indicated in FIG. 10, but this induction is localized to specific tissues. It is important to note that the three control plants that were regularly watered showed no induction of CcDH1 or CcDH2 (FIGS. 9, 10; plant #1-3).

The results presented above indicate that the promoters associated with CcDH1 and CcDH2 can be useful for inducing and driving gene expression in osmotically stressed tissues. For example, these promoters can be used to drive expression of genes that are capable of affording some protection from osmotic stress at the precise period when this stress occurs, but not in most tissues under normal conditions. It is also apparent from the work above that, if the goal is to induce a gene at low water stress, the promoter for CcDH1 would optimally be used, while for gene induction at higher water stress, the use of the CcDH2 would be more ideal when the object is to induce a recombinant gene only under relatively high water stress conditions.

To further examine the effect of different osmotic stress conditions we examined the effect of cold temperature and elevated levels of NaCl on CcDH1 and CcDH2 expression. We have also tested the effect of a hormone associated with osmotic stress signalling (abscisic acid—ABA). For these experiments, we used microcuttings of coffee growing on solid media in-vitro (solid media B0.3 in petri dish plates). For the experiment with cold and ABA we generated microcuttings for robusta variety ThB4 on B0.3 plates (16 hour photoperiod). When these microcuttings were sufficiently large, they were transferred to new media/plates and incubated a further 7 days at 24° C. (16 hour photoperiod). At T=0, one set of plates were transferred to 5° C. for 7 days (16 hour photoperiod). Another set of these microcuttings were put on media with ABA (media B0.3+100 uM ABA) for 7 days at 24° C. (16 hour photoperiod). The samples taken at T=0 and T=7 days (5° C. and ABA), were frozen at −80° C. and then the RNA was extracted for QRT-PCR analysis as described above. The expression results obtained for the T=0 sample of the starting material indicate that CcDH1 had an RQ=1.17. Other experiments have shown the basal levels of CcDH1 can vary from RQ 0.05 to approximately RQ 1 in microcuttings. Such a relatively broad spread suggests that the higher level represents the detection of a slight osmotic stress in the starting material for this experiments (possibly related to how well the material has fixed to the solid media and/or how well the plates are sealed which affects the relative humidity, and the precise age of the starting material). Nonetheless, the samples kept at 5° C. for 7 days showed no induction of CcDH1, and, in fact, the levels of CcDH1 actually fell to an RQ=0.16, a level closer to expression level more often seen in unstressed microcuttings).

In contrast to the data presented above for CcDH1, no CcDH2 expression was detected in the T=0. However, after 7 days at 5° C., an RQ=0.022 was detected for CcDH2. This latter observation suggests that CcDH2 is induced very slightly by cold conditions. It is noted that 5° C. is a very low temperature for coffee, and thus it is possible that if the temperature of the cold stress was slightly higher (8-15° C.), the induction of CcDH2 could be more significant. Finally, the microcuttings treated with 100 um ABA for 7 days showed a significant increase in CcDH1 expression (RQ, 6.99). This latter result demonstrates that ABA is involved in the signalling for CcDH1 induction. In contrast, ABA did not produce any detectable expression of CcDH2 indicating this hormone alone is not sufficient to induce CcDH2 to any detectable extent.

To test the effect of salt, we added 250 mM NaCl into the solid medium B0.3. At T=O, a set of microcuttings from Robusta FRT 35 were placed on B0.3 media or B0.3 media with 250 mM NaCl and placed at 24° C. (16 hour photoperiod). At T=0 and at days 4 and 7 samples were taken and frozen at −80° C. for later QRT-PCR analysis as described above. The results obtained show that, in the controls, the levels of CcDH1 were quite low at the start and stayed low throughout the experiment (Control—T=0, RQ=0.2; T=4 days, RQ=0.07; T=7 days, RQ=0.38). In the test treatment, the level of CcDH1 rose significantly at days 4 and 7 of the treatment (250 mM NaCl—T=4 days, RQ=3.31; T=7 days, RQ=4.46). This experiment shows that raising the salt concentration can induce DH1 expression to significant levels, although not as high as seen in the leaves of plants under water stress. No significant induction was seen for CcDH2 expression in the presence of 250 mM NaCl in either the T=4 or T=7 day samples.

REFERENCES

Agrawal N, Dasaradhi P V N, Mohmmed A, Malhotra P, Bhatnagar R K, Mukherjee S K: RNA interference: Biology, mechanism, and applications. Microbiol. Mol. Biol. Rev. 67:657-685 (2003).

Allagulova, C R, Gimalov, F R, Shakirova, F M, Vakhitov, V A: The plant dehydrins: Structure and putative functions. Biochemistry-Moscow 68: 945-951 (2003).

Alsheikh, M K, Heyen, B J, Randall, S K: Ion binding properties of the dehydrin ERD14 are dependent upon phosphorylation. J. Biol. Chem. 278: 40882-40889 (2003).

Baumlein H, NIVRIDWU: Cis-analysis of a seed protein gene promoter: the conservative RY repeat CATGCATG within the legumin box is essential for tissue-specific expression of a legumin gene. Plant J. 2: 233-239 (1992).

Brummelkamp T R, Bernards R, Agami R: A system for stable expression of short interfering RNAs in mammalian cells. Science 296:550-553 (2002).

Chatthai M, FBYDSIOLOMMS: 2S storage protein gene of Douglas-fir: characterization and activity of promoter in transgenic tobacco seeds. Plant Physiol Biochem 42: 417-423 (2004).

Choi, D W, Close, T J: A newly identified barley gene, Dhn12 encoding a YSK2 DHN, is located on chromosome 6H and has embryo-specific expression. Theoretical and Applied Genetics 100: 1274-1278 (2000).

Close, T: Dehydrins: emergence of a biochemical role of a family of plant dehydration proteins. Physiol. Plant 97: 795-803 (1996).

Close, T J: Dehydrins: a commonality in the response of plants to dehydration and low temperature. Physiol. Plant 100: 291-296 (1997).

Clough, S J and Bent A F: Floral dip: a simplified method for Agrobacterium-mediated transformation of Arabidopsis thaliana. Plant Journal 16; 735-743 (1998).

Crouzillat, D, Lerceteau, E, Petiard, V, Morera, J, Rodriguez, H, Walker, D, Philips, W R R, Schnell, J, Osei, J, Fritz, P: Theobroma cacao L.: a genetic linkage map and quantitative trait loci analysis. Theor. Appl. Genet. 93: 205-214 (1996).

Dubouzet J G, SYIYKMDEMSSMSKY-SK: OsDREB genes in rice, Oryza sativa L., encode transcription activators that function in drought-, high-salt- and cold-responsive gene expression. Plant J. 33: 751-763 (2003).

Dure, L, Greenway, S, Galau, G: Biochemistry 20: 4162-4178 (1981).

Dure, L: Structural motifs in LEA proteins of higher plants. In: Close, T. J., Bray, E, and A. (eds), Response of Plants to Cellular Dehydration During Environmental Stress, pp. 91-103. American Society of Plant Physiologists, Rockville, Md. (1993).

Elbashir S M, Harborth J, Weber K, Tuschl T: Analysis of gene function in somatic mammalian cells using small interfering RNAs. Methods 26:199-213 (2002).

Godoy, J A, Lunar, R, Torres-Schumann, S, Moreno, J, Rodrigo, M, Pintor-Toro, J A: Expression, tissue distribution and subcellular localization of dehydrin TAS14 in salt-stressed tomato plants. Plant Mol. Biol. 1921-1934 (1994).

Hara, M, Terashima, S, Fukaya, T, Kuboi, T: Enhancement of cold tolerance and inhibition of lipid peroxidation by citrus dehydrin in transgenic tobacco. Planta 217: 290-298 (2003).

Hara, M, Fujinaga, M, Kuboi, T: Radical scavenging activity and oxidative modification of citrus dehydrin. Plant Physiology and Biochemistry 42: 657-662 (2004).

Iida, K, Seki, M, Sakurai, T, Satou, M, Akiyama, K, Toyoda, T, Konagaya, A, Sinozaki, K: Genome-wide analysis of alternative pre-mRNA splicing in Arabidopsis thaliana based on full-length cDNA sequences. Nucleic Acids Research 32: 5096-5103 (2004).

Ingram, J, Bartels, D: The molecular basis of dehydration tolerance in plants. Annu. Rev. Plant Physiology Plant Mol Biol 47: 377-403 (1996).

Iwasaki, T, Yamaguchi-Shinozaki, K, Shinozaki, K: Identification of a cis-regulatory region of a gene in Arabidopsis thaliana whose introduction by dehydration is mediated by abscisic acid and requires protein synthesis. Molecular and General Genetics 247: 391-398 (1995).

Klahre U, Crete P, Leuenberger A S, Iglesias V A, Meins F: High molecular weight RNAs and small interfering RNAs induce systemic post-transcriptional gene silencing in plants. Proc. Natl. Acad. Sci. USA 99:11981-11986 (2002).

Koag, M C, Fenton, R D, Wilkens, S, Close, T J: The binding of maize DHN1 to lipid vesicles. Gain of structure and lipid specificity. Plant Physiology 131: 309-316 (2003).

Marraccini P., Deshayes A., Pétiard V. and Rogers W. J. 1999. Molecular cloning of the complete 11S seed storage protein gene of Coffea arabica and promoter analysis in the transgenic tobacco plants. Plant Physiol. Biochein. 37:273-282.

Marraccini P, Courjault C, Caillet V, Lausanne F, LePage B, Rogers W, Tessereau S, and Deshayes A. 2003. Rubisco small subunit of Coffea arabica: cDNA sequence, gene cloning and promoter analysis in transgenic tobacco plants. Plant Physiol. Biochem. 41:17-25.

Matsuyama, T, Yasumura, N, Funakoshi, M, Yamada, Y, Hashimoto, T: Maize genes specifically expressed in the outermost cells of the root cap. Plant Cell Physiol. 40: 469-476 (1999).

Mishra R N, Singla-Pareek S L, Nair S, Sopory S K, Reddy M K: Directional genome walking using PCR. Biotechniques. 33:830-834 (2002).

Moore, R, McClelen, C: Ultrastructural aspects of cellular differentiation in the root cap of Zea mays. Can. J. Bot. 61: 1566-1572 (1983).

Nylander, M, Svensson, J, Palva, E T, Welin, B V: Stress-induced accumulation and tissue-specific localization of dehydrins in Arabidopsis thaliana. Plant Molecular Biology 45: 263-279 (2001).

Puhakainen, T, Hess, M W, Makela, P, Svensson, J, Heino, P, Palva, E T: Overexpression of multiple dehydrin genes enhances tolerance to freezing stress in Arabidopsis. Plant Molecular Biology 54: 743-753 (2004).

Rishi A S, Nelson N D, Goyal A: Genome walking of large fragments: an improved method. J. Biotechnol. 111:9-15 (2004).

Roberts, J, DeSimone, N, Lingle, W, Dure, L: Cellular concentrations and unifomity of cell-type accumulation of two LEA proteins in cotton embryos. Plant Cell 5: 769-780 (1993).

Rogers, W J., Bézard, G., Deshayes, A., Meyer, I., Pétiard, V., Marraccini, P. (1999). Biochemical and molecular characterisation and expression of the 11S-type storage protein from Coffea arabica endosperm. Plant Physiol. Biochem. 37(4): 261-272.

Shirsat A, WNCRBD: Sequences responsible for the tissue specific promoter activity of a pea legumin gene in tobacco. Molecular and General Genetics 215: 326-331 (1989).

Skriver, K, Mundy, J: Gene expression in response to abscisic acid and osmotic stress. Plant Cell 2: 503-512 (1990).

Soulages, J L, Kim, K, Arrese, E L, Walters, C, Cushman, J C: Conformation of a group 2 late embryogenesis abundant protein from soybean. Evidence of poly (L-proline)-type II structure. Plant Physiology 131: 963-975 (2003).

Spanier, A M, Flores, M, Toldra, F, Aristoy, M C, Bett, K L, Bystricky, P, Bland, J: Meat flavor: contribution of proteins and peptides to the flavor of beef. Adv. Exp. Med. Biol. 542: 33-49 (2004).

Turner, J, Linforth, R, Taylor, A: Real-time monitoring of thermal flavor generation in skim milk powder using atmospheric pressure chemical ionization mass spectrometry. J. Agric. Food Chem 50: 5400-5404 (2002).

Tuschl T, Borkhardt A: Small interfering RNAs: A revolutionary tool for the analysis of gene function and gene therapy. Mol. Interventions. 2:158-167 (2002).

Wise, M, Tunnacliffe, A: POPP the question: what do LEA proeins do? Trends Plant Sci. 9: 13-17 (2004).

Zhu, B, Choi, D W, Fenton, R, Close, T J: Expression of the barley dehydrin multigene family and the development of freezing tolerance. Molecular and General Genetics 264: 145-153 (2000).

Sequences of Claimed Nucleic Acids and Polypeptides

```
CcDH1a cDNA (see SEQ ID NO: 1) and encoded protein (see SEQ ID NO: 7)
gtgggaagaa gtcctatcgg tctctgatct ttcaccttc gttaatttgt gttcgatatt      60
ctactcccgc tagtagttga aatttggcaa ttaag atg gcg caa tac ggg gct       113
                                       Met Ala Gln Tyr Gly Ala
                                       1               5 gaa tat ggc aac caa aag agc cag tac gat gag tac gga aac cca gtt      161
Glu Tyr Gly Asn Gln Lys Ser Gln Tyr Asp Glu Tyr Gly Asn Pro Val
            10                  15                  20 cgt cag aca gac gaa tat ggt aac cct gcc cgc cat gga ggt acc atg      209
Arg Gln Thr Asp Glu Tyr Gly Asn Pro Ala Arg His Gly Gly Thr Met
        25                  30                  35 ggt gat tat gga acc act ggc act act gga gcc tat ggt ggc aca act      257
Gly Asp Tyr Gly Thr Thr Gly Thr Thr Gly Ala Tyr Gly Gly Thr Thr
40                  45                  50 gga gca cat ggg act tat gca act gga acc acc ggc act acc ggt acc      305
Gly Ala His Gly Thr Tyr Ala Thr Gly Thr Thr Gly Thr Thr Gly Thr
55                  60                  65                  70 ggt gca tac gcc acc cag cct ggc act gat gtg ggg aag gag cac cat      353
Gly Ala Tyr Ala Thr Gln Pro Gly Thr Asp Val Gly Lys Glu His His
                75                  80                  85 ggc ctt ggt ggc atg ctt cat cgc tct ggc agc ggt agc tct agc tcg      401
Gly Leu Gly Gly Met Leu His Arg Ser Gly Ser Gly Ser Ser Ser Ser
                90                  95                  100 tcc gag gat gat ggg caa ggc ggg agg agg aag aag ggg atg aag gag      449
Ser Glu Asp Asp Gly Gln Gly Gly Arg Arg Lys Lys Gly Met Lys Glu
            105                 110                 115 aag ata aag gag aaa ctg cct ggc ggt cac aag gag gct caa cct gga      497
Lys Ile Lys Glu Lys Leu Pro Gly Gly His Lys Glu Ala Gln Pro Gly
        120                 125                 130 caa gaa tat tcg agt gct act gca gct cct gga tac ggc ggg gaa gga      545
Gln Glu Tyr Ser Ser Ala Thr Ala Ala Pro Gly Tyr Gly Gly Glu Gly
135                 140                 145                 150 gtg cag cac gag aag aaa gga att atg gat aaa atc aag gag aaa tta      593
Val Gln His Glu Lys Lys Gly Ile Met Asp Lys Ile Lys Glu Lys Leu
                155                 160                 165 cca ggg ggt cac cac aac tga agatctaatt ctaataaata ttggtccgat         644
Pro Gly Gly His His Asn
                170 tatgatattg tgtaccctg ttttcaatct caatctcgtt cgtgtcgcgt ttgtgttttc     704 tgagatttga gtgtgtggac gtcttgagtt tctgtaattg gaataaaaga tgattcgtct    764 tcgtcttcgt ggactctgta gtgtgtttgt ccgtatattc ggcgtcttgt actcgggtca    824 tctggtcatg ta                                                        836

CcDH1b cDNA (see SEQ ID NO: 2) and encoded protein (see SEQ ID NO: 8)
gtgggaagaa gtcttatcgg tctctgatcc ttcaccttc gttaatctgt gttctatatt      60
ctacttccgc tagtagttga aatttggcaa ttaag atg gcg caa tac ggg gct       113
                                       Met Ala Gln Tyr Gly Ala
                                       1               5 gaa tat ggc aac caa aag agc cag tac gat gag tac gga aac cca gtt      161
Glu Tyr Gly Asn Gln Lys Ser Gln Tyr Asp Glu Tyr Gly Asn Pro Val
            10                  15                  20
```

-continued

```
cgt cag aca gac gaa tat ggt aac cct gcc cgc cat gga ggt acc atg        209
Arg Gln Thr Asp Glu Tyr Gly Asn Pro Ala Arg His Gly Gly Thr Met
         25                  30                  35 ggt gat tat gga acc act ggc act act gga gcc tat ggt ggc aca act        257
Gly Asp Tyr Gly Thr Thr Gly Thr Thr Gly Ala Tyr Gly Gly Thr Thr
 40                  45                  50 ggg aca gct gga gca cat ggg act tat gca act gga acc acc ggc act        305
Gly Thr Ala Gly Ala His Gly Thr Tyr Ala Thr Gly Thr Thr Gly Thr
 55                  60                  65                  70 acc ggt acc ggt gca tat gcc acc cag cct ggc act gat gtg ggg aag        353
Thr Gly Thr Gly Ala Tyr Ala Thr Gln Pro Gly Thr Asp Val Gly Lys
                 75                  80                  85 gag cgc cat ggc ctt ggt ggc atg ctt cat cgc tct ggt agc ggt agc        401
Glu Arg His Gly Leu Gly Gly Met Leu His Arg Ser Gly Ser Gly Ser
         90                  95                 100 tct agc tcg tcc gag gat gat ggg caa ggc ggg agg agg aag aag ggg        449
Ser Ser Ser Ser Glu Asp Asp Gly Gln Gly Gly Arg Arg Lys Lys Gly
        105                 110                 115 atg aag gag aag ata aag gag aaa ctg cct ggc ggt cac aag gag gct        497
Met Lys Glu Lys Ile Lys Glu Lys Leu Pro Gly Gly His Lys Glu Ala
120                 125                 130 caa cct gga caa gaa tat tcg agt gct act gca gct cct gga tac ggc        545
Gln Pro Gly Gln Glu Tyr Ser Ser Ala Thr Ala Ala Pro Gly Tyr Gly
135                 140                 145                 150 ggg gaa gga gag cag cac gag aag aaa gga att atg gat aaa atc aag        593
Gly Glu Gly Glu Gln His Glu Lys Lys Gly Ile Met Asp Lys Ile Lys
                155                 160                 165 gag aaa tta cca ggg ggt cac cgc aac tga agatctaatt ctaataaata        643
Glu Lys Leu Pro Gly Gly His Arg Asn
        170                 175 ttggatccaa ttatgatatc gtgtaccccct gttttcaatc tcaatctcgt tcgtgtcgcg     703
tttgtgtctt ctgagatttg agtgtgtggg cgtcttgagt ttctgtaatc ggaataaaga     763
tgattcgtct tcgtcttcgt cttcgtcttc gtggactctg tagtgtgttt gtccgtatat     823
tcggcgtctt gtactcgggt catctggtca tgtatgtaac atgttatata tcaaatacgt     883
gaagttttgc gttaaaaaaa aaaaaaaaaa aaaaaaaaaa aaaaaaaaaa aaaaaaaaaa     943
aaaaaaaaaa aaa                                                        956

CcDH2a (see SEQ ID NO: 3) and encoded protein (see SEQ ID NO: 9)
ctaaaattcg tcaaccccaa gtctcaggct accttaattt cagtgcccctt tttctttatt       60 tttttctaat aacaggagtc ctggaaa atg gct gac ttg cgt gat gaa tat gga       114
                                Met Ala Asp Leu Arg Asp Glu Tyr Gly
                                 1               5 aat cct atg cag ttg acc gac cag tat ggc aac ccg gtt cag ctc aag        162
Asn Pro Met Gln Leu Thr Asp Gln Tyr Gly Asn Pro Val Gln Leu Lys
 10                  15                  20                  25 gac gag tat ggc aac cca atg cag ctt agc ggt gta gct atc acc gcc        210
Asp Glu Tyr Gly Asn Pro Met Gln Leu Ser Gly Val Ala Ile Thr Ala
                 30                  35                  40 ggg acg gct agt gct gtc cat tct act gga acc gga cca act gct gcc        258
Gly Thr Ala Ser Ala Val His Ser Thr Gly Thr Gly Pro Thr Ala Ala
         45                  50                  55 act gga acc cag caa cat cag gag cag ctt cat cgg tct agc agc tca        306
Thr Gly Thr Gln Gln His Gln Glu Gln Leu His Arg Ser Ser Ser Ser
 60                  65                  70 agc tct ggc tcg tcg gag gat gat gga caa gga gga aga aga aag aaa        354
Ser Ser Gly Ser Ser Glu Asp Asp Gly Gln Gly Gly Arg Arg Lys Lys
         75                  80                  85 aaa ggg ttg aaa gaa aag ata aag gag aaa cta acg ggc ggg agg cac        402
Lys Gly Leu Lys Glu Lys Ile Lys Glu Lys Leu Thr Gly Gly Arg His
```

-continued

```
            90                  95                 100                105
aag gac aga gac gat cag gag cac atc gat gat cag cac gcg cac agc       450
Lys Asp Arg Asp Asp Gln Glu His Ile Asp Asp Gln His Ala His Ser
                110                 115                 120 gcc tct cct cca aca acc acc act ggc agc ggg acg tct act aca gtc       498
Ala Ser Pro Pro Thr Thr Thr Thr Gly Ser Gly Thr Ser Thr Thr Val
            125                 130                 135 ggg ggt cag cag cat gaa aag aag agc atg gtg gag aag att atg gaa       546
Gly Gly Gln Gln His Glu Lys Lys Ser Met Val Glu Lys Ile Met Glu
        140                 145                 150 aag ctc cct ggc cat cac gac acc cgc tag ttacctacca caacatactg         596
Lys Leu Pro Gly His His Asp Thr Arg
    155                 160 tgatcatcgt gtaaaatctc tcctgatgcc taggaaatct agattatgtt aggcattttg     656
tttggtatgt atgtgtgatt aagaccttgt tgtgcgcttg aatcttgaac gtgcatggga     716
tttgcttggt ttgatttgat ttggtgaaat aagttgtact aaaaaaaaaa aaaaaaa       774
```

CcDH2b cDNA (see SEQ ID NO: 4) and encoded protein (see SEQ ID NO: 10)

```
ctaaaattcg tcaaccccaa gtctcaggct accttaattt cagtgcccct tttctttatt     60
tttttctaat aacaggagtc ctggaaa atg gct gac ttg cgt gat gaa tat gga    114
                            Met Ala Asp Leu Arg Asp Glu Tyr Gly
                              1               5 aat cct atg cag ttg acc gac cag tat ggc aac ccg gtt cag ctc aag       162
Asn Pro Met Gln Leu Thr Asp Gln Tyr Gly Asn Pro Val Gln Leu Lys
 10                  15                  20                  25 gac gag tat ggc aac cca atg cag ctt agc ggt gta gct atc acc gcc       210
Asp Glu Tyr Gly Asn Pro Met Gln Leu Ser Gly Val Ala Ile Thr Ala
                 30                  35                  40 ggg acg gct agt gct gtc cat tct act gga acc gga cca act gct gcc       258
Gly Thr Ala Ser Ala Val His Ser Thr Gly Thr Gly Pro Thr Ala Ala
     45                  50                  55 act gga acc cag caa ctt cag gag cag ctt cat cgg tct agc agc tca       306
Thr Gly Thr Gln Gln Leu Gln Glu Gln Leu His Arg Ser Ser Ser Ser
             60                  65                  70 agc tct ggc tcg gtgagatact tgccaagtta caatgtgtgt gtctgtgtgt           358
Ser Ser Gly Ser
         75 gtataatgcg ccatcataat tgtttgcttg acagatcctg ttaataatga accgtaattt     418 gacgtaaagt gtacacgttt tgttttctg ggacttacat aatatcgaat caggctcctg    478 ttgaatttga atgttgttag ctaaagaaa attttggtgg ctgagttgtt gaatttggtt    538 tatgg tcg gag gat gat gga caa gga gga aga aga aag aaa aaa ggg ttg    588
      Ser Glu Asp Asp Gly Gln Gly Gly Arg Arg Lys Lys Lys Gly Leu
           80                  85                  90 aaa gaa aag ata aag gag aaa cta acg ggc ggg agg cac aag gac aga       636
Lys Glu Lys Ile Lys Glu Lys Leu Thr Gly Gly Arg His Lys Asp Arg
         95                 100                 105 gac gat cag gag cac atc gat gat cag cac gcg cac agc gcc tct cct       684
Asp Asp Gln Glu His Ile Asp Asp Gln His Ala His Ser Ala Ser Pro
    110                 115                 120 cca aca acc acc act ggc agc ggg acg tct act aca gtc ggg ggt cag       732
Pro Thr Thr Thr Thr Gly Ser Gly Thr Ser Thr Thr Val Gly Gly Gln
125                 130                 135                 140 cag cat gaa aag aag agc atg gtg gag aag att atg gaa aag ctc cct       780
Gln His Glu Lys Lys Ser Met Val Glu Lys Ile Met Glu Lys Leu Pro
            145                 150                 155 ggc cat cac gac acc cgc tagttaccta ccacaacata ctgtgatcat              828
Gly His His Asp Thr Arg
        160
```

-continued

```
cgtgtaaaat ctctcctgat gcctaggaaa tctagattat gttaggcatt ttgtttggta    888
tgtatgtgtg attaagacct tgttgtcgc ttgaatcttg aacgtgcatg ggatttgctt    948
ggtttgaaaa aaaaaaaaaa aaaaaaaaaa aaaaaaaaaa aaaaaaaaaa aaaaaaaaaa   1008
aaaaaaaaaa aa                                                        1020
```

CcDH3 cDNA (see SEQ ID NO: 5) and encoded protein (see SEQ ID NO: 11)

```
attttttgct gtttcctgtt acattctgct ttacgtacat ccatcagcaa a atg gcc     57
                                                         Met Ala
                                                           1 gag tat gat cag agt aac atc aag gtt gag gag gga tca gct gtc gag     105
Glu Tyr Asp Gln Ser Asn Ile Lys Val Glu Glu Gly Ser Ala Val Glu
     5                  10                 15 gcc acg gat cgc gga ctc ttc aac ttg ggc aag aaa gag gaa gtg aag     153
Ala Thr Asp Arg Gly Leu Phe Asn Leu Gly Lys Lys Glu Glu Val Lys
 20                  25                 30 aag tgt gat caa ggc cag gcc atc tct gcg gag ttt gat gag aaa gtg    201
Lys Cys Asp Gln Gly Gln Ala Ile Ser Ala Glu Phe Asp Glu Lys Val
 35                  40                 45                 50 cgt gtt tct gaa cca gac aag gag gag gga aag aag cat ggt ggt ctt     249
Arg Val Ser Glu Pro Asp Lys Glu Glu Gly Lys Lys His Gly Gly Leu
                 55                 60                 65 ctc gag aag ctc cac cga tct ggt agc agc tcc agc agc tca agt gag     297
Leu Glu Lys Leu His Arg Ser Gly Ser Ser Ser Ser Ser Ser Ser Glu
             70                 75                 80 gaa gaa gta gaa gag ggt ggt gag aag aag aag aaa aag aag gaa aag     345
Glu Glu Val Glu Glu Gly Gly Glu Lys Lys Lys Lys Lys Lys Glu Lys
         85                 90                 95 aag ggt ttg aag gac aag atc aag gag aag ata tcg ggt gat aag aag     393
Lys Gly Leu Lys Asp Lys Ile Lys Glu Lys Ile Ser Gly Asp Lys Lys
     100                 105                 110 gac gaa gaa aag gtt gaa aaa tgt gag gaa gac acg tct atc cca gtt     441
Asp Glu Glu Lys Val Glu Lys Cys Glu Glu Asp Thr Ser Ile Pro Val
115                 120                 125                 130 gag aaa tat gcc gaa ccg gcc cat gca gat gct gct cat gaa cca gag     489
Glu Lys Tyr Ala Glu Pro Ala His Ala Asp Ala Ala His Glu Pro Glu
                 135                 140                 145 gag aaa aag ggc ttc tta gat aag atc aag gag aaa cta cca ggt ggt     537
Glu Lys Lys Gly Phe Leu Asp Lys Ile Lys Glu Lys Leu Pro Gly Gly
             150                 155                 160 ggt cag aag aag act gag gaa gtc gca gca gca ccg cct cct cct         585
Gly Gln Lys Lys Thr Glu Glu Val Ala Ala Ala Pro Pro Pro Pro
         165                 170                 175 ccg gca gag tgc acc gcc act gaa ggt gag gcc aag gat aag aag gga     633
Pro Ala Glu Cys Thr Ala Thr Glu Gly Glu Ala Lys Asp Lys Lys Gly
     180                 185                 190 ttc ttg gac aag atc aag gag aag ctc cct ggc tac cat ccc aag act     681
Phe Leu Asp Lys Ile Lys Glu Lys Leu Pro Gly Tyr His Pro Lys Thr
195                 200                 205                 210 gaa gaa gag aag gaa aag gag aag gaa aaa gaa aag gag gct gga tgc     729
Glu Glu Glu Lys Glu Lys Glu Lys Glu Lys Lys Glu Ala Gly Cys
                 215                 220                 225 cat taa taaaagagca aagcaaatta atagcagctt tccagtgtgt cataattttg      785
His catttggatt aatacatttt ggagtggcaa tgatcttttt attttaaa                833
```

CcLEA1 cDNA (see SEQ ID NO: 6) and encoded protein (see SEQ ID NO: 12)

```
aagcagtggt aacaacgcag agtacgcggg acgaacatca tcggtaccag tttcctattc     60
atacatcatc ttactagcac tg atg caa aaa atg act cct ctg aga tgc atc    112
                          Met Gln Lys Met Thr Pro Leu Arg Cys Ile
                           1               5                 10
```

```
aat ttc att ttt ctg gcc ttt tgg gtt cct gct gtc ctc gcg gtg atg      160
Asn Phe Ile Phe Leu Ala Phe Trp Val Pro Ala Val Leu Ala Val Met
         15                  20                  25 gcc gaa aaa ccc cta gtt cct aca tac cta atc ccc aaa ccc cct cca      208
Ala Glu Lys Pro Leu Val Pro Thr Tyr Leu Ile Pro Lys Pro Pro Pro
 30                  35                  40 ccg cca tcg cca gtg aaa cca tca gta ccc gtg ata cct gtc aaa ccc      256
Pro Pro Ser Pro Val Lys Pro Ser Val Pro Val Ile Pro Val Lys Pro
         45                  50                  55 cga atc gtg aga tgc cgc tcc aca ttg ttt cct ctc tgc ttc aat atc      304
Arg Ile Val Arg Cys Arg Ser Thr Leu Phe Pro Leu Cys Phe Asn Ile
 60                  65                  70 ccc ttc gtt tgc ccc tta gac tgt ctt acc aac tgt tta gtg gac tgt      352
Pro Phe Val Cys Pro Leu Asp Cys Leu Thr Asn Cys Leu Val Asp Cys
75                  80                  85                  90 gtc acc tgc aag gct tac tgc agt tgc aac ttt ccc ggc gct gtt tgt      400
Val Thr Cys Lys Ala Tyr Cys Ser Cys Asn Phe Pro Gly Ala Val Cys
                 95                 100                 105 cag gat cca cga ttc gtt ggg ggc gat ggc aac aca ttt tac ttc cat      448
Gln Asp Pro Arg Phe Val Gly Gly Asp Gly Asn Thr Phe Tyr Phe His
        110                 115                 120 ggc cgc aag gat cag gac ttc tgc ctg gtt tcg gat acc aat ctt cat      496
Gly Arg Lys Asp Gln Asp Phe Cys Leu Val Ser Asp Thr Asn Leu His
        125                 130                 135 gta aat ggt cat ttc att ggc aaa aga aaa cct aat ttg cgc aga gac      544
Val Asn Gly His Phe Ile Gly Lys Arg Lys Pro Asn Leu Arg Arg Asp
140                 145                 150 ttc act tgg gtg cag gcc att gga ata atg ttc gac gac cac aga atc      592
Phe Thr Trp Val Gln Ala Ile Gly Ile Met Phe Asp Asp His Arg Ile
155                 160                 165                 170 ctc gtg gcc gca aaa agg act tca acg tgg gac gac aat gtg gat cga      640
Leu Val Ala Ala Lys Arg Thr Ser Thr Trp Asp Asp Asn Val Asp Arg
                175                 180                 185 ctc gct ata tcc att gat gga aat ccg att tcc ctc ccc act gaa gaa      688
Leu Ala Ile Ser Ile Asp Gly Asn Pro Ile Ser Leu Pro Thr Glu Glu
        190                 195                 200 gga tcc aaa tgg caa ctt ccg gcc ccg tcc aat gtc agt atc atg aga      736
Gly Ser Lys Trp Gln Leu Pro Ala Pro Ser Asn Val Ser Ile Met Arg
        205                 210                 215 aca agc aac aat aac gga ctt gtg gtt gaa gcc gtg aac aat ttc agg      784
Thr Ser Asn Asn Asn Gly Leu Val Val Glu Ala Val Asn Asn Phe Arg
220                 225                 230 atc acc gcc aat gtg gtt cca ata aca gct caa gaa tca aaa gtt cat      832
Ile Thr Ala Asn Val Val Pro Ile Thr Ala Gln Glu Ser Lys Val His
235                 240                 245                 250 ggt tat gac att act gat gag gat tgc ttt acc cat ttg gag ctt ggg      880
Gly Tyr Asp Ile Thr Asp Glu Asp Cys Phe Thr His Leu Glu Leu Gly
                255                 260                 265 ttc aaa ttc ttc aac atc acc gat tca act gat gga gtt ttg gga caa      928
Phe Lys Phe Phe Asn Ile Thr Asp Ser Thr Asp Gly Val Leu Gly Gln
        270                 275                 280 acc tat agg agc gat tac gtg aac aaa atg aag gtg aat gcg gta atg      976
Thr Tyr Arg Ser Asp Tyr Val Asn Lys Met Lys Val Asn Ala Val Met
        285                 290                 295 cca gtc atg ggc ggt gac cgt aag tac ttg act tcg gga ctt ttt agt     1024
Pro Val Met Gly Gly Asp Arg Lys Tyr Leu Thr Ser Gly Leu Phe Ser
300                 305                 310 gcc gat tgt gct gtt tct cgc ttt ggt ggg aag gtt ctt gag aaa gcc     1072
Ala Asp Cys Ala Val Ser Arg Phe Gly Gly Lys Val Leu Glu Lys Ala
315                 320                 325                 330 aat tct gct tct cct gtg cat gag tat cca gcc ttg aac tgc aag agt     1120
```

```
                Asn Ser Ala Ser Pro Val His Glu Tyr Pro Ala Leu Asn Cys Lys Ser
                                335                 340                 345 ggg atg gaa ggg aat ggc ttg gtt tgc aaa aaa taa ttaagttgct               1166
Gly Met Glu Gly Asn Gly Leu Val Cys Lys Lys
            350                 355 acagagcatg ttgtatgctg aatgatgagc tataaataat tgagtttcag aaaagtctta       1226
ttagaaatga agtgatcata gctttacatg caaaaaaaaa aaaaaaaaaa aaaaaaaaa        1286 a                                                                       1287

CcDH2a complete sequence, including promoter (bases 1-1324; see
SEQ ID NO: 13), coding sequence (see SEQ ID NO: 3) and encoded
protein (see SEQ ID NO: 9) Intron I (1642)...(1866)
atagtgacct taatagcgat cttgttgctt ttgatcgtca gaaaagtagt ggacatgacg         60
gaagaggtcc taagatgagt tccagttcca gcatgaaggg ctctttggcg aagcctttct        120
tgaggcgtca cttttctttt ggatctaaag gcagtagatc aatgtcagag aatcattctt        180
cctggaagag gggattcttc tgggcaaaat cgagaaagga ttaagttctg tctagagtta        240
caaaggtgag caacagtcac ggttttttat tagggaatgg aaggattgga tcccttttca        300
cgtagtgaac aacatatatt ttgcatggtt ggtcttagta cctataacac gaaaatgttc        360
ttcatccgtt ctattaatca ttaggcttta gtcatttaaa ttttttacat cccgcatttc        420
tcctcttgat tcttgttgat ttctgcagat tccacagttg ttcttcagat gggctacgaa        480
atgcatgcag ggagcaggca atcagccata aattcaaccc tgtcaaggaa gctggcattg        540
tctcgtgcaa atgtaggtta gcttttgaag atacactgca aagggaagac catacagatg        600
gggaaatgaa ttcattataa ataggaaaa aggaaagatg ataggggtca gggcgtccgt         660
gcatcatgaa actagttctc tttcattttg tacgatggct gtttactgtt taatttcatg        720
aaattagttt ggatatatgc gtagcgtttt accatcgcat ttctaaatcg atattctatg        780
ggccgaatta cgcgttggag acatcattgg gttgctcctc tcaatcccat ctctatctat        840
tgacggatcc ggatcatgat gttgaacctt tcaactttg acttagatgg gatttgtgtt         900
cgcgtgttgt taacttgtta ctgaccgact cagaagacag cggattctga cttcaccacg        960
tgtctcttta gtgaaaattt aaaaggcatt tttcttctgt tcatagttta aaatgtaatg       1020
tgattattaa aagatcgttt ggtattattt caaggatgga tggattggat ggaagggata       1080
tctgatatat atcatacccct tccaaaaattc aggaccatga cgtatttaat atcccccagc    1140
ggaagacacg tgccttgatg tcttataggt ggcaatacac ttcagcttcc tctgctaata       1200
cgtgtgagga tcttcggtac catgcagaaa agaccgcggt gctccttcca ccgtcctcat       1260
ccctctcttg gcttttttaa gtctcctgcg atatccaaaa tccaaacaaa gccgttatcg       1320
cagctaaaat tcgtcaaccc caagtctcag gctaccttaa tttcagtgcc cttttctctt      1380
atttttttct aataacagga gtcctggaaa atg gct gac ttg cgt gat gaa tat        1434
                                    Ala Asp Leu Arg Asp Glu Tyr
                                     1               5 gga aat cct atg cag ttg acc gac cag tat ggc aac ccg gtt cag ctc         1482
Gly Asn Pro Met Gln Leu Thr Asp Gln Tyr Gly Asn Pro Val Gln Leu
        10                  15                  20 aag gac gag tat ggc aac cca atg cag ctt agc ggt gta gct atc acc         1530
Lys Asp Glu Tyr Gly Asn Pro Met Gln Leu Ser Gly Val Ala Ile Thr
    25                  30                  35 gcc ggg acg gct agt act gtc cat tct act gga acc gga cca act gct         1578
Ala Gly Thr Ala Ser Thr Val His Ser Thr Gly Thr Gly Pro Thr Ala
40                  45                  50                  55 gcc act gga acc cag caa cat cag gag cag ctt cat cgg tct agc agc         1626
Ala Thr Gly Thr Gln Gln His Gln Glu Gln Leu His Arg Ser Ser Ser
                60                  65                  70
```

-continued

```
tca agc tct ggc tcg gtgagatact tgccaagtta caatgtgtgt gtctgtgtgt   1681
Ser Ser Ser Gly Ser
            75 gtataatgcg ccatcataat tgtttgcttg acagatcctg ttaataatga accgtaattt   1741 gacgtaaagt gtcacgtttt tgtttttctg ggactaacat aatatcgaat caggctcctg   1801 ttgaatttga atgttgttag ctaaaagaaa attttggtgg ctgagttgtt gaatttggtt   1861 tatag acg gag gat gat gga caa gga gga aga aga aag aaa aaa ggg ttg   1911
      Thr Glu Asp Asp Gly Gln Gly Gly Arg Arg Lys Lys Lys Gly Leu
              80                  85                  90 aaa gaa aag ata aag gag aaa cta acg ggc ggt agg cac aag gac aga     1959
Lys Glu Lys Ile Lys Glu Lys Leu Thr Gly Gly Arg His Lys Asp Arg
             95                 100                 105 gac gat cag gag cac atc gat gat cag cac gcg cac agc gcc tct cct     2007
Asp Asp Gln Glu His Ile Asp Asp Gln His Ala His Ser Ala Ser Pro
         110                 115                 120 cca aca acc acc act ggc agc ggg acg tct act aca gtc ggg ggt cag     2055
Pro Thr Thr Thr Thr Gly Ser Gly Thr Ser Thr Thr Val Gly Gly Gln
     125                 130                 135 cag cat gaa aag aag agc atg gtg gag aag att atg gaa aag ctc cct     2103
Gln His Glu Lys Lys Ser Met Val Glu Lys Ile Met Glu Lys Leu Pro
140                 145                 150                 155 ggc cat cac gac acc cgc tagttaccta ccacaacata ctgtgatcat           2151
Gly His His Asp Thr Arg
                160 cgtgtaaaat ctctcctgat gcctaggaaa tctagattat gttaggcatt ttgtttggta   2211 tgtatgtgtg attaagacct tgttgtgcgc ttgaatcttg aacgtgcatg ggatttgctt   2271 ggtttgattt gatttgg                                                  2288
```

The present invention is not limited to the embodiments described and exemplified above, but is capable of variation and modification within the scope of the appended claims.

---

What is claimed:

1. A nucleic acid molecule isolated from coffee having a coding sequence that encodes a dehydrin protein, wherein the dehydrin protein comprises an amino acid sequence that is 90% or more identical to an amino acid sequence selected from the group consisting of SEQ ID NO: 7, SEQ ID NO: 8, SEQ ID NO: 9, SEQ ID NO: 10 and SEQ ID NO: 11.

2. The nucleic acid molecule of claim 1, wherein the encoded dehydrin protein has a molecular weight of between about 17 kDa and about 26 kDa.

3. The nucleic acid molecule of claim 1, wherein the dehydrin protein has an amino acid sequence selected from the group consisting of SEQ ID NO: 7, SEQ ID NO: 8, SEQ ID NO: 9, SEQ ID NO: 10 and SEQ ID NO: 11.

4. The nucleic acid molecule of claim 1, wherein the coding sequence comprises a nucleotide sequence selected from the group consisting of SEQ ID NO: 1, SEQ ID NO: 2, SEQ ID NO: 3, SEQ ID NO: 4 and SEQ ID NO: 5.

5. A vector comprising the nucleic acid molecule of claim 1.

6. The vector of claim 5, wherein the coding sequence of the nucleic acid molecule is operably linked to a constitutive promoter.

7. The vector of claim 5, wherein the coding sequence of the nucleic acid molecule is operably linked to an inducible promoter.

8. The vector of claim 5, wherein the coding sequence of the nucleic acid molecule is operably linked to a tissue specific promoter.

9. The vector of claim 8, wherein the tissue specific promoter is a seed specific promoter.

10. The vector of claim 9, wherein the seed specific promoter is a coffee seed specific promoter.

11. The vector of claim 10, wherein the coffee seed specific promoter is a dehydrin gene promoter.

12. The vector of claim 11, wherein the dehydrin gene promoter comprises SEQ ID NO:13.

13. A method of increasing tolerance to an osmotic stress in a plant comprising:
   (a) transforming a plant cell with a nucleic acid molecule according to claim 1;
   (b) expressing said dehydrin protein encoded by said nucleic acid molecule in the transformed plant cell of step (a); and
   (c) regenerating a transgenic plant from the transformed plant cell of step (b),
   wherein, expression of said dehydrin protein in the transformed plant results in increased tolerance to the osmotic stress in the transformed plant as compared to a wild type plant of the same species lacking said nucleic acid molecule.

* * * * *

SEQUENCE LISTING

<160> NUMBER OF SEQ ID NOS: 46

<210> SEQ ID NO 1
<211> LENGTH: 880
<212> TYPE: DNA
<213> ORGANISM: Coffea canephora

<400> SEQUENCE: 1

```
gtgggaagaa gtcctatcgg tctctgatct ttcacctttc gttaatttgt gttcgatatt    60
ctactcccgc tagtagttga aatttggcaa ttaagatggc gcaatacggg gctgaatatg   120
gcaaccaaaa gagccagtac gatgagtacg gaaacccagt tcgtcagaca gacgaatatg   180
gtaaccctgc ccgccatgga ggtaccatgg gtgattatgg aaccactggc actactggag   240
cctatggtgg cacaactgga gcacatggga cttatgcaac tggaaccacc ggcactaccg   300
gtaccggtgc atacgccacc cagcctggca ctgatgtggg gaaggagcac catggccttg   360
gtggcatgct tcatcgctct ggcagcggta gctctagctc gtccgaggat gatgggcaag   420
gcgggaggag gaagaagggg atgaaggaga agataaagga gaaactgcct ggcggtcaca   480
aggaggctca acctgacaa gaatattcga gtgctactgc agctcctgga tacgcgggg    540 aaggagtgca gcacgagaag aaaggaatta tggataaaat caaggagaaa ttaccagggg   600
```

```
gtcaccacaa ctgaagatct aattctaata aatattggtc cgattatgat attgtgtacc    660
cctgttttca atctcaatct cgttcgtgtc gcgtttgtgt tttctgagat ttgagtgtgt    720
ggacgtcttg agtttctgta attggaataa aagatgattc gtcttcgtct tcgtggactc    780
tgtagtgtgt ttgtccgtat attccggcgtc ttgtactcgg gtcatctggt catgtatgta    840
acatgttata tatcaaatac gtgaagtttt gcgttaaaaa                           880

<210> SEQ ID NO 2
<211> LENGTH: 901
<212> TYPE: DNA
<213> ORGANISM: Coffea canephora

<400> SEQUENCE: 2
gtgggaagaa gtcttatcgg tctctgatcc ttcacctttc gttaatctgt gttctatatt     60
ctacttccgc tagtagttga aatttggcaa ttaagatggc gcaatacggg gctgaatatg    120
gcaaccaaaa gagccagtac gatgagtacg gaaacccagt tcgtcagaca gacgaatatg    180
gtaaccctgc ccgccatgga ggtaccatgg gtgattatgg aaccactggc actactggag    240
cctatggtgg cacaactggg acagctggag cacatgggac ttatgcaact ggaaccaccg    300
gcactaccgg taccggtgca tatgccaccc agcctggcac tgatgtgggg aaggagcgcc    360
atggccttgg tggcatgctt catcgctctg gtagcggtag ctctagctcg tccgaggatg    420
atgggcaagg cgggaggagg aagaagggga tgaaggagaa gataaaggag aaactgcctg    480
gcggtcacaa ggaggctcaa cctggacaag aatattcgag tgctactgca gctcctggat    540
acggcgggga aggagagcag cacgagaaga aggaattat ggataaaatc aaggagaaat    600 taccagggg tcaccgcaac tgaagatcta attctaataa atattggatc caattatgat    660
atcgtgtacc cctgttttca atctcaatct cgttcgtgtc gcgtttgtgt cttctgagat    720
ttgagtgtgt gggcgtcttg agtttctgta atcggaataa agatgattcg tcttcgtctt    780
cgtcttcgtc ttcgtggact ctgtagtgtg tttgtccgta tattcggcgt cttgtactcg    840
ggtcatctgg tcatgtatgt aacatgttat atatcaaata cgtgaagttt tgcgttaaaa    900
a                                                                    901

<210> SEQ ID NO 3
<211> LENGTH: 761
<212> TYPE: DNA
<213> ORGANISM: Coffea canephora

<400> SEQUENCE: 3
ctaaaattcg tcaaccccaa gtctcaggct accttaattt cagtgccctt tttctttatt     60
tttttctaat aacaggagtc ctggaaaatg gctgacttgc gtgatgaata tggaaatcct    120
atgcagttga ccgaccagta tggcaacccg gttcagctca aggacgagta tggcaaccca    180
atgcagctta gcggtgtagc tatcaccgcc gggacggcta gtgctgtcca ttctactgga    240
accggaccaa ctgctgccac tggaacccag caacatcagg agcagcttca tcggtctagc    300
agctcaagct ctggctcgtc ggaggatgat ggacaaggag gaagaagaa gaaaaaggg    360 ttgaaagaaa agataaagga gaaactaacg ggcgggaggc acaaggacag agacgatcag    420
gagcacatcg atgatcagca cgcgcacagc gcctctcctc aacaaccac cactggcagc    480 gggacgtcta ctacagtcgg gggtcagcag catgaaaaga gagcatggt ggagaagatt    540 atggaaaagc tccctggcca tcacgacacc cgctagttac ctaccacaac atactgtgat    600
catcgtgtaa aatctctcct gatgcctagg aaatctagat tatgttaggc attttgtttg    660
```

```
gtatgtatgt gtgattaaga ccttgttgtg cgcttgaatc ttgaacgtgc atgggatttg    720
cttggtttga tttgatttgg tgaaataagt tgtactaaaa a                        761
```

<210> SEQ ID NO 4
<211> LENGTH: 959
<212> TYPE: DNA
<213> ORGANISM: Coffea canephora

<400> SEQUENCE: 4

```
ctaaaattcg tcaaccccaa gtctcaggct acccttaattt cagtgcccctt tttctttatt    60 tttttctaat aacaggagtc ctggaaaatg gctgacttgc gtgatgaata tggaaatcct    120
atgcagttga ccgaccagta tggcaacccg gttcagctca aggacgagta tggcaaccca    180
atgcagctta gcggtgtagc tatcaccgcc gggacggcta gtgctgtcca ttctactgga    240
accggaccaa ctgctgccac tggaacccag caacttcagg agcagcttca tcggtctagc    300
agctcaagct ctggctcggt gagatacttg ccaagttaca atgtgtgtgt ctgtgtgtgt    360
ataatgcgcc atcataattg tttgcttgac agatcctgtt aataatgaac cgtaatttga    420
cgtaaagtgt acacgttttg tttttctggg acttacataa tatcgaatca ggctcctgtt    480
gaatttgaat gttgttagct aaaagaaaat tttggtggct gagttgttga atttggttta    540
tggtcggagg atgatggaca aggaggaaga agaaagaaaa aagggttgaa agaaaagata    600
aaggagaaac taacgggcgg gaggcacaag gacagagacg atcaggagca catcgatgat    660
cagcacgcgc acagcgcctc tcctccaaca accaccactg gcagcgggac gtctactaca    720
gtcgggggtc agcagcatga aaagaagagc atggtggaga agattatgga aaagctccct    780
ggccatcacg acacccgcta gttacctacc acaacatact gtgatcatcg tgtaaaatct    840
ctcctgatgc ctaggaaatc tagattatgt taggcatttt gtttggtatg tatgtgtgat    900
taagaccttg ttgtgcgctt gaatcttgaa cgtgcatggg atttgcttgg tttgaaaaa    959
```

<210> SEQ ID NO 5
<211> LENGTH: 835
<212> TYPE: DNA
<213> ORGANISM: Coffea canephora

<400> SEQUENCE: 5

```
atttttttgct gtttcctgtt acattctgct ttacgtacat ccatcagcaa aatggccgag    60
tatgatcaga gtaacatcaa ggttgaggag ggatcagctg tcgaggccac ggatcgcgga    120
ctcttcaact tgggcaagaa agaggaagtg aagaagtgtg atcaaggcca ggccatctct    180
gcggagtttg atgagaaagt gcgtgtttct gaaccagaca aggaggaggg aaagaagcat    240
ggtggtcttc tcgagaagct ccaccgatct ggtagcagct ccagcagctc aagtgaggaa    300
gaagtagaag agggtggtga agaagaagaa aaaagaagg aaaagaaggg tttgaaggac    360
aagatcaagg agaagatatc gggtgataag aaggacgaag aaaaggttga aaaatgtgag    420
gaagacacgt ctatcccagt tgagaaatat gccgaaccgg cccatgcaga tgctgctcat    480
gaaccagagg agaaaaaggg cttcttagat aagatcaagg agaaactacc aggtggtggt    540
cagaagaaga ctgaggaagt cgcagcagca gcaccgcctc ctcctccggc agagtgcacc    600
gccactgaag gtgaggccaa ggataagaag ggattcttgg acaagatcaa ggagaagctc    660
cctggctacc atcccaagac tgaagaagag aaggaaaagg agaggaaaa agaaaaggag    720 gctggatgcc attaataaaa gagcaaagca aattaatagc agctttccag tgtgtcataa    780
ttttgcattt ggattaatac attttggagt ggcaatgatc tttttatttt aaaaa         835
```

-continued

<210> SEQ ID NO 6
<211> LENGTH: 1232
<212> TYPE: DNA
<213> ORGANISM: Coffea canephora

<400> SEQUENCE: 6

| | |
|---|---|
| acgaacatca tcggtaccag tttcctattc atacatcatc ttactagcac tgatgcaaaa | 60 |
| aatgactcct ctgagatgca tcaatttcat ttttctggcc ttttgggttc ctgctgtcct | 120 |
| cgcggtgatg gccgaaaaac ccctagttcc tacatcccta atccccaaac cccctccacc | 180 |
| gccatcgcca gtgaaaccat cagtacccgt gatacctgtc aaaccccgaa tcgtgagatg | 240 |
| ccgctccaca ttgtttcctc tctgcttcaa tatccccttc gtttgcccct tagactgtct | 300 |
| taccaactgt ttagtggact gtgtcacctg caaggcttac tgcagttgca actttcccgg | 360 |
| cgctgtttgt caggatccac gattcgttgg gggcgatggc aacacatttt acttccatgg | 420 |
| ccgcaaggat caggacttct gcctggtttc ggataccaat cttcatgtaa atggtcattt | 480 |
| cattggcaaa agaaaaccta atttgcgcag agacttcact tgggtgcagg ccattggaat | 540 |
| aatgttcgac gaccacagaa tcctcgtggc cgcaaaaagg acttcaacgt gggacgacaa | 600 |
| tgtggatcga ctcgctatat ccattgatgg aaatccgatt tccctcccca ctgaagaagg | 660 |
| atccaaatgg caacttccgg ccccgtccaa tgtcagtatc atgagaacaa gcaacaataa | 720 |
| cggacttgtg gttgaagccg tgaacaattt caggatcacc gccaatgtgg ttccaataac | 780 |
| agctcaagaa tcaaaagttc atggttatga cattactgat gaggattgct ttacccattt | 840 |
| ggagcttggg ttcaaattct tcaacatcac cgattcaact gatggagttc tgggacaaac | 900 |
| ctataggagc gattacgtga acaaaatgaa ggtgaatgcg gtaatgccag tcatgggcgg | 960 |
| tgaccgtaag tacttgactt cgggactttt tagtgccgat tgtgctgttt ctcgctttgg | 1020 |
| tgggaaggtt cttgagaaag ccaattctgc ttctcctgtg catgagtatc cagccttgaa | 1080 |
| ctgcaagagt gggatggaag ggaatggctt ggtttgcaaa aaataattaa gttgctacag | 1140 |
| agcatgttgt atgctgaatg atgagctata ataattgag tttcagaaaa gtcttattag | 1200 |
| aaatgaagtg atcatagctt tacatgcaaa aa | 1232 |

<210> SEQ ID NO 7
<211> LENGTH: 172
<212> TYPE: PRT
<213> ORGANISM: Coffea canephora

<400> SEQUENCE: 7

Met Ala Gln Tyr Gly Ala Glu Tyr Gly Asn Gln Lys Ser Gln Tyr Asp
1               5                   10                  15

Glu Tyr Gly Asn Pro Val Arg Gln Thr Asp Glu Tyr Gly Asn Pro Ala
            20                  25                  30

Arg His Gly Gly Thr Met Gly Asp Tyr Gly Thr Thr Gly Thr Thr Gly
        35                  40                  45

Ala Tyr Gly Gly Thr Thr Gly Ala His Gly Thr Tyr Ala Thr Gly Thr
    50                  55                  60

Thr Gly Thr Thr Gly Thr Gly Ala Tyr Ala Thr Gln Pro Gly Thr Asp
65                  70                  75                  80

Val Gly Lys Glu His His Gly Leu Gly Gly Met Leu His Arg Ser Gly
                85                  90                  95

Ser Gly Ser Ser Ser Ser Ser Glu Asp Asp Gly Gln Gly Gly Arg Arg
            100                 105                 110

Lys Lys Gly Met Lys Glu Lys Ile Lys Glu Lys Leu Pro Gly Gly His

```
            115                 120                 125
Lys Glu Ala Gln Pro Gly Gln Glu Tyr Ser Ser Ala Thr Ala Ala Pro
    130                 135                 140

Gly Tyr Gly Gly Glu Gly Val Gln His Glu Lys Lys Gly Ile Met Asp
145                 150                 155                 160

Lys Ile Lys Glu Lys Leu Pro Gly Gly His His Asn
                165                 170

<210> SEQ ID NO 8
<211> LENGTH: 175
<212> TYPE: PRT
<213> ORGANISM: Coffea canephora

<400> SEQUENCE: 8

Met Ala Gln Tyr Gly Ala Glu Tyr Gly Asn Gln Lys Ser Gln Tyr Asp
1               5                   10                  15

Glu Tyr Gly Asn Pro Val Arg Gln Thr Asp Glu Tyr Gly Asn Pro Ala
                20                  25                  30

Arg His Gly Gly Thr Met Gly Asp Tyr Gly Thr Thr Gly Thr Thr Gly
            35                  40                  45

Ala Tyr Gly Gly Thr Thr Gly Thr Ala Gly Ala His Gly Thr Tyr Ala
    50                  55                  60

Thr Gly Thr Thr Gly Thr Thr Gly Thr Gly Ala Tyr Ala Thr Gln Pro
65                  70                  75                  80

Gly Thr Asp Val Gly Lys Glu Arg His Gly Leu Gly Gly Met Leu His
                85                  90                  95

Arg Ser Gly Ser Gly Ser Ser Ser Ser Glu Asp Asp Gly Gln Gly
            100                 105                 110

Gly Arg Arg Lys Lys Gly Met Lys Glu Lys Ile Lys Glu Lys Leu Pro
    115                 120                 125

Gly Gly His Lys Glu Ala Gln Pro Gly Gln Glu Tyr Ser Ser Ala Thr
130                 135                 140

Ala Ala Pro Gly Tyr Gly Gly Glu Gly Glu Gln His Glu Lys Lys Gly
145                 150                 155                 160

Ile Met Asp Lys Ile Lys Glu Lys Leu Pro Gly Gly His Arg Asn
                165                 170                 175

<210> SEQ ID NO 9
<211> LENGTH: 162
<212> TYPE: PRT
<213> ORGANISM: Coffea canephora

<400> SEQUENCE: 9

Met Ala Asp Leu Arg Asp Glu Tyr Gly Asn Pro Met Gln Leu Thr Asp
1               5                   10                  15

Gln Tyr Gly Asn Pro Val Gln Leu Lys Asp Glu Tyr Gly Asn Pro Met
                20                  25                  30

Gln Leu Ser Gly Val Ala Ile Thr Ala Gly Thr Ala Ser Ala Val His
            35                  40                  45

Ser Thr Gly Thr Gly Pro Thr Ala Ala Thr Gly Thr Gln Gln His Gln
    50                  55                  60

Glu Gln Leu His Arg Ser Ser Ser Ser Gly Ser Ser Glu Asp
65                  70                  75                  80

Asp Gly Gln Gly Gly Arg Arg Lys Lys Gly Leu Lys Glu Lys Ile
                85                  90                  95

Lys Glu Lys Leu Thr Gly Gly Arg His Lys Asp Arg Asp Asp Gln Glu
            100                 105                 110
```

His Ile Asp Asp Gln His Ala His Ser Ala Ser Pro Pro Thr Thr Thr
            115                 120                 125

Thr Gly Ser Gly Thr Ser Thr Thr Val Gly Gly Gln Gln His Glu Lys
        130                 135                 140

Lys Ser Met Val Glu Lys Ile Met Glu Lys Leu Pro Gly His His Asp
145                 150                 155                 160

Thr Arg

<210> SEQ ID NO 10
<211> LENGTH: 162
<212> TYPE: PRT
<213> ORGANISM: Coffea canephora

<400> SEQUENCE: 10

Met Ala Asp Leu Arg Asp Glu Tyr Gly Asn Pro Met Gln Leu Thr Asp
1               5                   10                  15

Gln Tyr Gly Asn Pro Val Gln Leu Lys Asp Glu Tyr Gly Asn Pro Met
            20                  25                  30

Gln Leu Ser Gly Val Ala Ile Thr Ala Gly Thr Ala Ser Ala Val His
        35                  40                  45

Ser Thr Gly Thr Gly Pro Thr Ala Ala Thr Gly Thr Gln Gln Leu Gln
50                  55                  60

Glu Gln Leu His Arg Ser Ser Ser Ser Gly Ser Ser Glu Asp
65                  70                  75                  80

Asp Gly Gln Gly Gly Arg Arg Lys Lys Lys Gly Leu Lys Glu Lys Ile
                85                  90                  95

Lys Glu Lys Leu Thr Gly Gly Arg His Lys Asp Arg Asp Asp Gln Glu
            100                 105                 110

His Ile Asp Asp Gln His Ala His Ser Ala Ser Pro Pro Thr Thr Thr
            115                 120                 125

Thr Gly Ser Gly Thr Ser Thr Thr Val Gly Gly Gln Gln His Glu Lys
        130                 135                 140

Lys Ser Met Val Glu Lys Ile Met Glu Lys Leu Pro Gly His His Asp
145                 150                 155                 160

Thr Arg

<210> SEQ ID NO 11
<211> LENGTH: 227
<212> TYPE: PRT
<213> ORGANISM: Coffea canephora

<400> SEQUENCE: 11

Met Ala Glu Tyr Asp Gln Ser Asn Ile Lys Val Glu Glu Gly Ser Ala
1               5                   10                  15

Val Glu Ala Thr Asp Arg Gly Leu Phe Asn Leu Gly Lys Lys Glu Glu
            20                  25                  30

Val Lys Lys Cys Asp Gln Gly Gln Ala Ile Ser Ala Glu Phe Asp Glu
        35                  40                  45

Lys Val Arg Val Ser Glu Pro Asp Lys Glu Gly Lys His Gly
50                  55                  60

Gly Leu Leu Glu Lys Leu His Arg Ser Gly Ser Ser Ser Ser Ser
65                  70                  75                  80

Ser Glu Glu Glu Val Glu Glu Gly Gly Glu Lys Lys Lys Lys Lys
                85                  90                  95

Glu Lys Lys Gly Leu Lys Asp Lys Ile Lys Glu Lys Ile Ser Gly Asp
            100                 105                 110

Lys Lys Asp Glu Glu Lys Val Glu Lys Cys Glu Glu Asp Thr Ser Ile
            115                 120                 125

Pro Val Glu Lys Tyr Ala Glu Pro Ala His Ala Asp Ala Ala His Glu
130                 135                 140

Pro Glu Glu Lys Lys Gly Phe Leu Asp Lys Ile Lys Glu Lys Leu Pro
145                 150                 155                 160

Gly Gly Gly Gln Lys Lys Thr Glu Glu Val Ala Ala Ala Pro Pro
                165                 170                 175

Pro Pro Pro Ala Glu Cys Thr Ala Thr Glu Gly Glu Ala Lys Asp Lys
            180                 185                 190

Lys Gly Phe Leu Asp Lys Ile Lys Glu Lys Leu Pro Gly Tyr His Pro
            195                 200                 205

Lys Thr Glu Glu Glu Lys Glu Lys Glu Lys Glu Lys Glu Lys Glu Ala
210                 215                 220

Gly Cys His
225

<210> SEQ ID NO 12
<211> LENGTH: 357
<212> TYPE: PRT
<213> ORGANISM: Coffea canephora

<400> SEQUENCE: 12

Met Gln Lys Met Thr Pro Leu Arg Cys Ile Asn Phe Ile Phe Leu Ala
1               5                   10                  15

Phe Trp Val Pro Ala Val Leu Ala Val Met Ala Glu Lys Pro Leu Val
            20                  25                  30

Pro Thr Tyr Leu Ile Pro Lys Pro Pro Pro Pro Ser Pro Val Lys
            35                  40                  45

Pro Ser Val Pro Val Ile Pro Val Lys Pro Arg Ile Val Arg Cys Arg
50                  55                  60

Ser Thr Leu Phe Pro Leu Cys Phe Asn Ile Pro Phe Val Cys Pro Leu
65                  70                  75                  80

Asp Cys Leu Thr Asn Cys Leu Val Asp Cys Val Thr Cys Lys Ala Tyr
                85                  90                  95

Cys Ser Cys Asn Phe Pro Gly Ala Val Cys Gln Asp Pro Arg Phe Val
            100                 105                 110

Gly Gly Asp Gly Asn Thr Phe Tyr Phe His Gly Arg Lys Asp Gln Asp
            115                 120                 125

Phe Cys Leu Val Ser Asp Thr Asn Leu His Val Asn Gly His Phe Ile
130                 135                 140

Gly Lys Arg Lys Pro Asn Leu Arg Arg Asp Phe Thr Trp Val Gln Ala
145                 150                 155                 160

Ile Gly Ile Met Phe Asp Asp His Arg Ile Leu Val Ala Ala Lys Arg
                165                 170                 175

Thr Ser Thr Trp Asp Asp Asn Val Asp Arg Leu Ala Ile Ser Ile Asp
            180                 185                 190

Gly Asn Pro Ile Ser Leu Pro Thr Glu Glu Gly Ser Lys Trp Gln Leu
            195                 200                 205

Pro Ala Pro Ser Asn Val Ser Ile Met Arg Thr Ser Asn Asn Asn Gly
210                 215                 220

Leu Val Val Glu Ala Val Asn Asn Phe Arg Ile Thr Ala Asn Val Val
225                 230                 235                 240

Pro Ile Thr Ala Gln Glu Ser Lys Val His Gly Tyr Asp Ile Thr Asp
                245                 250                 255

```
Glu Asp Cys Phe Thr His Leu Glu Leu Gly Phe Lys Phe Asn Ile
            260                 265                 270

Thr Asp Ser Thr Asp Gly Val Leu Gly Gln Thr Tyr Arg Ser Asp Tyr
275                 280                 285

Val Asn Lys Met Lys Val Asn Ala Val Met Pro Val Met Gly Gly Asp
    290                 295                 300

Arg Lys Tyr Leu Thr Ser Gly Leu Phe Ser Ala Asp Cys Ala Val Ser
305                 310                 315                 320

Arg Phe Gly Gly Lys Val Leu Glu Lys Ala Asn Ser Ala Ser Pro Val
                325                 330                 335

His Glu Tyr Pro Ala Leu Asn Cys Lys Ser Gly Met Glu Gly Asn Gly
            340                 345                 350

Leu Val Cys Lys Lys
        355

<210> SEQ ID NO 13
<211> LENGTH: 2288
<212> TYPE: DNA
<213> ORGANISM: Coffea canephora
<220> FEATURE:
<221> NAME/KEY: Promoter
<222> LOCATION: (1)..(1324)
<223> OTHER INFORMATION: Promoter of CcDH2a
<220> FEATURE:
<221> NAME/KEY: exon
<222> LOCATION: (1414)..(1641)
<223> OTHER INFORMATION: Exon I of CcDH2a
<220> FEATURE:
<221> NAME/KEY: Intron
<222> LOCATION: (1642)..(1866)
<220> FEATURE:
<221> NAME/KEY: exon
<222> LOCATION: (1867)..(2121)
<223> OTHER INFORMATION: Exon II of CcDH2a

<400> SEQUENCE: 13
atagtgacct taatagcgat cttgttgctt ttgatcgtca gaaaagtagt ggacatgacg      60
gaagaggtcc taagatgagt tccagttcca gcatgaaggg ctctttggcg aagcctttct     120
tgaggcgtca cttttctttt ggatctaaag gcagtagatc aatgtcagag aatcattctt     180
cctggaagag gggattcttc tgggcaaaat cgagaaagga ttaagttctg tctagagtta     240
caaaggtgag caacagtcac ggttttttat tagggaatgg aaggattgga tcccttttca     300
cgtagtgaac aacatatatt ttgcatggtt ggtcttagta cctataacac gaaaatgttc     360
ttcatccgtt ctattaatca ttaggcttta gtcatttaaa ttttttacat cccgcatttc     420
tcctcttgat tcttgttgat ttctgcagat tccacagttg ttcttcagat gggctacgaa     480
atgcatgcag ggagcaggca atcagccata aattcaaccc tgtcaaggaa gctggcattg     540
tctcgtgcaa atgtaggtta gcttttgaag atacactgca aagggaagac catacagatg     600
gggaaatgaa ttcattataa tataggaaaa aggaaagatg ataggggtca gggcgtccgt     660
gcatcatgaa actagttctc tttcattttg tacgatggct gtttactgtt taatttcatg     720
aaattagttt ggatatatgc gtagcgtttt accatcgcat ttctaaatcg atattctatg     780
ggccgaatta cgcgttggag acatcattgg gttgctcctc tcaatcccat ctctatctat     840
tgacggatcc ggatcatgat gttgaacctt tcaactttg acttagatgg gatttgtgtt     900
cgcgtgttgt taacttgtta ctgaccgact cagaagacag cggattctga cttcaccacg     960
tgtctcttta gtgaaaattt aaaaggcatt tttcttctgt tcatagttta aaatgtaatg    1020
tgattattaa aagatcgttt ggtattattt caaggatgga tggattggat ggaagggata    1080
```

```
tctgatatat atcataccct tccaaaattc aggaccatga cgtatttaat atcccccagc    1140
ggaagacacg tgccttgatg tcttataggt ggcaatacac ttcagcttcc tctgctaata    1200
cgtgtgagga tcttcggtac catgcagaaa agaccgcggt gctccttcca ccgtcctcat    1260
ccctctcttg gctttttaa gtctcctgcg atatccaaaa tccaaacaaa gccgttatcg     1320
cagctaaaat tcgtcaaccc caagtctcag gctaccttaa tttcagtgcc ctttttcttt    1380
atttttttct aataacagga gtcctggaaa atg gct gac ttg cgt gat gaa tat    1434
                                  Ala Asp Leu Arg Asp Glu Tyr
                                   1               5 gga aat cct atg cag ttg acc gac cag tat ggc aac ccg gtt cag ctc    1482
Gly Asn Pro Met Gln Leu Thr Asp Gln Tyr Gly Asn Pro Val Gln Leu
         10                  15                  20 aag gac gag tat ggc aac cca atg cag ctt agc ggt gta gct atc acc    1530
Lys Asp Glu Tyr Gly Asn Pro Met Gln Leu Ser Gly Val Ala Ile Thr
     25                  30                  35 gcc ggg acg gct agt act gtc cat tct act gga acc gga cca act gct    1578
Ala Gly Thr Ala Ser Thr Val His Ser Thr Gly Thr Gly Pro Thr Ala
 40                  45                  50                  55 gcc act gga acc cag caa cat cag gag cag ctt cat cgg tct agc agc    1626
Ala Thr Gly Thr Gln Gln His Gln Glu Gln Leu His Arg Ser Ser Ser
                 60                  65                  70 tca agc tct ggc tcg gtgagatact tgccaagtta caatgtgtgt gtctgtgtgt    1681
Ser Ser Ser Gly Ser
             75 gtataatgcg ccatcataat tgtttgcttg acagatcctg ttaataatga accgtaattt    1741 gacgtaaagt gtacacgttt tgtttttctg ggactaacat aatatcgaat caggctcctg    1801 ttgaatttga atgttgttag ctaaaagaaa attttggtgg ctgagttgtt gaatttggtt    1861 tatag acg gag gat gat gga caa gga gga aga aga aag aaa aaa ggg ttg    1911
      Thr Glu Asp Asp Gly Gln Gly Gly Arg Arg Lys Lys Lys Gly Leu
           80                  85                  90 aaa gaa aag ata aag gag aaa cta acg ggc ggt agg cac aag gac aga    1959
Lys Glu Lys Ile Lys Glu Lys Leu Thr Gly Gly Arg His Lys Asp Arg
95                 100                 105 gac gat cag gag cac atc gat gat cag cac gcg cac agc gcc tct cct    2007
Asp Asp Gln Glu His Ile Asp Asp Gln His Ala His Ser Ala Ser Pro
                 110                 115                 120 cca aca acc acc act ggc agc ggg acg tct act aca gtc ggg ggt cag    2055
Pro Thr Thr Thr Thr Gly Ser Gly Thr Ser Thr Thr Val Gly Gly Gln
             125                 130                 135 cag cat gaa aag aag agc atg gtg gag aag att atg gaa aag ctc cct    2103
Gln His Glu Lys Lys Ser Met Val Glu Lys Ile Met Glu Lys Leu Pro
140                 145                 150                 155 ggc cat cac gac acc cgc tagttaccta ccacaacata ctgtgatcat            2151
Gly His His Asp Thr Arg
                 160 cgtgtaaaat ctctcctgat gcctaggaaa tctagattat gttaggcatt tgtttggta    2211 tgtatgtgtg attaagacct tgttgtgcgc ttgaatcttg aacgtgcatg ggatttgctt    2271 ggtttgattt gatttgg                                                  2288

<210> SEQ ID NO 14
<211> LENGTH: 130
<212> TYPE: PRT
<213> ORGANISM: Lycopersicon esculentum

<400> SEQUENCE: 14

Met Ala Gln Tyr Gly Asn Gln Asp Gln Met Arg Lys Thr Asp Glu Tyr
```

```
1               5                   10                  15
Gly Asn His Val Gln Glu Thr Gly Val Tyr Gln Gly Thr Gly Thr Gly
             20                  25                  30

Gly Met Met Gly Gly Thr Gly Thr Gly Gly Met Met Gly Gly Thr Gly
             35                  40                  45

Gly Glu Tyr Gly Thr Gln Gly Met Gly Thr Gly Thr His His His Glu
             50                  55                  60

Gly Gln Gln Gln Leu Arg Arg Ser Asp Ser Ser Ser Ser Ser Glu Asp
65                   70                  75                  80

Asp Gly Glu Gly Gly Arg Arg Lys Lys Gly Leu Lys Glu Lys Ile Met
             85                  90                  95

Glu Lys Met Pro Gly Gln His Glu Gly Glu Tyr Gly Gln Thr Thr Gly
             100                 105                 110

Glu Glu Lys Lys Gly Met Met Asp Lys Ile Lys Asp Lys Ile Pro Gly
             115                 120                 125

Met His
    130
```

<210> SEQ ID NO 15
<211> LENGTH: 157
<212> TYPE: PRT
<213> ORGANISM: Solanum commersonii

<400> SEQUENCE: 15

```
Met Ala His Tyr Glu Asn Gln Tyr Ser Ala Gly Gln Ala Leu Gln Lys
1               5                   10                  15

Asp Glu Tyr Gly Asn Pro Val Arg Gln Thr Asp Glu Tyr Gly Asn Pro
             20                  25                  30

Ile Gln Gln Thr Gly Gly Thr Met Gly Glu Tyr Gly Thr Gly Thr Gly Thr
             35                  40                  45

Gly Tyr Gly Thr Gln Ala Gly His Thr Thr Gly Val Leu Gly Gly Asp
             50                  55                  60

Gln Arg Gln His Gly Thr Leu Gly Gly Met Leu His Arg Ser Gly Ser
65                   70                  75                  80

Ser Ser Ser Ser Ser Ser Glu Asp Asp Gly His Gly Gly Arg Arg
             85                  90                  95

Lys Lys Lys Gly Ile Lys Asp Lys Val Lys Glu Lys Leu Pro Gly Gly
             100                 105                 110

His Arg Asp Asp Leu Ala His Ser Thr Ala Thr Thr Thr Thr Thr Gly
             115                 120                 125

Tyr Gly Met Asp Gly Thr His Glu Lys Lys Gly Ile Met Glu Lys Ile
             130                 135                 140

Lys Glu Lys Leu Pro Gly His His Gly Pro Gly His His
145                 150                 155
```

<210> SEQ ID NO 16
<211> LENGTH: 186
<212> TYPE: PRT
<213> ORGANISM: Arabidopsis thaliana

<400> SEQUENCE: 16

```
Met Ala Ser Tyr Gln Asn Arg Pro Gly Gly Gln Ala Thr Asp Glu Tyr
1               5                   10                  15

Gly Asn Pro Ile Gln Gln Gln Tyr Asp Glu Tyr Gly Asn Pro Met Gly
             20                  25                  30

Gly Gly Gly Tyr Gly Thr Gly Gly Gly Gly Ala Thr Gly Gly Gln
             35                  40                  45
```

Gly Tyr Gly Thr Gly Gly Gln Gly Tyr Gly Ser Gly Gly Gln Gly Tyr
             50                  55                  60
Gly Thr Gly Gly Gln Gly Tyr Gly Thr Gly Thr Gly Thr Glu Gly Phe
 65                  70                  75                  80
Gly Thr Gly Gly Ala Arg His His Gly Gln Glu Gln Leu His Lys
                 85                  90                  95
Glu Ser Gly Gly Leu Gly Gly Met Leu His Arg Ser Gly Ser Gly
            100                 105                 110
Ser Ser Ser Ser Ser Glu Asp Asp Gly Gln Gly Gly Arg Arg Lys Lys
            115                 120                 125
Gly Ile Thr Gln Lys Ile Lys Glu Lys Leu Pro Gly His His Asp Gln
130                 135                 140
Ser Gly Gln Ala Gln Ala Met Gly Gly Met Gly Ser Gly Tyr Asp Ala
145                 150                 155                 160
Gly Gly Tyr Gly Gly Glu His His Glu Lys Lys Gly Met Met Asp Lys
                165                 170                 175
Ile Lys Glu Lys Leu Pro Gly Gly Gly Arg
            180                 185

<210> SEQ ID NO 17
<211> LENGTH: 208
<212> TYPE: PRT
<213> ORGANISM: Nicotiana tabacum

<400> SEQUENCE: 17

Met Ala Asp Gln Tyr Glu Lys Lys Val Glu Glu Gly Ser Ala Asn Val
  1               5                  10                  15
Glu Ala Thr Asp Arg Gly Leu Phe Asp Phe Leu Gly Lys Lys Glu Glu
             20                  25                  30
Glu Lys Pro Thr His Ala Gln Glu Glu His Ala Ile Ser Ser Glu Phe
         35                  40                  45
Val Glu Lys Val Lys Val Ser Glu Glu Val Ala Glu Tyr Lys Glu Glu
 50                  55                  60
Glu Lys Lys Glu Glu His Asn Lys Glu Lys Lys Leu His Arg Ser
 65                  70                  75                  80
Ser Ser Ser Ser Ser Ser Ser Asp Glu Glu Glu Ile Gly Glu
             85                  90                  95
Asp Gly Gln Lys Ile Lys Lys Lys Lys Gly Leu Lys Asp Lys
            100                 105                 110
Ile Lys Asp Lys Ile Ser Gly Glu His Lys Glu Glu Lys Ala Gly
            115                 120                 125
Glu Asp Thr Ala Val Pro Val Glu Lys Tyr Glu Glu Thr Glu Glu Lys
130                 135                 140
Lys Gly Phe Leu Asp Lys Ile Lys Glu Lys Leu Pro Gly Gly Gln
145                 150                 155                 160
Lys Lys Thr Glu Glu Val Ala Pro Pro Pro Ala Ala Glu His
            165                 170                 175
Glu Ala Glu Gly Lys Glu Lys Lys Gly Phe Leu Asp Lys Ile Lys Glu
            180                 185                 190
Lys Leu Pro Gly Tyr His Ser Lys Thr Glu Glu Lys Lys Lys Lys
            195                 200                 205

<210> SEQ ID NO 18
<211> LENGTH: 209
<212> TYPE: PRT
<213> ORGANISM: Solanum tuberosum

<400> SEQUENCE: 18

```
Met Ala Asp Gln Tyr Glu Gln Asn Lys Pro Ser Val Glu Glu Thr Val
1               5                   10                  15

Gly Ala Asn Val Glu Ala Thr Asp Arg Gly Leu Phe Asp Phe Ile Gly
            20                  25                  30

Lys Lys Lys Glu Glu Lys Pro Ser His Ala His Glu Glu Glu Ala Ile
        35                  40                  45

Ser Ser Glu Phe Cys Glu Lys Val Lys Val Ser Glu Glu His Lys
    50                  55                  60

Glu Glu Glu Lys Lys Glu Lys Lys Leu His Arg Ser Ser Ser
65                  70                  75                  80

Ser Ser Ser Ser Ser Asp Glu Glu Glu Ile Gly Glu Asp Gly Gln
                85                  90                  95

Ile Ile Lys Lys Lys Lys Lys Gly Leu Lys Glu Lys Ile Lys Glu
            100                 105                 110

Lys Ile Ser Gly Asp His Lys Glu Glu Val Lys Thr Glu Asp Thr Ser
        115                 120                 125

Val Pro Val Glu Lys Tyr Glu Glu Thr Glu Glu Lys Lys Gly Phe Leu
    130                 135                 140

Asp Lys Ile Lys Glu Lys Leu Pro Gly Gly Gly His Lys Lys Thr Glu
145                 150                 155                 160

Glu Val Ala Ala Pro Pro Pro Pro Ala Ala Val Glu His Glu
                165                 170                 175

Ala Glu Gly Lys Glu Lys Lys Gly Phe Leu Asp Lys Ile Lys Glu Lys
            180                 185                 190

Leu Pro Gly Tyr His Ser Lys Thr Glu Glu Glu Lys Glu Lys Glu Lys
        195                 200                 205

Asn
```

<210> SEQ ID NO 19
<211> LENGTH: 265
<212> TYPE: PRT
<213> ORGANISM: Arabidopsis thaliana

<400> SEQUENCE: 19

```
Met Ala Glu Glu Tyr Lys Asn Asn Val Lys Glu His Glu Thr Pro Thr
1               5                   10                  15

Val Ala Thr Glu Glu Ser Pro Ala Thr Thr Glu Val Thr Asp Arg
            20                  25                  30

Gly Leu Phe Asp Phe Leu Gly Lys Lys Glu Glu Glu Lys Pro Gln
        35                  40                  45

Glu Thr Thr Thr Leu Glu Ser Glu Phe Asp His Lys Ala Gln Ile Ser
    50                  55                  60

Glu Pro Glu Leu Ala Ala Glu His Glu Val Lys Glu Asn Lys Ile
65                  70                  75                  80

Thr Leu Leu Glu Glu Leu Gln Glu Lys Thr Glu Glu Asp Glu Glu Asn
                85                  90                  95

Lys Pro Ser Val Ile Glu Lys Leu His Arg Ser Asn Ser Ser Ser
            100                 105                 110

Ser Ser Ser Asp Glu Glu Gly Glu Lys Lys Glu Lys Lys Lys Lys
        115                 120                 125

Ile Val Glu Gly Glu Glu Asp Lys Lys Gly Leu Val Glu Lys Ile Lys
    130                 135                 140

Glu Lys Leu Pro Gly His His Asp Lys Thr Ala Glu Asp Val Pro
145                 150                 155                 160
```

Val Ser Thr Thr Ile Pro Val Pro Val Ser Glu Ser Val Val Glu His
            165                 170                 175

Asp His Pro Glu Glu Lys Lys Gly Leu Val Glu Lys Ile Lys Glu
            180                 185                 190

Lys Leu Pro Gly His His Asp Glu Lys Ala Glu Asp Ser Pro Ala Val
            195                 200                 205

Thr Ser Thr Pro Leu Val Val Thr Glu His Pro Val Glu Pro Thr Thr
210                 215                 220

Glu Leu Pro Val Glu His Pro Glu Glu Lys Lys Gly Ile Leu Glu Lys
225                 230                 235                 240

Ile Lys Glu Lys Leu Pro Gly Tyr His Ala Lys Thr Thr Glu Glu Glu
            245                 250                 255

Val Lys Lys Glu Lys Glu Ser Asp Asp
            260                 265

<210> SEQ ID NO 20
<211> LENGTH: 337
<212> TYPE: PRT
<213> ORGANISM: Arabidopsis thaliana

<400> SEQUENCE: 20

Met Glu Ile Ser Lys Thr Leu Leu Val Ile Ser Leu Val Ala Ala
1               5                   10                  15

Thr Cys Phe Leu Gln Ala Lys Ala Ala Gly Val Tyr Cys Ser Asn Pro
            20                  25                  30

Tyr Thr Arg Cys Tyr Arg Lys Tyr Ile Arg Cys Pro Glu Glu Cys Pro
            35                  40                  45

Ser Lys Thr Ala Met Asn Ser Lys Asn Lys Val Cys Tyr Ala Asp Cys
50                  55                  60

Asp Arg Pro Thr Cys Lys Ser Gln Cys Arg Met Arg Lys Pro Asn Cys
65              70                  75                  80

Asn Arg Pro Gly Ser Ala Cys Tyr Asp Pro Arg Phe Ile Gly Gly Asp
            85                  90                  95

Gly Ile Val Phe Tyr Phe His Gly Lys Ser Asn Glu Glu Phe Ser Leu
            100                 105                 110

Val Ser Asp Ser Asp Leu Gln Ile Asn Gly Arg Phe Ile Gly His Arg
            115                 120                 125

Pro Ala Gly Arg Ala Arg Asp Phe Thr Trp Ile Gln Ala Leu Gly Phe
            130                 135                 140

Leu Phe Asn Ser Asn Lys Phe Ser Leu Glu Ala Lys Thr Ala Ser
145                 150                 155                 160

Trp Asp Asn Glu Ile Asp His Leu Lys Phe Ser Tyr Asp Gly Gln Asp
            165                 170                 175

Leu Ser Val Pro Glu Glu Thr Leu Ser Thr Trp Tyr Ser Pro Asn Lys
            180                 185                 190

Asp Ile Lys Ile Glu Arg Val Ser Met Arg Asn Ser Val Ile Val Thr
            195                 200                 205

Ile Lys Asp Lys Ala Glu Ile Met Ile Asn Val Pro Val Thr Lys
            210                 215                 220

Glu Asp Asp Arg Ile His Ser Tyr Lys Val Pro Ser Asp Cys Phe
225                 230                 235                 240

Ala His Leu Glu Val Gln Phe Arg Phe Phe Asn Leu Ser Pro Lys Val
            245                 250                 255

Asp Gly Ile Leu Gly Arg Thr Tyr Arg Pro Asp Phe Gln Asn Pro Ala
            260                 265                 270

```
Lys Pro Gly Val Ala Met Pro Val Gly Gly Glu Asp Ser Phe Lys
        275                 280                 285

Thr Ser Ser Leu Leu Ser Asn Asp Cys Lys Thr Cys Ile Phe Ser Glu
290                 295                 300

Ser Gln Ala Glu Ile Asp Ser Val Lys Ser Glu Ile Glu Tyr Ala Thr
305                 310                 315                 320

Leu Asp Cys Thr Arg Gly Ala Ser Ser Gly Tyr Gly Ile Val Cys Arg
                325                 330                 335

Lys

<210> SEQ ID NO 21
<211> LENGTH: 320
<212> TYPE: PRT
<213> ORGANISM: Picea glauca

<400> SEQUENCE: 21

Met Ala Ala Asn Lys Leu Met Asn Val Val Val Ala Val Cys Val
1               5                   10                  15

Met Val Met Val Asn Ala Ala Ser Ala Val Gly Lys Ala Lys Cys Thr
                20                  25                  30

Asp Lys Trp Tyr Pro Arg Cys Tyr Gly Tyr Gln Tyr Asp Cys Pro Ala
            35                  40                  45

Asn Cys Pro Tyr Asn Cys Asp Met Asp Cys Lys Thr Cys Lys Thr Val
50                  55                  60

Cys Pro Cys Asp Lys Pro Gly Val Cys Gln Asp Pro Arg Phe Ile
65                  70                  75                  80

Gly Gly Asp Gly Ile Met Phe Tyr Phe His Gly Lys Arg Asp Gln Asp
                85                  90                  95

Phe Cys Leu Ile Ser Asp Ser Asn Leu His Ile Asn Ala His Phe Ile
            100                 105                 110

Gly Lys Arg Gly Gln Gly Met Gly Arg Asp Phe Thr Trp Val Gln Ser
        115                 120                 125

Ile Gly Val Leu Leu Glu Asp Gly Arg Gln Phe Tyr Leu Gly Ala Lys
130                 135                 140

Lys Val Ser Thr Trp Asp Asn Ser Val Asp Gln Leu Thr Met Ala Leu
145                 150                 155                 160

Asn Gly Gln Thr Leu Thr Leu Pro Pro Gly Glu Gly Ala Thr Trp Ala
                165                 170                 175

Thr Ala Ser Gly Leu Asn Val Thr Arg Ser Asp Arg Ala Asn Glu Val
            180                 185                 190

Val Val Gln Val Glu Asp Lys Leu Lys Ile Ser Ala Arg Val Val Pro
        195                 200                 205

Ile Ser Glu Glu Glu Ser Arg Val His Asn Tyr Gly Ile Ile Ala Gly
210                 215                 220

Glu Asp Cys Phe Ala His Leu Glu Leu Ser Phe Lys Tyr Ser Leu
225                 230                 235                 240

Ser Pro Asn Val Ser Gly Val Leu Gly Gln Thr Tyr Gly Ala Glu Tyr
                245                 250                 255

Arg Ser Pro Val Lys Met Gly Val Ala Met Pro Ile Met Gly Gly Glu
            260                 265                 270

Ser Asn Tyr Val Thr Ser Asn Leu Phe Ala Ala Asp Cys Lys Val Ala
        275                 280                 285

Arg Phe Ala Ser Ser Ser Asp Asp Glu Tyr Ala Ile Thr Ser Ala Leu
290                 295                 300
```

```
Asp Cys Asn Ser Gly Arg Gly Ser Gly His Gly Ile Val Ser Arg Arg
305                 310                 315                 320
```

<210> SEQ ID NO 22
<211> LENGTH: 349
<212> TYPE: PRT
<213> ORGANISM: Zea mays

<400> SEQUENCE: 22

```
Met Ala Arg Leu Gly Ala Leu Ile Pro Leu Ala Ile Val Leu Leu Ala
1               5                   10                  15

Ala Val Ala Ala Thr Ala Ala Pro Ser Asp Arg Pro Pro Lys Ala Gln
            20                  25                  30

Gly Pro Lys Pro His Lys Glu Lys Glu Lys Glu Lys Pro Lys Pro Met
        35                  40                  45

Lys Val Lys Cys Arg Pro Arg Lys Leu Tyr Pro Tyr Cys Pro Gly Lys
    50                  55                  60

Pro Met Glu Cys Pro Ala Glu Cys Ser Gln Ser Cys Tyr Ala Asp Cys
65                  70                  75                  80

Ser Ser Cys Lys Pro Val Cys Val Cys Ser Val Pro Gly Ala Cys Gly
                85                  90                  95

Asp Pro Arg Phe Ile Gly Gly Asp Gly Asn Ala Phe Tyr Phe His Gly
            100                 105                 110

Arg Arg Asp Ala Asp Phe Cys Val Leu Ser Asp Arg Asp Leu His Ile
        115                 120                 125

Asn Ala His Phe Ile Gly Lys His Gly Ala Asp Gly Met Ser Arg Asp
    130                 135                 140

Phe Thr Trp Ile Gln Ala Ile Ala Val Leu Phe Asp Gly His Glu Leu
145                 150                 155                 160

Tyr Val Gly Ala Arg Lys Thr Ala Ala Trp Asp Asp Val Asp Arg
                165                 170                 175

Met Glu Leu Thr Leu Asp Gly Glu Pro Val Arg Leu Leu Pro Gly Thr
            180                 185                 190

Asp Ala Ala Trp Thr Ser Gly Ala Val Pro Ala Leu Ser Val Thr Arg
        195                 200                 205

Thr Ser Ala Ala Asn Gly Val Leu Val Ser Leu Asp Gly Arg Phe Thr
    210                 215                 220

Ile Arg Ala Asn Ala Val Pro Ile Thr Glu Glu Ser Arg Val His
225                 230                 235                 240

Arg Tyr Gly Val Thr Ala Asp Asp Cys Leu Ala His Leu Asp Leu Ala
                245                 250                 255

Phe Lys Phe Gly Ala Leu Thr Ala Asp Val His Gly Val Val Gly Gln
            260                 265                 270

Thr Tyr Arg Ser Asp Tyr Val Asn Arg Phe Asp Val Lys Ala Ser Met
        275                 280                 285

Pro Thr Met Gly Gly Asp Ser Asn Tyr Thr Thr Ser Ser Leu Phe Ala
    290                 295                 300

Ala Asp Cys Ala Val Ala Arg Tyr Ala Pro Ser Gly Ser Arg Asp
305                 310                 315                 320

Arg Asp Asp Gly Val Ala Met Val Ser Glu Ile Ala Gly Ile Thr Cys
                325                 330                 335

Ser Ser Gly Met Gly Gly Gln Gly Val Val Cys Lys Lys
            340                 345
```

<210> SEQ ID NO 23
<211> LENGTH: 21

```
<212> TYPE: DNA
<213> ORGANISM: Artificial sequence
<220> FEATURE:
<223> OTHER INFORMATION: synthetic sequence

<400> SEQUENCE: 23
tggcgaagaa gcagaggcag a                                             21

<210> SEQ ID NO 24
<211> LENGTH: 20
<212> TYPE: DNA
<213> ORGANISM: Artificial sequence
<220> FEATURE:
<223> OTHER INFORMATION: synthetic sequence

<400> SEQUENCE: 24
ttgaggggga gggtaaaaag                                               20

<210> SEQ ID NO 25
<211> LENGTH: 19
<212> TYPE: DNA
<213> ORGANISM: Artificial sequence
<220> FEATURE:
<223> OTHER INFORMATION: synthetic sequence

<400> SEQUENCE: 25
gaagaagggg atgaaggag                                                19

<210> SEQ ID NO 26
<211> LENGTH: 20
<212> TYPE: DNA
<213> ORGANISM: Artificial sequence
<220> FEATURE:
<223> OTHER INFORMATION: synthetic sequence

<400> SEQUENCE: 26
tacggacaaa cacactacag                                               20

<210> SEQ ID NO 27
<211> LENGTH: 19
<212> TYPE: DNA
<213> ORGANISM: Artificial sequence
<220> FEATURE:
<223> OTHER INFORMATION: synthetic sequence

<400> SEQUENCE: 27
cctccaacaa ccaccactg                                                19

<210> SEQ ID NO 28
<211> LENGTH: 19
<212> TYPE: DNA
<213> ORGANISM: Artificial sequence
<220> FEATURE:
<223> OTHER INFORMATION: synthetic sequence

<400> SEQUENCE: 28
tcaagcgcac aacaaggtc                                                19

<210> SEQ ID NO 29
<211> LENGTH: 21
<212> TYPE: DNA
<213> ORGANISM: Artificial sequence
<220> FEATURE:
<223> OTHER INFORMATION: synthetic sequence

<400> SEQUENCE: 29
aggtggtggt cagaagaaga c                                             21
```

<210> SEQ ID NO 30
<211> LENGTH: 20
<212> TYPE: DNA
<213> ORGANISM: Artificial sequence
<220> FEATURE:
<223> OTHER INFORMATION: synthetic sequence

<400> SEQUENCE: 30
gacacactgg aaagctgcta                                         20

<210> SEQ ID NO 31
<211> LENGTH: 21
<212> TYPE: DNA
<213> ORGANISM: Artificial sequence
<220> FEATURE:
<223> OTHER INFORMATION: synthetic sequence

<400> SEQUENCE: 31
ccaataacag ctcaagaatc a                                       21

<210> SEQ ID NO 32
<211> LENGTH: 19
<212> TYPE: DNA
<213> ORGANISM: Artificial sequence
<220> FEATURE:
<223> OTHER INFORMATION: synthetic sequence

<400> SEQUENCE: 32
ttcccttcca tcccactct                                          19

<210> SEQ ID NO 33
<211> LENGTH: 21
<212> TYPE: DNA
<213> ORGANISM: Artificial sequence
<220> FEATURE:
<223> OTHER INFORMATION: synthetic sequence

<400> SEQUENCE: 33
gaacaggccc atcccttatt g                                       21

<210> SEQ ID NO 34
<211> LENGTH: 17
<212> TYPE: DNA
<213> ORGANISM: Artificial sequence
<220> FEATURE:
<223> OTHER INFORMATION: synthetic sequence

<400> SEQUENCE: 34
cggcgcttgg cattgta                                            17

<210> SEQ ID NO 35
<211> LENGTH: 16
<212> TYPE: DNA
<213> ORGANISM: Artificial sequence
<220> FEATURE:
<223> OTHER INFORMATION: synthetic sequence

<400> SEQUENCE: 35
atgcgcactg acaaca                                             16

<210> SEQ ID NO 36
<211> LENGTH: 19
<212> TYPE: DNA
<213> ORGANISM: Artificial sequence
<220> FEATURE:
<223> OTHER INFORMATION: synthetic sequence -continued
<210> SEQ ID NO 37
<211> LENGTH: 17
<212> TYPE: DNA
<213> ORGANISM: Artificial sequence
<220> FEATURE:
<223> OTHER INFORMATION: synthetic sequence

<400> SEQUENCE: 37
gctgtgcgcg tgctgat                                                17

<210> SEQ ID NO 38
<211> LENGTH: 15
<212> TYPE: DNA
<213> ORGANISM: Artificial sequence
<220> FEATURE:
<223> OTHER INFORMATION: synthetic sequence

<400> SEQUENCE: 38
caggagcaca tcgat                                                  15

<210> SEQ ID NO 39
<211> LENGTH: 29
<212> TYPE: DNA
<213> ORGANISM: Artificial sequence
<220> FEATURE:
<223> OTHER INFORMATION: synthetic sequence

<400> SEQUENCE: 39
tgtgctcctg atgctctctg tccttgtgc                                   29

<210> SEQ ID NO 40
<211> LENGTH: 28
<212> TYPE: DNA
<213> ORGANISM: Artificial sequence
<220> FEATURE:
<223> OTHER INFORMATION: synthetic sequence

<400> SEQUENCE: 40
atagtgacct taatagcgat cttgttgc                                    28

<210> SEQ ID NO 41
<211> LENGTH: 26
<212> TYPE: DNA
<213> ORGANISM: Artificial sequence
<220> FEATURE:
<223> OTHER INFORMATION: synthetic sequence

<400> SEQUENCE: 41
ccaaatcaaa tcaaaccaag caaatc                                      26

<210> SEQ ID NO 42
<211> LENGTH: 10
<212> TYPE: DNA
<213> ORGANISM: Arabidopsis thaliana

<400> SEQUENCE: 42 ryacgtggyr                                                        10

<210> SEQ ID NO 43
<211> LENGTH: 29
<212> TYPE: DNA
<213> ORGANISM: Artificial sequence -continued

```
<220> FEATURE:
<223> OTHER INFORMATION: synthetic sequence

<400> SEQUENCE: 43
ttgaagcttg tggacatgac ggaagaggt                                        29

<210> SEQ ID NO 44
<211> LENGTH: 36
<212> TYPE: DNA
<213> ORGANISM: Artificial sequence
<220> FEATURE:
<223> OTHER INFORMATION: synthetic sequence

<400> SEQUENCE: 44
gcagatctac catggacgac tcctgttatt agaaaa                                36

<210> SEQ ID NO 45
<211> LENGTH: 23
<212> TYPE: DNA
<213> ORGANISM: Artificial sequence
<220> FEATURE:
<223> OTHER INFORMATION: synthetic sequence

<400> SEQUENCE: 45
cactggcact actggagcct atg                                              23

<210> SEQ ID NO 46
<211> LENGTH: 15
<212> TYPE: DNA
<213> ORGANISM: Artificial sequence
<220> FEATURE:
<223> OTHER INFORMATION: synthetic sequence

<400> SEQUENCE: 46
ctggagcaca tggga                                                       15
```